United States Patent [19]

Young et al.

[11] Patent Number: 4,609,744

[45] Date of Patent: Sep. 2, 1986

[54] 4-OXO-BENZOPYRAN CARBOXYLIC ACIDS

[75] Inventors: Robert N. Young, Senneville; Joshua Rokach, Laval; Haydn R. Williams, Dollard Des Ormeaux, all of Canada Masatoshi Kakushima, Yokohama, Japan; Yvan Guindon, Ile Bizard, Montreal, Canada

[73] Assignee: Merck Frosst Canada Inc., Kirkland, Canada

[21] Appl. No.: 591,343

[22] Filed: Mar. 19, 1984

Related U.S. Application Data

[63] Continuation-in-part of Ser. No. 487,331, Apr. 21, 1983, abandoned.

[51] Int. Cl.⁴ ............ C07D 311/22; C07D 311/24
[52] U.S. Cl. .................... 549/402; 549/400; 549/401; 549/403; 549/289; 549/287; 549/79; 549/60; 549/51; 549/23; 548/482; 548/525; 546/156; 546/157; 546/269; 546/342; 544/359; 544/380; 544/383
[58] Field of Search ............... 549/401, 402, 403, 400

[56] References Cited

U.S. PATENT DOCUMENTS

| | | | |
|---|---|---|---|
| 4,252,818 | 2/1981 | Rokach et al. | 549/402 |
| 4,296,129 | 10/1981 | Kadis | 560/37 |
| 4,299,969 | 11/1981 | Huffman | 560/9 |

FOREIGN PATENT DOCUMENTS

| | | |
|---|---|---|
| 0068739 | 1/1983 | European Pat. Off. |
| 0026307 | 4/1984 | European Pat. Off. |
| 1936463 | 2/1971 | Fed. Rep. of Germany |
| 49-5971 | 1/1974 | Japan ................ 549/402 |
| 57-118555 | 7/1982 | Japan |
| 2058785 | 4/1981 | United Kingdom |
| 2094301 | 9/1982 | United Kingdom |

OTHER PUBLICATIONS

Piper et al., Ann Rpts. Med. Chem., 15 69 (1980).
Borgeat and Sirois, J. Med. Chem., 24 121 (1981).
Samuelsson, Science, 220 568 (1983).
Bailey et al., Ann Rpts. Med. Chem., 17 203 (1982).
Chemical Abstracts, vol. 86, No. 13, Columbus, Ohio, U.S.A., R. A. Appleton et al., p. 14, abstract No. 86:83500n, J. Med. Chem., 1977, 20(3), pp. 371-379.
Chemical Abstracts, vol. 97, No. 3, Columbus, Ohio, U.S.A., P. Sheard et al.: p. 44, abstract-No. 97:16807g & Adv. Prostaglandin, Thromboxane, Leukotriene Res., 1982, 9 (Leukotrienes, etc.), pp. 229-235.

Primary Examiner—Nicky Chan
Attorney, Agent, or Firm—Gabriel Lopez; Paul H. Ginsburg; Hesna J. Pfeiffer

[57] ABSTRACT

Compounds of the Formula I:

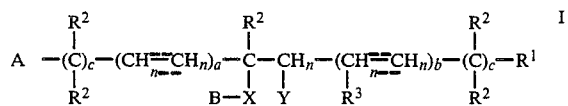

and pharmaceutically acceptable salts thereof are leukotriene antagonists. These compounds inhibit SRS-A and leukotriene synthesis and are antagonists of SRS-A and are thus useful in the treatment of asthma, allergic disorders, inflammation, skin diseases and certain cardiovascular disorders.

5 Claims, No Drawings

4-OXO-BENZOPYRAN CARBOXYLIC ACIDS

REFERENCE TO RELATED APPLICATION

This application is a continuation-in-part of U.S. Ser. No. 487,331, filed Apr. 21, 1983 abandoned.

BACKGROUND OF THE INVENTION

This invention is directed to new chemical compounds, especially useful as antagonists of the slow reacting substance of analphylaxis (SRS-A) and the major components thereof, the leukotrienes $C_4$, $D_4$ and $E_4$; as well as of leukotriene $B_4$.

It is known that certain substances play an important role in inducing an allergic reaction, such as asthma, allergic bronchitis or allergic rhinitis, in man. Examples of such substances are SRS-A and its major components, the leukotrienes. See: P. Borgeat and P. Sirois, *J. Med. Chem.*, 24, 121 (1982) and P. J. Piper, *Ann. Rpts. Med. Chem.*, 15 69 (1980).

SRS-A and the leukotrienes $C_4$, $D_4$ and $E_4$, affect the smaller peripheral airways of the larger central passages such as the trachea and the bronchi. In the presence of an allergic trigger like pollen or dust, these leukotrienes are manufactured from fatty substances trapped in the membrane of a triggered cell. A series of reactions within the cell generates this mixture of leukotrienes which may then pass through the cell membrane into the bloodstream. Once in the blood, these leukotrienes constrict air passages producing breathlessness.

Leukotriene $B_4$, which is not part of SRS-A, is an important chemotactic factor which induces migration of polymorphic cells and thus contributes to both inflammation and allergic diseases.

SUMMARY OF THE INVENTION

This invention is directed to novel compounds of the Formula I:

$$A-(C)_c-(CH=CH_n)_a-C-CH_n-(CH=CH_n)_b-(C)_c-R^1$$

with substituents $R^2$, $R^2$, $B-X$, $Y$, $R^3$, $R^2$ and pharmaceutically acceptable salts thereof wherein the various substituents are as defined herein below.

This invention provides compounds that act as antagonists to prevent or reverse the actions of leukotrienes $C_4$, $D_4$ and $E_4$, and SRS-A and also leukotriene $B_4$.

This invention also provides a method to prevent the synthesis and/or release of SRS-A or the leukotrienes $C_4$, $D_4$ and $E_4$ as well as leukotriene $B_4$, in a human subject. This method comprises administering to said subject an effective amount of a compound of Formula I or a pharmaceutically acceptable salt thereof, optionally in a pharmaceutically acceptable carrier.

Finally, methods of preparing the compounds of Formula I are provided herein.

DETAILED DESCRIPTION OF THE INVENTION

The present invention is directed to novel compounds which have activity as antagonists of SRS-A and leukotrienes. The invention is also directed to methods of preparation and to methods of using the novel compounds described herein. Because of their activity as leukotriene antagonists, the compounds of the present invention are useful in preventing and treating allergic conditions such as, chronic bronchitis, allergic rhinitis, asthma; skin diseases such as, psoriasis, atopic exema; inflamation and cardiovascular disorders such as angina.

The compounds of this invention are best realized by Formula I:

$$A-(C)_c-(CH=CH_n)_a-C-CH_n-(CH=CH_n)_b-(C)_c-R^1 \quad I$$

with substituents $R^2$, $R^2$, $B-X$, $Y$, $R^3$, $R^2$ and pharmaceutically acceptable salts thereof, wherein;

X is O, S, SO, $SO_2$;

n is 0–2 as required to maintain four bonds to carbon; the broken lines represent optional double and triple bonds;

b and c are each independently 0 to 5;

$R^1$ is $COOR^2$, $CH_2OH$, CHO, tetrazole, hydroxymethyl ketone, CN, $CONR^2R^4$, a monocyclic or bicyclic heterocyclic ring containg an acidic hydroxyl group or $NHSO_2R^4$; or $$-COO(-CH_2)_s-\underset{R^{14}}{\overset{R^{14}}{\underset{|}{\overset{|}{C}}}}(CH_2)_s-R^{15}$$

wherein each s is independently 0–3; each $R^{14}$ is independently H or alkyl of 1 to 4 carbons which may be straight chain or branched; $R^{15}$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical X—$R^{16}$ wherein X is O, S or NH and $R^{16}$ contains up to 21 carbon atoms which may be straight chain or branched and is (1) a hydrocarbon radical or (2) an acyl radical of an organic acyclic or monocyclic carboxylic acid containing not more than 1 heteroatom selected from N, O or S in the ring;

$R^2$ and $R^3$ are each independently H, lower alkyl or one $R^2$ and one $R^3$ may be connected by a 1C or 2C containing bridge to form a cyclic ring which may have 0, 1, 2 or 3 double bonds;

$R^4$ is H; alkyl; hydroxyl; halogen; haloalkyl; benzyl; benzyl substituted with at least one $R^7$; aryl; alkylarylalkyl; aryl substituted with at least one $R^5$; $NO_2$; CN; $SCF_3$; $OR^5$; O—benzyl; O—benzyl substituted with at least one $R^5$; O—aryl; O—aryl substituted with at least one $R^5$; $SR^5$; $NR^2R^5$; $SOR^5$ or $SO_2R^5$;

$R^5$ is H; alkyl; hydroxyl; halogen; haloalkyl; alkylarylalkyl; benzyl; benzyl substituted with at least one $R^3$; $NO_2$; CN; $SCF_3$; $OR^3$; O—benzyl; O—benzyl substituted with at least one $R^3$; O—aryl; O—aryl substituted with at least one $R^3$; $SR^3$; $NR^2R^3$; $SOR^3$ or $SO_2R^3$;

Y is H, OH, $OR^2$ or =O;

A is H,

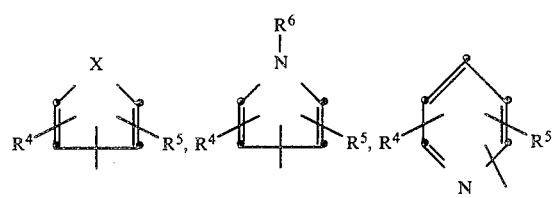
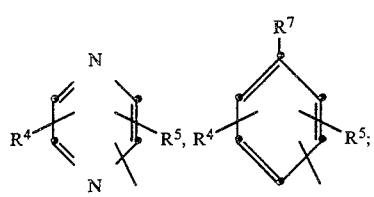
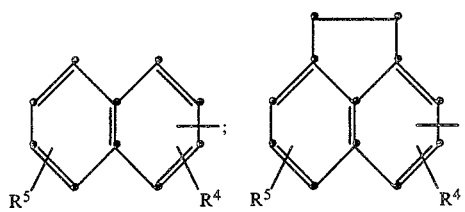
wherein the broken line represents an optional double bond;
R⁶ is H, lower alkyl, halogen, OR² or SR²;
R⁷ is H, alkylthioalkyl, alkylthiobenzyl or alkylthioaryl;
B is H,
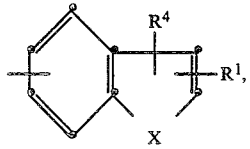
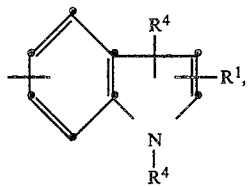
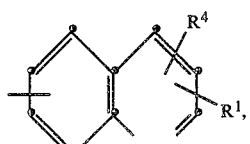
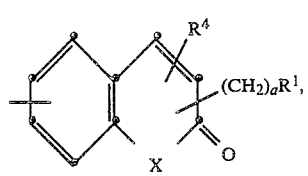
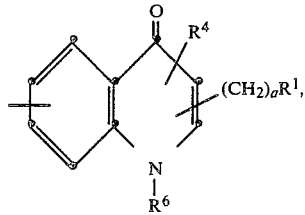
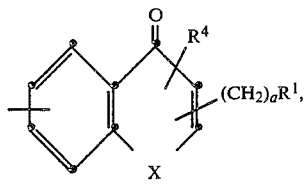
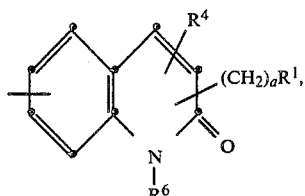
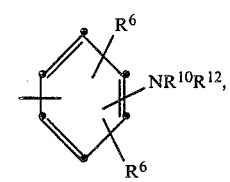
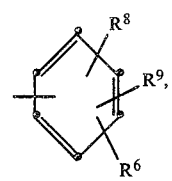
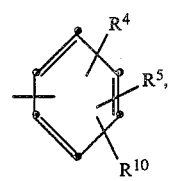
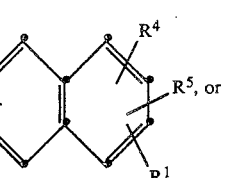
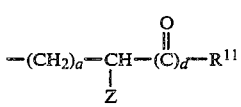
wherein
Z is H, NHR⁹, NR²R⁹, an N-terminal bonded essential amino acid or a lower alkyl ester thereof, OH, OR⁴ or OR²;
R⁸ is H, lower alkyl or —(CH₂)ₐR¹;
R⁹ is H, lower

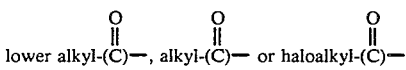

$R^{10}$ is

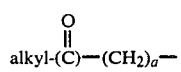

or

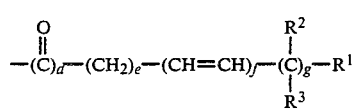

wherein e is 0 to 9 and f and g are independently 0 to 3;
$R^{11}$ is Z, wherein Z is as defined above, when d is 1, and $R^{11}$ is $R^1$ or Z, wherein Z is as defined above, when d is 0;
$R^{12}$ is H, acyl, formyl, CN or $SO_2R_{13}$;
$R^{13}$ is H, alkyl or aryl; each a in the above definitions is independently 0 to 5 and each d in the above definitions is independently 0 or 1.

As used herein, the term "lower alkyl" includes those alkyl groups of from 1 to 7 carbon atoms of either a straight, branched or cyclic configuration. The term also includes carbon fragments having one or more double or triple bonds. Examples of lower alkyl fragments include methyl, ethyl, propyl, isopropyl, butyl sec- and tert-butyl, pentyl hexyl, heptyl, cyclopropyl, cyclobutyl, cyclopentyl, cyclohexyl, cycloheptyl, 1-propenyl, 2-butenyl, 2-methyl-2-butenyl, 2-butynyl and the like.

As used herein, the term alkyl includes lower alkyl and extends to cover carbon fragments having up to 20 carbon atoms in straight, branched or cyclic configurations. Moreover, alkyl includes carbon fragments having one or more double or triple bonds, conjugated or unconjugated. Examples of alkyl groups include octyl, nonyl, undecyl, dodecyl, tridecyl, tetradecyl, pentadecyl, eicosyl, 3,7-ethyl-2,2-methyl-4-propylnonane and the like.

As used herein, the term aryl means the carbon containing aromatic structures phenyl, naphthyl, anthracenyl, phenanthrenyl, pyrenyl, phenyl substituted with one or more alkyls, naphthyl substituted with one or more alkyls, anthracenyl substituted with one or more alkyls, and phenanthrenyl substituted with one as more alkyl.

As used herein, heterocyclic rings include 5 or 6 membered rings containing one or more heteroatoms selected from O, N, S and bicyclic fused rings containing one or more heteroatoms selected from O, N or S. Generally useful heterocyclic rings (where the the broken lines indicate optional double bonds) include:

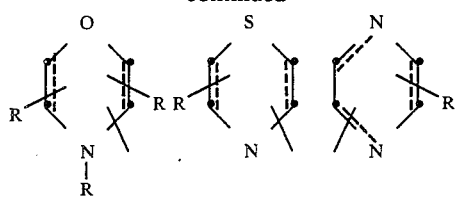

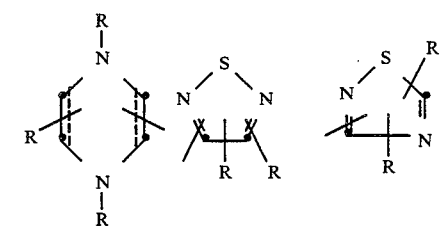

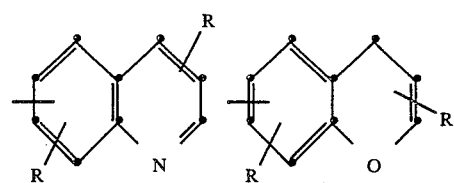

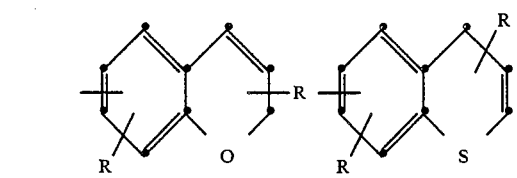

and the like, wherein R is any of $R^1$, $R^2$, $R^3$, $R^4$, $R^5$, $R^6$, $R^8$ or $R^9$.

As used herein, the term halogen refers to F, Cl, Br and I.

As used herein, the N-terminally bound essential amino acids are defined as follows: L-alanine, L-valine, L-leucine, L-isoleucine, L-proline, L-phenylalanine, L-tryptophan, L-methionine, L-glycine, L-serine, L-threonine, L-cycteine, L-tyrosine, L-asparagine, L-glutamine, L-lysine, L-arginine, L-histidine, aspartic acid and glutamic acid. The enantiomeric D-amino acids may also be used as N-terminally bonded essential amino acids.

A preferred group of compounds is represented by Formula II:

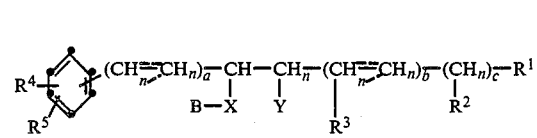

wherein:
n is 0-2 as required to maintain four bonds to carbon; the broken lines represent optional double or triple bonds; b and c are each idependently 0-5; and
$R^2$ and $R^3$ are each independently H, lower alkyl or one $R^2$ and one $R^3$ may be connected by a 1C or 2C bridge to form a cyclic ring which may have 0, 1, 2 or 3 double bonds;
$R^1$ is $COOR^2$, $CH_2OH$, CHO, tetrazole, hydroxymethyl ketone, CN, $CONR^2R^4$, a monocyclic or bicyclic heterocyclic ring containg an acidic hydroxyl group or $NHSO_2R^4$; or

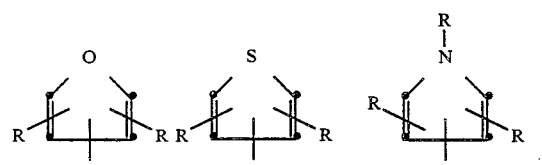

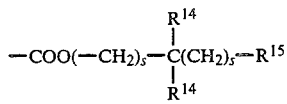

wherein each s is independently 0-3; each $R^{14}$ is independently H or alkyl of 1 to 4 carbons which may be straight chain or branched; $R^{15}$ is (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or (B) the radical $X$—$R^{16}$ wherein X is O, S or NH and $R^{16}$ contains up to 21 carbon atoms which may be straight chain or branched and is (1) a hydrocarbon radical or (2) an acyl radical of an organic acyclic or monocyclic carboxylic acid containing not more than 1 heteroatom selected from N, O or S in the ring;

$R^4$ is H; alkyl; hydroxyl; halogen; haloalkyl; benzyl; benzyl substituted with at least one $R^7$; aryl; aryl substituted with at least one $R^5$; $NO_2$; CN; $SCF_3$; $OR^5$; O—benzyl; O—benzyl substituted with at least one $R^5$; O—aryl; O—aryl substituted with at least one $R^5$; $SR^5$; $NR^2R^5$; $SOR^5$ or $SO_2R^5$;

$R^5$ is H; alkyl; hydroxyl; halogen; haloalkyl; benzyl; benzyl substituted with at least one $R^3$; $NO_2$; CN; $SCF_3$; $OR^3$; O—benzyl; O—benzyl substituted with at least one $R^3$; O—aryl; O—aryl substituted with at least one $R^3$; $SR^3$; $NR^2R^3$; $SOR^3$ or $SO_2R^3$;

$R^7$ is H, alkylthioalkyl, alkylthiobenzyl or alkylthioaryl;

Y is H or OH;

X is O or S;

B is H,

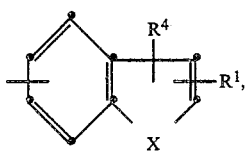

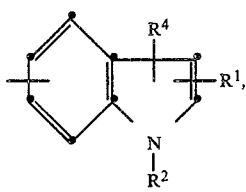

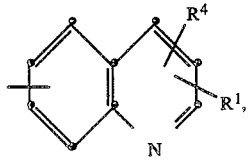

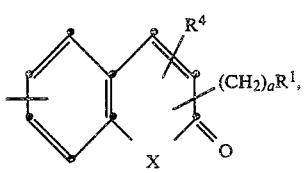

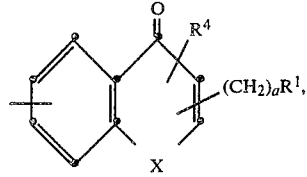

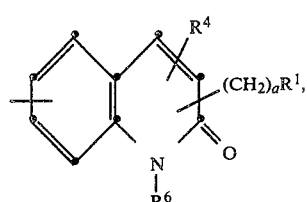

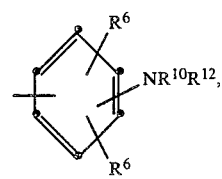

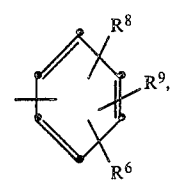

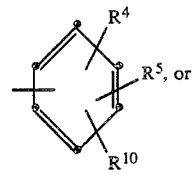

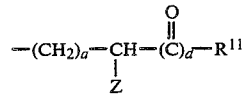

wherein

Z is H, $NHR^9$, $NR^2R^9$, an N-terminal bonded essential amino acid or a lower alkyl ester thereof, OH, $OR^4$ or $OR^2$;

each $R^6$ is H, lower alkyl, halogen, $OR^2$, $SR^2$, $SOR^4$ or $SO_2R^5$;

$R^8$ is H, lower alkyl or —$(CH_2)_aR^1$;

$R^9$ is H, $$\text{loweralkyl-}\overset{O}{\overset{\|}{C}}\text{—, alkyl-}\overset{O}{\overset{\|}{C}}\text{— or haloalkyl-}\overset{O}{\overset{\|}{C}}\text{—};$$

$R^{10}$ is

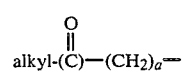

or

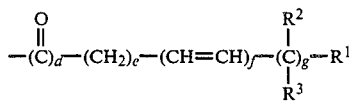

wherein e is 0 to 9 and f and g are independently 0 to 3;
$R^{11}$ is Z, wherein Z is as defined above, when d is 1 and $R^{11}$ is $R^1$ or Z, wherein Z is as defined above, when d is 0;
$R^{12}$ is as defined for Formula I; each a in the above definitions is independently 0 or 1 and each d in the above definitions is independently 0 or 1.

More preferred are the compounds of Formula II wherein B is selected from:

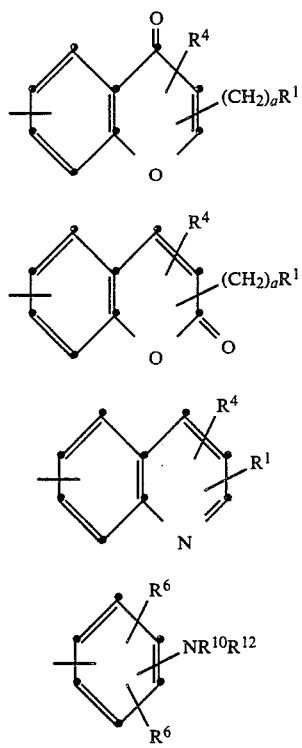

wherein the substituents are as defined above.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium. calcium, magnesium, ferrous, zinc, copper, manganous, aluminum, ferric, manganic salts and the like. Particularly preferred are the potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylaminoethanol, tomethamine, lysine, arginine, histidine, caffeine, procaine, hydrabamine, choline, imidazole, betaine, ethylenediamine, glucosamine, methylglucamine, theobromine, purines, piperazine, N,N'-dibenzylethylenediamine, piperidine, N-ethylpiperidine, morpholine, N-ethylmorpholine, polyamine resins and the like.

As indicated above, the compound of Formula I are active as antagonists of SRS-A and the leukotrienes $B_4$, $C_4$, $D_4$ and $E_4$. This activity can be detected and evaluated by methods known in the art. See for example, Kadin, U.S. Pat. No. 4,296,129.

The ability of the compounds of Formula I to antagonize the effects of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma.

A compound of Formula I, or a pharmaceutically acceptable salt thereof, can be administered to a human subject either alone, or preferably, in combination with pharmaceutically acceptable carriers or diluents, in a pharmaceutical composition, according to standard pharmaceutical practice. A compound can be administered orally or parenterally. Parenteral administration includes intravenous, intramuscular, intraperitoneal, subcutaneous and topical administration, and also administration by inhalation and insufflation.

For oral use of an leukotriene antagonist of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic. For administration by inhalation or insufflation, it is convenient to prepare an aqueous or partially aqueous solution of a compound of Formula I or salt thereof, and then this solution is administered in form of an aerosol.

When a compound of Formula I or salt thereof is used as an leukotriene antagonist in a human subject, the daily dosage will normally be determined by the prescribing physician. Moreover, the dosage will vary according to the age, weight and response of the individual patient, as well as the severity of the patient's symptoms. However, in most instances, and effective daily dosage will be in the range from about 0.1 to about 40 mg per kg, and preferably 0.2 to 20 mg per kg, most preferably 1 to 10 mg per kg in a single or divided doses. On the other hand, it may be necessary to use dosages outside these limits in some cases.

In addition to the compounds of Formula I, pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDS can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprufen, ketoprufen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, aluminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

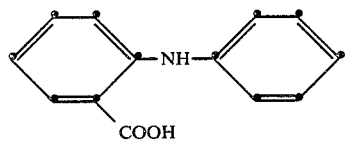

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

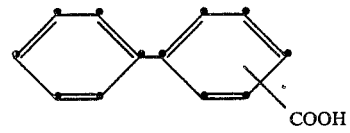

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4-hydroxyl-1,2-benzothiazine 1,1,-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

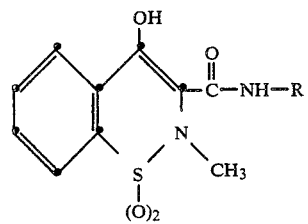

wherein R is an aryl or heteroaryl ring system.

The following NSAIDS may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3. ITC1, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones and pharmaceutically acceptable salts thereof.

Pharmaceutical compositions comprising the Formula I compounds may also contain inhibitors of the biosynthesis of the leukotrienes such as are disclosed in pending U.S. patent applications Ser. No. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application 11,067 or thromboxane antagonists such as those disclosed in U.S. Pat. No. 4,237,160. They may also contain histidine decarboxyase inhibitors such as a-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; European Patent Application No. 40,696 and a pending application. U.S. Ser. No. 301,616, filed Sept. 14, 1981. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

PREPARATION OF COMPOUNDS—GENERAL DESCRIPTION

The compounds of Formula I may be prepared by any process available to the skilled artisan. General reaction schemes are as follows:

SCHEME 1

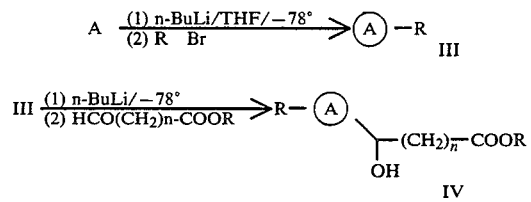

As described in Scheme 1, heteroaromatics A such as thiophene, furan and the like, may be reacted with a strong base, such as n-butyllithium. The resulting lithiated compound may then be reacted with an alkyl or alkenyl halide compound to produce the compound III.

Compound III may be reacted with a strong base, such as n-butyllithium, and the resulting lithiated species may be reacted with an omega-formyl alkanoic acid ester to yield a compound of Formula IV.

SCHEME 2

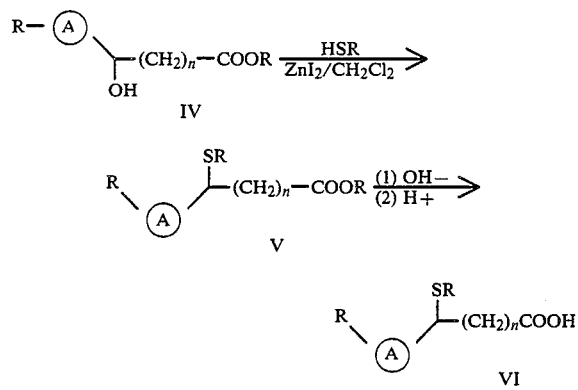

Compounds of Formula IV (all aromatics) may be reacted with a thiol in the presence of a Lewis Acid such as zinc iodide to yield the thiol compound of Formula V (Scheme 2).

Compound V may be hydrolyzed by conventional means to yield the free acid compound of Formula VI.

SCHEME 3

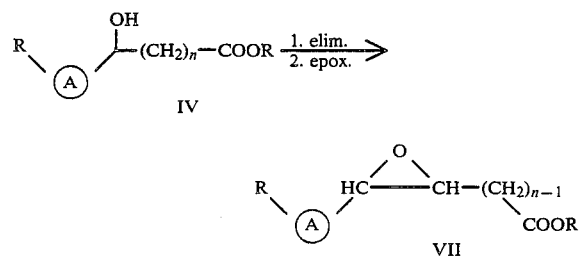

Compounds of Formula IV may be treated with a catalytic amount of a strong acid, for example, p-toluenesulfonic acid, to eliminate water, thus forming an olefin. This olefin may then be reacted with an epoxidizing agent, such as m-chloroperbenzoic acid, to provide an epoxide compound of Formula VII (Scheme 3).

SCHEME 4

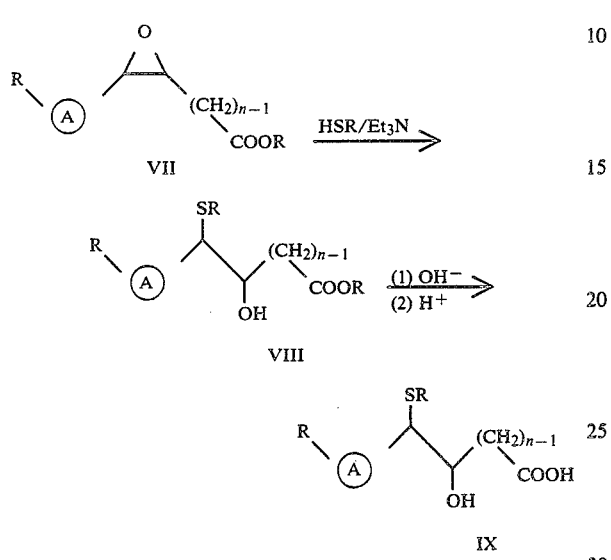

As shown in Scheme 4, the epoxide compounds of Formula VII may be reacted with a thiol compound in the presence of a base such as triethylamine, sodium hydride, and the like, to yield a β-hydroxy sulfide compound of the Formula VIII. The β-hydroxy sulfide compound VIII may be hydrolyzed by conventional means to provide the free acid compound of Formula IX.

SCHEME 5

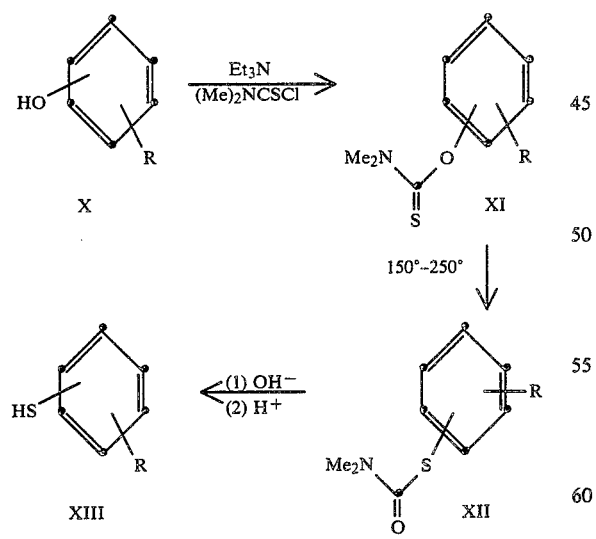

A phenol of general Formula X (Scheme 5) may be reacted with dimethyl thiocarbamylchloride in the presence of a base such as triethylamine, sodium hydride and the like to yield the compound having general Formula XI. Compound XI may be heated at from 150° to 250° C. either neat or in a suitable solvent, to provide the compound of Formula XII. Compound XII may be reacted with a base such as an alkoxide or hydroxide, and followed by acidification, generates the thiol compounds having the Formula XIII.

SCHEME 6

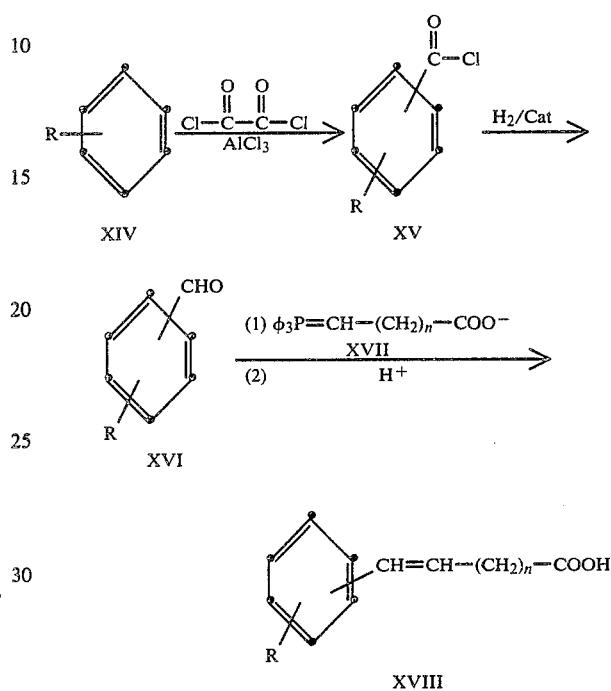

Substituted aromatic compounds having the general Formula XIV (Scheme 6) may be reacted with oxalyl chloride in the presence of a Lewis Acid, such as aluminum chloride, to provide the acid chloride compound of Formula XV. The acid chloride may be reduced by conventional means, for example by catalytic hydrogenation, to provide the aldehyde of general Formula XVI. Aldehyde XVI may be reacted with a Wittig reagent of general Formula XVII to yield, following acidification, the olefin compound of Formula XVIII.

SCHEME 7

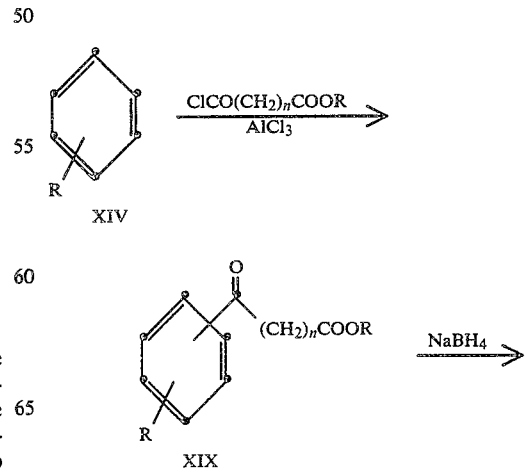

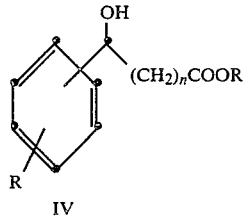

Substituted aromatic compounds of general Formula XIV may be reacted with an omega chloroformyl alkanoic acid ester or cyclic anhydride in the presence of a Lewis Acid, such as aluminum chloride to provide the ketone of general Formula XIX (Scheme 7).

Ketone XIX may be reduced using conventional techniques, for example, sodium borohydride, to provide the alcohol of general Formula IV.

SCHEME 8

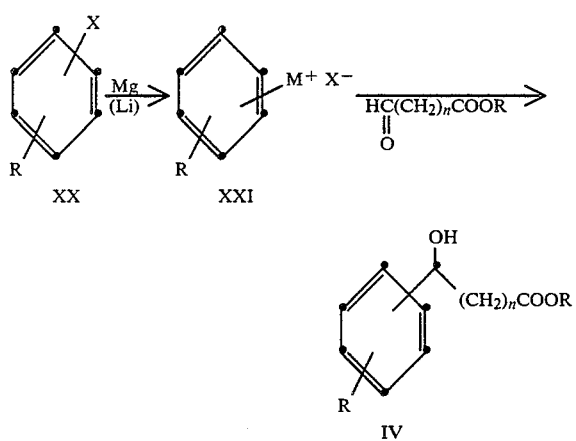

Halogen (Cl, Br, I) substituted aromatic compounds of general Formula XX may be reacted with magnesium or lithium to generate the metalated species XXI. The metalated species may be reacted with an omega-formyl alkanoic acid ester to provide the alcohol of general Formula IV (Scheme 8).

SCHEME 9

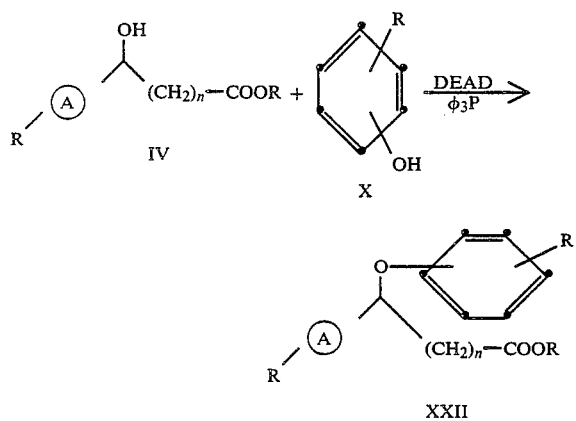

As shown in Scheme 9, an alcohol of general Formula IV may be reacted with a phenol of genera Formula X in the presence of a molar equivalent amount of diethylazodicarboxylate (DEAD) and triphenylphosphine to provide the ether compound of general Formula XXII.

Pro-drug esters wherein $R^1$ is a monocyclic or bicyclic heterocyclic ring containing an acidic hydroxyl group are obtained by reacting the appropriate heterocycle with a compound of Formula I ($R^1$=COOH) in the presence of dicyclohexylcarbodiimide and hydroxybenzotriazole in an inert solvent such as DMF.

Pro-drug esters wherein $R^1$ is

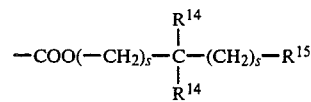

are obtained by reacting the sodium salt of Formula I ($R^1$=COONa) with

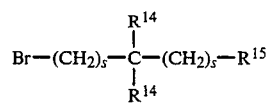

in an inert solvent such as DMF.

The following examples are provided to aid in the interpretation of the present invention. They are not intended to limit the scope of the invention in any manner. Infrared (IR) spectra were measured as KBr disks or as thin films and absorption bands are reported in reciprocal centimeters (cm$^{-1}$). Nuclear magnetic resonance (NMR) spectra (90 MHz) were measured in deuterochloroform (CDCl$_3$), perdeuterodimethyl sulfoxide (DMSO-d$_6$), deuteromethanol (CD$_3$OD), deuterium oxide (D$_2$O) or deuterated trifluoroacetic acid (CF$_3$COOD) and peak positions are expressed in parts per million (ppm) downfield from an internal reference, tetramethylsilane. The following abbreviations are used for peak shapes: s, singlet; d, doublet; t, triplet; q, quartet; and m, multiplet. All melting and boiling points are reported in degrees Centigrade (°C.) and are uncorrected.

Examples 1-12 describe the preparation of intermediates used herein to prepare the novel compounds of Formula I.

EXAMPLE 1

Preparation of Methyl 4-oxo-7-mercapto-8-propyl-4H-1-benzopyran-2-carboxylate

Step 1. Ethyl 7-((dimethylamino)thioxomethoxy)-4-oxo-8-propyl-4H-1-benzopyran-2-carboxylate Ethyl 7-hydroxy-4-oxo-8-n-propyl-4H-1-benzopyran-2-carboxylate (1 g) in anhydrous DMF (4 ml) was cooled to 0° and treated under N$_2$ with sodium hydride (50% dispersion in mineral oil, 180 mg) with stirring for 30 min. Dimethylthiocarbamylchloride (465 mg) was added and the mixture was stirred 15 minutes at 0°, warmed to 80° and maintained as such for 18 hours. The mixture was cooled, diluted with CH$_2$Cl$_2$ (50 ml) and washed with water (3×100 ml), dried over Na$_2$SO$_4$ and reduced to dryness in vacuo. The residue was recrystallized from ethyl acetate and hexane to yield the title compound, m.p. 132°-134°.

Analysis, calculated: C, 59.50; H, 5.82; N, 3.85; S, 8.82.
Observed: C, 59.60; H, 5.47; N, 3.73; S, 8.56.

Step 2. Ethyl 7-(((dimethylamino)carbonyl)thio)-4-oxo-8-propyl-4H-1-benzopyran-2-carboxylate The ester prepared in Step 1 (1 g) was heated neat and under a nitrogen atmosphere at 200° for 2 hours. After cooling the residue was crystallized from ethyl acetate and hexane to yield the title compound, m.p. 113°–114°.

Analysis: calculated: C, 59.50; H, 5.82; N, 3.85; S, 8.82.
Observed: C, 59.49; H, 5.94; N, 3.86; S, 9.10.

Step 3. 7-Mercapto-4-oxo-8-propyl-4H-1-benzopyran-2-carboxylic acid

Sodium (690 mg) was dissolved in anhydrous methanol (50 ml) and to this was added the ester from Step 2. The mixture was stirred under a nitrogen atmosphere for 3 hours at ambient temperature. Water (50 ml) was added and the mixture was acidified with 6N HCl. The resulting crystals were collected by filtration and recrystallized from ethyl acetate to provide the title compound, m.p. 206°–208°.

Analysis, calculated: C, 59.08; H, 4.58; S, 12.13.
Observed: C, 59.50; H, 4.55; S, 11.92.

Step 4. Methyl 4-oxo-7-mercapto-8-propyl-4H-1-benzopyran-2-carboxylate

The acid from Step 3 (6.6 g) is dissolved in a mixture of hydrogen chloride (18 g) and anhydrous methanol (200 ml). The mixture is stirred overnight under $N_2$ atmosphere at ambient temperature. The mixture was reduced to dryness in vacuo to provide the title compound, m.p. 98°–99°.

EXAMPLE 2

Preparation of Methyl 7-mercapto-4H-1-benzopyran and 2-hydroxymethyl-7-mercapto-4-oxo-4H-1-benzopyran-2-carboxylate

Step 1. Ethyl 7-((dimethylamino)thioxomethoxy)-4-oxo-4H-1-benzopyran-2-carboxylate Following the procedure of Step 1, Example 1, but substituting an equivalent amount of ethyl 7-hydroxy-4-oxo-4H-1-benzopyran-2-carboxylate for ethyl 7-hydroxy-8-n-propyl-4H-1-benzopyran-2-carboxylate was obtained the title compound, m.p. 160°–161°.

Step 2. Ethyl 7-(((Dimethylamino)carbonyl)thio-4-oxo-4H-1-benzopyran-2-carboxylate Following the general procedure of Step 2 of Example 1 but substituting an equivalent amount of the ester from Step 1 above for Ethyl-7-(dimethylamino)thioxomethoxy)-4-oxo-8-propyl-4H-1-benzopyran-2-carboxylate was obtained the title compound, m.p. 142°–143°.

Analysis, calculated: C, 56.07; H, 4.70; S, 9.98.
Observed: C, 55.95; H, 4.70; S, 9.98.

Step 3. 7-mercapto-4-oxo-4H-1-benzopyran-2-carboxylic acid

Following the procedure of Step 3 of Example 1 but substituting an equivalent amount of the ester of Step 2 above for ethyl 7-(((dimethylamino)-carbonyl)thio)-4-oxo-8-propyl-4H-benzopyran-2-carboxylate was obtained the title compound, m.p. 261° (decomposition).

Step 4. Methyl 7-Mercapto-4-oxo-4H-1-benzopyran-2-carboxylate

Following the procedure of Step 4 of Example 1 but substituting an equivalent amount of the acid from Step 3 above for 7-mercapto-4-oxo-8-n-propyl-4H-1-benzopyran-2-carboxylic acid, was obtained the title compound, m.p. 147°–150°.

Analysis, calculated: C, 55.93; H, 3.41; S, 13.57.
Observed: C, 55.53; H, 3.40; S, 13.69.

Step 5. 2-hydroxymethyl-7-mercapto-4-oxo 4H-1-benzopyran

The ester from Step 4, (3.0 g) in suspension in methanol (20 ml) and water (40 ml) at 0° was stirred vigorously during the portionwise addition of $NaBH_4$ (1.8 g). The mixture was stirred 2 hours more at 5°. Acetone (1 ml) was added followed by acidification with 12N HCl and extraction with methanol-chloroform (1:9, 3×50 ml). The extracts were dried ($Na_2SO_4$) reduced to dryness in vacuo and the residue was recrystallized from methanol-ethyl acetate to provide the title compound, m.p. 139°–140°.

Analysis, calculated: C, 57.68; H, 3.87; S, 15.40.
Observed: C, 58.10; H, 3.73; S, 15.53.

EXAMPLE 3

Preparation of N-((4-chlorophenyl)methyl)-2-mercaptobenzamide 2,2'-Dicarboxydiphenyldisulfide-bis-N-(4-chlorophenylmethyl)amide (see, C.A., 54, 6623), (1.5 g) in suspension in ethanol (50 ml) is refluxed while sodium borohydride was added in portions over 3 hours. The mixture was stirred at room temperature overnight. The mixture was filtered, the filter cake washed with water (50 ml) and the resulting combined filtrates were acidified with 6N HCl and the resulting solids were dissolved by warming. The ethanol was removed by evaporation in vacuo and the resulting crystals were collected by filtration to provide the title compound, m.p. 131°–132°.

Analysis, calculated: C, 60.54; H, 4.35; N, 5.01; S, 11.54.
Observed: C, 60.33; H, 4.44; N, 5.05; S, 11.42.

EXAMPLE 4

Preparation of Methyl 6-mercapto-2-oxo-2H-1-benzopyran-2-carboxylate

Step 1. Ethyl 6-(((dimethylamino)thio)methoxy)-2-oxo-2H-1-benzopyran-3-carboxylate Following the procedure of Step 1, Example 1, but substituting an equivalent amount of ethyl 6-hydroxy-2-oxo-2H-1-benzopyran-3-carboxylate (See C.A. 50, 13895C) for ethyl 7-hydroxy-4-oxo-8-n-propyl-4H-1-benzopyran-2-carboxylate, was obtained the title compound, m.p. 157°–160°.

Step 2. Ethyl 6-(((dimethylamino)carbonyl)thio)-2-oxo-2H-1-benzopyran-3-carboxylate Following the general procedure of Step 2, Example 1, but substituting the ester from Step 1 above for ethyl 7-((dimethylamino)thioxomethoxy)-4-oxo-8-propyl-4H-benzopyran-2-carboxylate, was obtained the title compound, m.p. 133°–134°.

Analysis, calculated: C, 56.06; H, 4.71; N, 4.36; S, 9.98.

Observed: C, 56.34; H, 4.71; N, 4.30; S, 10.18.

Step 3. Methyl 6-mercapto-2H-1-benzopyran-3-carboxylate

The ester from Step 2 above, (1.0 g) was heated under reflux in a mixture of 2N NaOH (40 ml) and ethanol (0.2 ml) under a nitrogen atmosphere for 40 hours. After cooling the mixture was poured into ice water (50 ml) and acidified with 6N HCl. The resulting solid was collected by filtration and dried in vacuo, then dissolved in a mixture of anhydrous HCl (2 g) and anhydrous methanol (20 ml). The mixture was left at 0° for 2 days, then reduced to dryness in vacuo to provide the title compound as an unstable oil.

NMR (90 MHz) (CDCl$_3$): 3.6 (1H, exchanged by D$_2$O, SH), 3.95 (3H, s, OCH$_3$), 7.22 (1H, d), 7.6 (2H, m), 8.45 (1H, s).

EXAMPLE 5

Preparation of (2-hydroxy-3-n-propyl-4-mercaptophenyl)ethanone

Following the procedure described in Example 4 but substituting 2,4-dihydroxy-3-n-propylphenylethanone for ethyl 6-hydroxy-2H-1-benzopyran-3-carboxylate in Step 1 were obtained sequentially; (2-hydroxy-3-n-propyl-4-(((dimethylamino)thioxo)methoxy)-phenyl)ethanone, m.p. 85°.

Analysis, calculated: C, 59.77; H, 6.81; N, 4.98; S, 11.38.

Observed: C, 60.02; H, 7.02; N, 5.10; S, 11.00. (2-hydroxy-3-propyl-4-(((diethylaminocarbonyl)thio)-phenyl)ethanone, m.p. 61°–62°.

Analysis, calculated: C, 59.77; H, 6.81; N, 4.98; S, 11.38.

Observed: C, 60.17; H, 6.78; N, 5.05; S, 11.26. and the title compound, as an oil; NMR (90 MHz) (CDCl$_3$): 0.99 (3H, t), 1.62 (2H, m) 2.54 (3H, s), 2.70 (2H, m), 3.64 (1H, s, —SH), 6.71 (1H, d, J=9 Hz), 7.37 (1H, d, J=9 Hz), 12.81 (1H, s, OH).

EXAMPLE 6

Preparation of (2-hydroxy-4-mercaptophenyl)ethanone

Following the procedure described in Example 4 but substituting 2,4-dihydroxyphenylethanone for ethyl-6-hydroxy-2-oxo-2H-1-benzopyran-3-carboxylate in Step 1 were obtained sequentially:

(1) (2-hydroxy-4-(((dimethylamino)thioxo)methoxy)-phenyl)ethanone, m.p. 143°–146°, Analysis, calculated: C, 55.21; H, 5.47; N, 5.85; S, 13.40.

Observed: C, 55.24; H, 5.16; N, 5.88; S, 13.20;

(2) (2-hydroxy-4-(((dimethylamino)carbonyl)thio)-phenyl)ethanone, m.p. 131°–133°, Analysis calculated: C, 55.21; H, 5.47; N, 5.85; S, 13.40.

Observed: C, 55.49; H, 5.21; N, 5.84; S, 13.25;

and the title compound, (2-hydroxy-4-mercaptophenyl)ethanone m.p. 63°–65°,

Analysis, calculated: C, 57.12; H, 4.79; S, 19.06

Observed: C, 57.35; H, 4.79; S, 19.22.

EXAMPLE 7

Preparation of Methyl((2-acetyl-5-mercapto)phenoxy)acetate

Step 1. Ethyl(2-acetyl-5-(((dimethylamino)carbonyl)thio)-phenoxy)acetate

To a suspension of the phenol from Step 2 of Example 6 (20 g) in anhydrous dimethyl formamide (200 ml) under an atmosphere of nitrogen, was added 99% NaH (1.36 g). After stirring 15 minutes at ambient temperature ethyl bromoacetate (11.2 ml) was added and the mixture was stirred 2 hours more. Water (600 ml) was added and the mixture was extracted with ether (4×200 ml). The combined extracts were washed with water (2×200 ml) dried (Na$_2$SO$_4$) and reduced to dryness. Chromatography of the residue on silica gel provided the title compound, m.p. 68°–69°.

Analysis, calculated: C, 55.37; H, 4.89; N, 4.30; S, 9.86.

Observed: C, 55.39; H, 4.92; N, 4.16; S, 9.77.

Step 2. (2-Acetyl-5-(((dimethylamino)carbonyl)thio)phenoxy)acetic acid

A solution of the ester from Step 1 (1.0 g) in THF (17 ml) was treated with 0.2N NaOH (17 ml) and stirred 5 minutes at ambient temperature. The mixture was diluted with water (50 ml), acidified with 12N HCl and the mixture was extracted with CH$_2$Cl$_2$ (2×100 ml). The extracts were washed with water, dried (Na$_2$SO$_4$) and reduced to dryness to provide the title compound, m.p. 173°–174°.

Analysis, calculated: C, 52.51; H, 5.09; N, 4.71; S, 10.79.

Observed: C, 52.33; H, 5.05; N, 4.58; S, 10.60.

Step 3. (2-Acetyl-5-mercaptophenoxy)acetic acid

A solution of the product from Step 1 (4.5 g) (or alternatively a similar equivalent of the compound from Step 2) in methanol (33 ml) and 1N NaOH (33 ml) was refluxed in a N$_2$ atmosphere for 18 hours. The mixture was cooled, diluted with water (100 ml), acidified with 12N HCl, and extracted with ethyl acetate (3×100 ml). The combined organic extracts were washed with saturated brine, dried (Na$_2$SO$_4$) and reduced to dryness to yield the title compound, m.p. 149°–150°.

Analysis, calculated: C, 53.08; H, 4.46; S, 14.17

Observed: C, 52.83; H, 4.46; S, 13.73.

Step 4. Methyl((2-acetyl-5-mercapto)phenoxy)acetate

The product from Step 3 (1.7 g) was dissolved in a mixture of anhydrous HCl (1.53 g) and methanol (17 ml) and left 5 minutes at room temperature. The solvents were removed in vacuo and the residue was dissolved in CH$_2$Cl$_2$, washed with water, dried (Na$_2$SO$_4$) and reduced to dryness to provide the title compound, m.p. 75°–77°.

EXAMPLE 8

Preparation of Methyl 3-methyl-6-mercapto-benzofuran-2-carboxylate

Step 1. Ethyl 6-(((dimethylamino)carbonyl)thio)-3-methyl-benzofuran-2-carboxylate The ester from Step 1 of Example 7 (10 g) in dry toluene (160 ml) was treated with 1,5-diazabicyclo[3.4.0]nonene-5 (DBN) (4.6 ml) and the mixture is refluxed under a Dean Stark water separator for 18 hours. The mixture was reduced to dryness and the residue was chromatographed on silica gel to provide the title compound, m.p. 112°–114°.

Analysis, calculated: C, 58.61; H, 5.58; N, 4.56; S, 10.43.

Observed: C, 58.80; H, 5.63; N, 4.53; S, 10.13.

Step 2. 6-(((dimethylamino)carbonyl)thio)-3-methyl-benzofuran-2-carboxylic acid A suspension of the ester from Step 1 above (0.8 g) in THF (14 ml) was treated with 0.2N NaOH (14.3 ml) and methanol (1 ml) at room temperature for 18 hours. The mixture was diluted with water, acidified with 12N HCl and extracted with ethyl acetate (3×50 ml). The combined extracts were washed with water (2×50 ml), dried ($Na_2SO_4$) and reduced to dryness in vacuo to provide the title compound, m.p. 188°–190°.

Analysis, calculated: C, 55.90; H, 4.69; N, 5.02; S, 11.48.

Observed: C, 55.77; H, 4.85; N, 5.00; S, 11.26.

Step 3. 6-Mercapto-3-methyl-benzofuran-2-carboxylic acid

Following the general procedure described in Step 3 of Example 7 but substituting an equivalent amount of the compound from Step 1 above (3.59 g) (or alternatively and equivalent amount of the compound from Step 2) for (2-acetyl-5(((dimethylamino)carbonyl)thio)phenoxy)acetic acid was obtained the title compound, m.p. 230°–232°.

Analysis, calculated: C, 57.68; H, 3.87; S, 15.40.

Observed: C, 57.78; H, 4.20; S, 15.48.

Step 4. Methyl 6-mercapto-3-methyl-2-benzofuran-carboxylate

Following the general procedure described in Step 4 of Example 7 but substituting an equivalent amount of the acid from Step 3 above for (2-acetyl-5-mercaptophenoxy)acetic acid, except that the mixture was left to stand for 18 hours instead of 5 mixtures, to provide the title compound, m.p. 118°–120°.

Analysis, calculated: C, 59.44; H, 4.54; S, 14.43.

Observed: C, 59.54; H, 4.79; S, 14.18.

EXAMPLE 9

Preparation of Methyl 7-mercapto-2-methoxyquinoline-3-carboxylate

Step 1. 3-(((4-(Methoxyphenyl)methyl)thio)analine

Sodium hydride (99%, 8.22 g) was added in portions of a stirred solution of 3-aminothiophenol (44.23 g) in dry DMF (132 ml) at 0°. After 30 minutes a solution of 4-methoxybenzylchloride (53.61 g) in acetonitrile (132 ml) was added dropwise and the mixture was stirred 30 minutes at 0° and 1 hour more at ambient temperature. The mixture was poured into ice-water (200 ml) and the resulting solid was collected by filtration and dried in air to provide the title compound, m.p. 85°–86°.

Step 2. N-(1,3-dioxo-3-ethoxy)propyl-3-(((4-methoxyphenyl)methyl)thio)analine The amine from Step 1 (250 g) and diethyl malonate (1.25 L) were stirred under a $N_2$ stream at 170°–180° for 2.5 hours. The volatile components were then removed by distillation in vacuo at 120°. The resulting melt was poured into t-butyl methyl ester (1 L) slowly with stirring, and the resulting solid was collected by filtration and washed with t-butyl methyl ether (250 ml) to provide the title compound, m.p. 81°–84°.

Step 3. Ethyl 2-chloro-7-(4-methoxy-phenylmethylthio)quinoline-3-carboxylate A mixture of oxalyl chloride (23.42 g) and DMF (13.48 g) in $CH_2Cl_2$ (500 ml) was prepared and cooled to 0°. The amide from Step 2 (33.1 g) was added and the mixture was stirred at ambient temperature for 48 hours. The mixture was reduced to dryness and chromatographed on silica gel (eluting with ethyl acetate:hexane 1:1) to provide the title compound, m.p. 110°–112°.

Step 4. Methyl 2-Methoxy-7-(((4-methoxyphenyl)methyl)thio)quinoline-3-carboxylate The ester from Step 3 (7.76 g) was added to a solution of sodium (9.20 mg) in anhydrous methanol (50 ml) and the resulting suspension was refluxed under an argon atmosphere for 75 minutes. The mixture was cooled, diluted with $CH_2Cl_2$ (200 ml), washed with water (3×50 ml) and reduced to dryness to provide the title compound, m.p. 133°–134.5°.

Analysis, calculated: C, 65.01; H, 5.18; N, 3.79; S, 8.68.

Observed: C, 65.07; H, 5.06; N, 3.72; S, 8.43.

Step 5. Methyl 7-mercapto-2-methoxyquinoline-3-carboxylate

A mixture of the ester from Step 4 (2.77 g), 90% formic acid (70 ml) and mercuric acetate (7.17 g) was stirred under an argon atmosphere at ambient temperature for 3 hours. The reaction mixture was poured into a mixture of water (350 ml) and $CH_2Cl_2$ (700 ml) and $H_2S$ gas was passed through the vigorously stirred mixture for 5 minutes. The organic phase was separated, filtered through celite, washed with water, dried ($MgSO_4$) and reduced to dryness to provide the title compound, m.p. 103°–105°.

Analysis, calculated: C, 57.81; H, 4.45; N, 5.62; S, 12.86.

Observed: C, 57.94; H, 4.40; N, 5.35; S, 12.81.

EXAMPLE 10

Preparation of n-Butyl 2-n-butoxy-7-mercaptoquinoline-3-carboxylate

Following the methodology described in Example 9 but sutstituting an equivalent amount of n-butanol for methanol in Step 4 was obtained sequentially:

n-butyl 2-n-butoxy-7-(4-methoxyphenylmethyl)thio)-quinoline-3-carboxylate, as an oil, Analysis, calculated: C, 68.00; H, 7.08; N, 3.17; S, 7.26.

Observed: C, 68.18; H, 6.71; N, 3.00; S, 6.97; and n-butyl 2-n-butoxy-7-mercapto-3-quinoline-carboxylate as an oil, NMR (CDCl$_3$): 1:0 (6H, t), 1.2–1.9 (8H, m), 4.4 (4H,m), 7.16 (1H, dd), 7.58 (1H, d), 8.38 (1H, S).

EXAMPLE 11

Preparation of Methyl 7-mercapto-4-methyl-2-oxo-8-n-propyl-2H-1-benzopyran-3-acetate

Step 1. Methyl 7-hydroxy-4-methyl-2-oxo-2H-1-benzopyran-3-acetate

7-Hydroxymethyl-2-oxo-2H-1-benzopyran-3-acetic acid (see C.A. 64, 15826f) was dissolved in a mixture of HCl (gas) (10 g) and anhydrous methanol (90 ml) and left 1 hour at room temperature. The resulting crystals were collected by filtration and washed with ether to provide the title compound, m.p. 194°–196°.

Step 2. Methyl (2-propenyloxy-4-methyl-2-oxo-2H-1-benzopyran-3-acetate

The ester from Step 1 (500 mg) was added to a suspension of NaH (98%, 58 mg) in anhydrous DMF (5 ml) and the mixture was stirred 30 minutes at ambient temperature. Allyl bromide (262 μl) was added and the mixture was heated at 70° for 3 hours. The mixture was cooled, poured into water (20 ml) and HCl (2 equivalents) and the solution was extracted with ether (2×50 ml). The extracts were washed with water (2×50 ml), dried (Na$_2$SO$_4$), reduced to dryness and chromatographed on silica gel (eluting with ethyl acetate-hexane 1:2) to provide the title compound, m.p. 72°–73°.

Analysis, calculated: C, 66.66; H, 5.60.
Observed: C, 66.73; H, 5.69.

Step 3. Methyl 7-hydroxy-4-methyl-2-oxo-8-(2-propenyl)-2H-1-benzopyran-3-acetate The ether from Step 2 (35.9 g) was refluxed in dichlorobenzene (50 ml) under N$_2$ atmosphere for 18 hour. The mixture was cooled, diluted with hexane and the resulting crystals were collected by filtration. Trituration with ether and filtration of the resulting solid gave the title compound, m.p. 160°–162°.

Analysis, calculated: C, 66.66; H, 5.60.
Observed: C, 66.54; H, 5.45.

Step 4. Methyl 7-hydroxy-4-methyl-2-oxo-8-propyl-2H-1-benzopyran-3-acetate

The phenol from Step 3 (23 g) was hydrogenated in methanol (700 ml) under 50 psi H$_2$ pressure in the presence of 5% palladium on charcoal (2 g) for 1 hour. The catalyst was removed by filtration over celite and the solvent was removed to provide the title compound, m.p. 160°–162°.

Analysis, calculated: C, 66.19; H, 6.25.
Observed: C, 66.34; H, 6.04.

Step 5. Methyl 7-((dimethylamino)thioxomethoxy)-4-methyl-2-oxo-8-propyl-2H-1-benzopyran-3-acetate Following the general procedure described in Example 1, Step 1, but substituting an equivalent amount of the phenol from Step 4 above for ethyl-7-hydroxy-4-oxo-8-propyl-4H-1-benzopyran carboxylate was obtained the title compound, m.p. 172°–173°.

Analysis, calculated: C, 60.46; H, 6.14; N, 3.71; S, 8.50.
Observed: C, 60.46; H, 6.17; N, 3.71; S, 7.95.

Step 6. Methyl 7-(((dimethylamino)carbonylthio)-4-methyl-2-oxo-8-propyl-2H-benzopyran-3-acetate Following the general procedure described in Example 1, Step 2, but substituting an equivalent amount of the ester from Step 5 above for ethyl (((dimethylamino)-thioxo)methoxy)-4-oxo-8-propyl-4H-1-benzopyran-3-carboxylate, was obtained the title compound, m.p. 131°–132°.

Analysis, calculated: C, 60.46; H, 6.14; N, 3.71, S, 8.50.
Observed: C, 60.57; H, 6.05; N, 3.69; S, 8.29.

Step 7. Methyl 7-mercapto-4-methyl-2-oxo-8-propyl-2H-1-benzopyran-3-acetate

Following the procedure described in Example 1, Step 2, but substituting the ester from Step 6 above for ethyl 4-oxo-8-propyl-7-(((dimethylamino)-carbonyl)thio)-4H-1-benzopyran-2-carboxylate, and after chromatography of the collected solid on silica gel was obtained the title compound, directly, m.p. 133°–134°.

Analysis, calculated: C, 62.72; H, 5.92; S, 10.47.
Observed: C, 62.74; H, 5.68; S, 10.38.

EXAMPLE 12

Preparation of 3-((3-Methoxy-1,3-dioxopropyl)amino)phenylmercaptan

A mixture of 3-aminothiophenol (5.0 g) and diethyl malonate (6.41 g) was heated under a nitrogen atmosphere for 2 hours at from 165° to 170° C. The mixture was chromatographed on silica gel to obtain the title compound, m.p. 52°–54°. Analysis, calculated: C, 55.21; H, 5.47; N, 5.85, S, 13.39.
Observed: C, 54.64; H, 5.41; N, 5.80; S, 13.02.

Examples 13–125 describe the preparation of the novel compounds of the instant invention.

EXAMPLE 13

Preparation of D,L-Erythro-6-(2-carboxyethylthio)-5-hydroxy-6-phenyl-hexanoic acid bis-(dicyclohexylammonium)salt

Step 1. (E)- and (Z)-6-Phenyl-5-hexenoic acid methyl esters 4-(Carboxybutyl)triphenylphosphonium bromide (41.8 g) was added in portions to a suspension of potassium t-butoxide (26.4 g) in anhydrous tetrahydrofuran (THF) (500 ml) at 0° under N$_2$ atmosphere. The mixture was stirred 45 minutes at 0° and the benzaldehyde (10 g) was added dropwise over 30 minutes and the mixture was stirred an additional 45 minutes, then diluted with water (500 ml) and washed with CHCl$_3$ (500 ml). The CHCl$_3$ extract was washed with water and the combined aqueous phases were acidified with 12N HCl and then extracted with ethyl acetate (3×400 ml), the extracts were washed with water and dried (Na$_2$SO$_4$) and reduced to dryness. The residue was purified by chromatography on silica gel to yield (E) and (Z)-6-phenyl-5-hexenoic acid as a mixture which was esterified in anhydrous diethyl ether with excess diazomethane to yield the title mixture of compounds as an oil. NMR (60

MHz) (CDCl$_3$): 1.7–2.6 (H,m), 3.60, 3.63 (3H, 2S), 5.4–6.6 (2H, m), 7.30 (5H, broad s).

Step 2. D,L-E- and Z-5,6-Epoxy-6-phenylhexanoic acid methyl esters

The mixture of esters from Step 1 (5.20 g) was dissolved in CH$_2$Cl$_2$ (250 ml) and cooled to 0°. A solution of 85% m-chloroperbenzoic acid (7.76 g) in CH$_2$Cl$_2$ (150 ml) was added and the mixture was stirred 22 hours at ambient temperature. 10 percent aqueous Na$_2$SO$_4$ (50 ml) was added, and then the mixture was extracted with 5% Na$_2$CO$_3$ (200 ml) water (200 ml), dried over Na$_2$SO$_4$ and reduced to dryness. The resulting oil was purified by chromatography on silica gel to provide:

D,L-(Z)-5,6-epoxy-6-phenylhexanoic acid methyl ester as an oil, NMR (60 MHz) (CDCl$_3$): 1.3–2.5 (6H, m), 3.16 (1H, m), 3.60 (3H, s), 4.05 (1H, d, J-4 Hz), 7.26 (5H, s); and D,L-(E)-5,6-epoxy-6-phenylhexanoic acid methyl ester as an oil, NMR (60 MHz) (CDCl$_3$): 1.70 (4H, m), 2.30 (2H, m), 2.85 (1H, m), 3.60 (1H, d, J-2 Hz), 3.66 (3H, s), 7.30 (5H, s).

Step 3.
D,L-Erythro-epsilon-(2-carboxyethylthio)-delta-hydroxyphenylhexanoic acid dimethyl ester D,L-(E)-5,6-epoxy-6-phenylhexanoic acid methyl ester from Step 2 (700 mg) in anhydrous MeOH (1.85 ml) and triethylamine (1.93 ml) was treated under N$_2$ atmosphere with methyl 3-mercapto propionate (1.15 ml) at ambient temperature for 5 days. The mixture was reduced to dryness and purified on silica gel to provide the title compound, as an oil: NMR (60 MHz) (CDCl$_3$): 1.7 (4H, m), 2.2–2.8 (6H, m), 3.68 (6H, s), 3.90 (2H, m), 7.34 (5H, s).

Step 4.
D,L-Erythro-epsilon-(2-carboxyethylthio)-delta-hydroxy-6-phenylhexanoic acid bis-(dicyclohexylammonium) salt The diester from Step 3 (846 mg) in THF (30 ml) was stirred with 0.2N LiOH (31.1 ml) for 2 hours at ambient temperature. The mixture was diluted with water (30 ml), acidified with 12N, HCl, and extracted with ethyl acetate (2×75 ml). The extracts were washed with brine, dried (Na$_2$SO$_4$) and reduced to dryness. The residue was dissolved in CH$_2$Cl$_2$ (20 ml) and treated withd dicyclohexylamine (0.96 ml). The mixture was reduced to dryness and the residue was recrystallized from methanol-ethyl acetate to provide the title compound, m.p. 123°–125°.

Analysis, calculated: C, 67.39; H, 10.15; N, 4.05; S, 4.61.
Observed: C, 67.64; H, 9.84; N, 4.05; S, 4.43.

EXAMPLE 14

Step 1. 5S,6R and 5R,6S-5-hydroxy-6-S-(N-trifluoroacetylglutathionyl)-hexanoic acid trimethyl ester Following the procedure of Example 13, Step 3, but substituting an equivalent N-trifluoroacetylglutathione dimethyl ester for methyl 2-mercaptoacetate, was obtained the title compound.

Analysis, calculated: C, 49.76; H, 5.57; N, 6.45; S, 4.92.
Observed: C, 49.66; H, 5.53; N, 6.49; S, 5.08.

Step 2.

The product from Step 1 (500 mg) was treated in a methanol (5 ml) with 0.204N NaOH (15.05 ml) with stirring at ambient temperature overnight. The mixture was reduced to dryness under high vacuum to provide the title compound, as a trihydrate containing one equivalent of sodium trifluoroacetate.

Analysis, calculated: C, 37.45; H, 4.45; N, 5.46; S, 4.17.
Observed: C, 37.40; H, 4.50; N, 5.32; S, 4.33.

EXAMPLE 15

Preparation of Methyl epsilon-(butylthio)-(4-nonylbenzene)hexanoate

Step 1. Methyl epsilon-oxo-(4-n-nonylphenyl)hexanoate

To methyl (5-chloroformyl)pentanoate (5.02 ml) was added to a stirred suspension of anhydrous aluminum chloride (9.26 g) in anhydrous 1,2-dichloroethane and the mixture stirred under N$_2$ atmosphere at ambient temperature for 5 minutes. 1-Phenylnonane (6.9 ml) was added and after 5 minutes the mixture was poured into water. The mixture was extracted with CH$_2$Cl$_2$ (3×100 ml) and the combined organic phases were washed with brine, dried (Na$_2$SO$_4$) and reduced to dryness to provide the title compound, m.p. 38°–39°.

Step 2. Methyl epsilon-hydroxy-(4-n-nonylphenyl)hexanoate

The ketone from Step 1 (9.19 g) was stirred in methanol (70 ml) and sodium borohydride (1.36 g) was added in portions. The mixture was poured into saturated NH$_4$Cl solution, and extracted with CH$_2$Cl$_2$ (3×100 ml). The organic phases were washed with water, dried (Na$_2$SO$_4$) and reduced to dryness to provide the title compound as an oil.

Analysis, calculated: C, 75.81; H, 10.41.
NMR (90 MHz) (CDCl$_3$) 0.85 (3H, t), 1.1–1.9 (20H, m), 2.26 (2H, t), 2.60 (3H, t and s, 1H exchanged by D$_2$O), 3.60 (3H, S), 4.57 (1H, t), 7.15 (4H, q).

Step 3. Methyl epsilon-butylthio-4-nonylbenzenehexanoate

The alcohol from Step 2 (2.0 g) was dissolved in anhydrous 1,2-dichloroethane (20 ml); zinc iodide (367 mg) and n-butylmercaptan (1.23 ml) was added and the mixture was stirred 19 hours at ambient temperature. The mixture was reduced to dryness and the residue was chromatographed on silica gel to provide the title compound as an oil.

Analysis, calculated: C, 74.23; H, 10.54; S, 7.62.
Observed: C, 73.86; H, 10.75; S, 7.30.

EXAMPLE 16

Preparation of Sodium epsilon-(phenylthio)-4-nonylbenzenehexanoate

Step 1. Methyl epsilon-(phenylthio)-4-nonyl-benzenehexanoate

Following the procedure described in Example 15, but substituting an equivalent amount of phenylthiotrimethylsilane for n-butylmercaptan in Step 3, was obtained the title compound as an oil.

Analysis, calculated: C, 76.31; H, 9.15; S, 7.28.
Observed: C, 76.36; H, 9.30; S, 7.39.

Step 2. Sodium epsilon-(phenylthio)-4-nonylbenzenehexanoate

The ester from Step 1 (1.0 g) was dissolved in THF (10 ml), 2N LiOH (13.6 ml) was added and the mixture was stirred at ambient temperature for 18 hours. The mixture was diluted with water (30 ml) acidified with 6N HCl, and extracted with $CH_2Cl_2$ (3×50 ml). The organic phases were washed with brine and reduced to dryness. A portion of the residue (640 mg) in methanol (10 ml) was treated with 0.2N NaOH (9.8 ml) for 30 minutes. The methanol was removed by evaporation and the aqueous mixture was applied to a column of Amberlite XAD-8. The column was washed with water until the effluent was neutral, then with methanol. The methanol washes were reduced to dryness to provide the title compound, as a foam.

Analysis, calculated: C, 72.28; H, 8.31; S, 7.15.
Observed: C, 71.80; H, 8.64; S, 6.84.

EXAMPLE 17

Preparation of Methyl epsilon-((2-carboxyethyl)thio)-4-nonylbenzenehexanoate Following the procedure described in Example 15 but substituting an equivalent amount of 3-mercaptopropionic acid for n-butylmercaptan in Step 3 was obtained the title compound, as an oil.

Analysis, calculated: C, 68.76; H, 9.23; S, 7.34.
Observed: C, 68.44; H, 9.83; S, 7.20.

EXAMPLE 18

Preparation of Methyl epsilon-((3-methoxy-3-oxo-propyl)thio)-4-nonylbenzenehexanoate Following the procedure described in Example 15 but substituting an equivalent amount of methyl 3-mercaptopropionate for n-butylmercaptan in Step 3 was obtained the title compound as an oil.

Analysis, calculated: C, 69.29; H, 9.39; S, 7.12.
Observed: C, 69.53; H, 10.07; S, 6.98.

EXAMPLE 19

Preparation of Epsilon-((2-carboxyethyl)thio)-4-nonylbenzenehexanoic acid

The ester from Example 17 (1.03 g) was dissolved in THF (15 ml) and 0.2N LiOH (25.2 ml) and stirred 18 hours at ambient temperature. The mixture was diluted with water (20 ml), acidified with 6N HCl and extracted with $CH_2Cl_2$ (3×50 ml). The combined organic phases were washed with brine, dried ($Na_2SO_4$) and reduced to dryness to provide the title compound, m.p. 61°–62°.

Analysis, calculated: C, 68.20; H, 9.06; S, 7.59.
Observed: C, 68.91; H, 9.39; S, 7.21.

EXAMPLE 20

Preparation of Epsilon-((3-methoxy-3-oxopropyl)thio)-4-nonylbenzenehexanoic acid

Step 1. Epsilon-hydroxy-(4-n-nonylbenzene)hexanoic acid

The ester from Example 15, Step 2, (2.0 g) was dissolved in THF (80 ml) and 0.2N LiOH (35 ml) and stirred 18 hours at ambient temperature. The mixture was diluted with water (200 ml), acidified and extracted with $CH_2Cl_2$ (3×160 ml). The combined organic extracts were washed with brine, dried ($Na_2SO_4$) and reduced to dryness to provide the title compound as an oil. NMR ($CDCl_3$): 0.87 (3H, m), 1.2–1.9 (20H, m), 2.27 (2H, t), 2.58 (2H, t), 4.68 (1H, t), 6.95 (2H, broad s, exchanged by $D_2O$), 7.18 (4H, m).

Step 2. Epsilon-(3-methoxy-3-oxo-propyl)thio)-4-n-nonyl-benzene phenyl hexanoic acid Following the procedure described in Example 15 but substituting an equivalent amount of acid from Step 1 above for methyl epsilon-hydroxy-4-n-nonylbenzenehexanoate and substituting an equivalent amount of methyl 3-mercaptopropionate for n-butylmercaptan in Step 3, was obtained the title compound, as an oil.

Analysis, calculated: C, 68.26; H, 9.23; S, 7.34.
Observed: C, 68.68; H, 9.51; S, 7.12.

EXAMPLE 21

Preparation of Methyl 7-((6-methoxy-6-oxo-1-(4-nonylphenyl)hexyl)thio)-4-oxo-8-propyl-4H-1-benzopyran-2-carboxylate Following the procedure described in Example 15 but substituting an equivalent amount of methyl 7-mercapto-8-propyl-2-oxo-4H-1-benzopyran-2-carboxylate for n-butylmercaptan in Step 3, was obtained the title compound, as an oil.

Analysis, calculated: C, 71.02; H, 7.95; S, 5.27.
Observed: C, 70.98; H, 8.37; S, 4.97.

EXAMPLE 22

Preparation of 7-(5-Carboxy-1-(4-nonylphenyl)pentyl)-4-oxo-8-propyl-4H-1-benzopyran-2-carboxylic acid disodium salt monohydrate Following the procedure described in Example 16, Step 2, but substituting an equivalent amount of the diester from Example 21 in place of methyl epsilon-(phenylthio)-4-nonylbenzenehexanoate, and using twice the equivalent amount of 0.2N LiOH, was obtained the title compound as an amorphous solid, m.p. 300°.

Analysis, calculated: C, 65.53; H, 6.90; S, 4.99.
Observed: C, 63.81; H, 7.15; S, 4.57.

EXAMPLE 23

Preparation of Methyl 7-((6-methoxy-6-oxo-1-(4-nonylphenyl)hexyl)thio-4-oxo-4H-1-benzopyran-2-carboxylate Following the procedure described in Example 15 but substituting an equivalent amount of methyl 7-mercapto-4-oxo-4H-1-benzopyran-2-carboxylate for 2-butyl mercaptan, was obtained the title compound, as an oil.

Analysis, calculated: C, 69.94; H, 4.69; S, 6.59.
Observed: C, 69.87; H, 7.48; S, 6.76.

EXAMPLE 24

Preparation of 7-(5-carboxy-1-(4-nonylphenyl)-pentyl)thio-4-oxo-4H-1-benzopyran-2-carboxylic acid disodium salt hemihydrate The diester from Example 23, (1.9 g) was stirred in THF (41 ml) and 0.2N NaOH (41 ml) at ambient temperature for 18 hours. The mixture was concentrated in vacuo to remove the THF and applied to column of Amberlite XAD-8 resin and the column was washed with water until the effluent was neutral. Eluting with ethanol gave after concentration to dryness of the effluent, the title compound, m.p. 318° (decomp.).

Analysis, calculated: C, 62.93; H, 6.30; S, 5.41.
Observed: C, 62.95; H, 6.29; S, 5.07.

EXAMPLE 25

Preparation of Methyl 7-(5-carboxy-1-(4-nonylphenylpentyl)thio-8-propyl-4-oxo-4H-1-benzopyran-2-carboxylate Following the procedure described in Example 20, but substituting an equivalent amount of methyl 4-oxo-7-mercapto-8-n-propyl-4H-1-benzopyran-2-carboxylate for methyl 2-mercaptoacetate in Step 2, was obtained the title compound, as a foam.

Analysis, calculated: C, 70.67; H, 7.80; S, 5.39.
Observed: C, 71.04; H, 7.58; S, 5.12.

EXAMPLE 26

Preparation of Epsilon (S) and epsilon (R)-epsilon-(L-cysteinyl)-(4-n-nonylphenyl)hexanoic acid

Step 1. Epsilon (S) and epsilon (R)-epsilon-(N-trifluoroacetylcysteinyl)-6-(4-n-nonylphenyl)-hexanoic acid dimethyl ester Following the procedure described in Example 15, but substituting an equivalent amount of N-trifluoroacetylcysteine methyl ester for n-butyl mercaptan in Step 3 was obtained the title compounds which were separated by chromatography on silica gel eluting with ethyl acetate:hexane (1:2) to yield the less polar isomer (isomer 1) as an oil.

Analysis, calculated: C, 59.87; H, 7.54; S, 5.71.
Observed: C, 59.91; H, 7.58; S, 5.63.

And the more polar isomer (isomer 2) as an oil.
Analysis, calculated: as above.
Observed: C, 60.11; H, 7.61; S, 5.68.

Step 2. S (6-Methoxy-1-(4-nonylphenyl)-6-oxohexyl)-L-cysteine disodium salt hemihydrate (diastereoisomer I)

Following the procedure described in Example 24, but substituting an equivalent amount of the isomer 1 from Step 2 above for methyl 7-((6-methoxy-6-oxo-1-(4-nonylphenyl)hexyl)thio-4-oxo-4H-1-benzopyran-2-carboxylate, and using four equivalents of 0.2N NaOH in place of the described amount of NaOH, was obtained the title compound as an amorphous solid.

Analysis, calculated: C, 58.75; H, 7.60; S, 6.53.
Observed: C, 58.69; H, 7.92; S, 6.23.

Step 3. S(6-Methoxy-1-(4-nonylphenyl)-6-oxohexyl)-L-cysteine disodium salt hemihydrate (diastereoisomer II)

Isomer 2 from Step 1 treated as in Step 2 above provided the title compound as an amorphous solid.
Analysis, calculated: C, 59.84; H, 7.74; S, 6.66.
Observed: C, 59.78; H, 7.97; S, 6.35.

EXAMPLE 27

Preparation of Epsilon S and epsilon R-epsilon-L-cysteinylglycyl-(4-n-nonylphenyl)hexanoic acid disodium salt

Step 1. Epsilon S and epsilon R-epsilon-N-trifluoroacetyl-L-cysteinylglycyl)-(4-nonylphenyl)hexanoic acid dimethyl ester Following the procedure described in Example 15 but substituting an equivalent amount of N-trifluoroacetylcysteinylglycine methyl ester for n-butyl mercaptan was obtained the title mixture of diastereomers as an oil.

Analysis, calculated: C, 58.23; H, 7.33; S, 5.18.
Observed: C, 57.91; H, 7.51; S, 5.02.

Step 2. Epsilon S and epsilon R-epsilon-cysteinylglycyl-(4-n-nonylphenyl)hexanoic acid disodium salt sesterhydrate Following the procedure described in Example 26, but substituting an equivalent amount of the diester from Step 1 above for epsilon-(N-trifluoroacetylcysteinyl)-(4-n-nonylphenyl)hexanoic acid dimethyl ester was obtained the title mixture of diastereomers as an amorphous solid.

Analysis, calculated: C, 53.50; H, 7.77; S, 5.49.
Observed: C, 53.49; H, 7.35; S, 4.89.

EXAMPLE 28

Preparation of D,L-((3-amino-3-oxopropyl)thio)-(4-n-nonyl)phenyl)-hexanoic acid sodium salt Following the procedure described in Example 16 but substituting an equivalent amount of 3-mercaptopropionamide for phenylthiotrimethylsilane in Step 1 was obtained, sequentially methyl epsilon-((3-amino-3-oxopropyl)thio-4-nonylbenzenehexanoate, m.p. 23°.

Analysis, calculated: C, 68.92; H, 9.49; N, 3.22; S, 7.36.
Observed: C, 68.61; H, 9.53; N, 2.92; S, 7.30; and the title compound; m.p. 131°–133°.

Analysis, calculated: C, 64.98; H, 8.63; N, 3.16; S, 7.23.
Observed: C, 65.27; H, 8.88; N, 2.81; S, 6.75.

EXAMPLE 29

Preparation of Methyl 4-nonyl-epsilon-((2-((trifluoroacetyl)amino)ethyl)thio)-benzenehexanoate Following the procedure described in Example 15 but substituting an equivalent amount of N-(2-mercaptoethyl)trifluoroacetamide for n-butylmercaptan was obtained the title compound as an oil.

Analysis, calculated: C, 62.00; H, 8.01; N, 2.78; S, 6.37.
Observed: C, 62.03; H, 8.14; N, 2.96; S, 6.28.

EXAMPLE 30

Preparation of Epsilon-((4-acetyl-3-hydroxyphenyl)-thio)-4-nonylbenzenehexanoic acid sodium salt Following the procedure described in Example 16 but substituting an equivalent amount of 3-hydroxy-4-acetylphenylmercaptan for phenylthiotrimethylsilane was obtained the title compound as a foam.

Analysis, calculated: C, 68.74; H, 7.76; S, 6.32.

Observed: C, 68.58; H, 7.89; S, 5.59.

EXAMPLE 31

Preparation of Methyl epsilon-((3-carboxyphenyl)thio)4-nonylbenzenehexanoate Following the procedure described in Example 15 but substituting an equivalent amount of 3-mercaptobenzoic acid in place of n-butylmercaptan was obtained the title compound. NMR (CDCl$_3$): 0.8–2.5 (27H, m); 3.5 (3H, s); 4.1 (1H, t); 6.9–7.8 (8H, m). Mass spectrum: m/e 470 (M+).

EXAMPLE 32

Preparation of Epsilon-((3-carboxyphenyl)thio)-4-nonylbenzenehexanoic acid

Following the procedure described in Example 19 but substituting an equivalent amount of the ester from Example 31, for methyl epsilon-((2-carboxyethyl)thio)-4-nonylbenzenehexanoate obtained the title compound as an oil. NMR (CDCl$_3$): 0.8–2.5 (27H, m); 4.1 (1H, t); 6.9–7.8 (8H, m).

EXAMPLE 33

Preparation of D,L-Epsilon-((4-carboxyphenyl)thio)-4-nonylbenzenehexanoic acid Following the procedure described in Example 15 but substituting an equivalent amount of 4-mercaptobenzoic acid for n-butylmercaptan was obtained D,L-epsilon-((4-carboxyphenyl)thio)-(4-n-nonylphenyl)hexanoic acid dimethyl ester. This diester was treated as described in Example 19, substituting an equivalent amount of epsilon-((2-carboxyethyl)thio)-4-nonylbenzenehexanoate, and utilizing double the equivalent amount of 0.2N LiOH, was obtained the title compound, m.p. 145°.

Analysis, calculated: C, 71.45; H, 8.14; S, 6.81.
Observed: C, 71.08; H, 8.02; S, 6.93.

EXAMPLE 34

Preparation of D,L-7-(5-carboxy-1-(4-nonylphenyl)-pentyloxy)-4-oxo-4H-1-benzopyran-2-carboxylic acid disodium salt Step 1. D,L-methyl 7-(6-methoxy-4-oxo-1-(4-nonylphenyl)hexyloxy)-4-oxo-4H-1-benzo-pyran)-2-carboxylate A mixture of methyl epsilon-hydroxy-(4-n-nonylphenyl)-hexanoate (2.0 g), 7-hydroxy-4-oxo-4H-1-benzopyran-2-carboxylic acid (1.35 g) and ml) was cooled to 0° and triphenylphosphine (3.0 g) was added. The mixture was stirred 30 minutes at 0°, 1 hour at ambient temperature, concentrated to an oil and purified by chromatography on silica gel to provide the title compound as an oil.

Analysis, calculated: C, 72.32; H, 7.85.
Observed: C, 72.35; H, 7.84.

Step 2. D,L-7-(5-carboxy-1-(4-nonylphenyl)pentyloxy)-4-oxo-4H-1-benzopyrano-2-carboxylic acid disodium salt The diester from above (1 g) was dissolved in 18 ml THF and 18 ml 0.2N NaOH and stirred 48 hours under N$_2$ atmosphere. The mixture was reduced to dryness to provide the title compound, m.p. 225° (decomp.).

Analysis, calculated: C, 63.69; H, 6.55.
Observed: C, 63.80; H, 6.57.

EXAMPLE 35

Preparation of D,L-Methyl epsilon-(2,4-dinitro-5-fluoro-phenoxy)-4-nonylbenzenehexanoate A mixture of methyl epsilon-hydroxy-4-n-nonylbenzene hexanoate (3.5 g), and 1,5-difluoro-2,4-dinitrobenzene (2.8 g) and triethylamine (1.65 ml) was stirred together in dichloromethane (200 ml) for 48 hours at ambient temperature. The mixture was reduced to dryness and purified by chromatography on silica gel to provide the title compound as an oil.

Analysis, calculated: C, 63.14; H, 7.00; N, 5.26; F, 3.57.
Observed: C, 62.96; H, 7.11; N, 4.97; F, 3.89.

EXAMPLE 36

Preparation of D,L-Epsilon-(5-((2-carboxyethyl)-amino)-2,4-dinitrophenoxy)-4-nonylbenzenehexanoic acid A mixture of the ester from Example 35 (1.51 g) and β-alanine (0.54 g) and 2N NaOH (10 ml) in THF (60 ml) was stirred 2 days at ambient temperature. The mixture was acidified with 6N HCl, diluted with brine (100 ml) and extracted with chloroform (3×52 m). The organic layers were dried (Na$_2$SO$_4$), reduced to dryness and chromatographed on silica gel to provide the title compound, as an oil.

Analysis, calculated: C, 61.31; H, 7.03; N, 7.16.
Observed: C, 61.53; H, 7.00; N, 7.81.

EXAMPLE 37

Preparation of D,L-Epsilon-(5-mercapto-2,4-dinitrophenoxy)-4-nonylbenzenehexanoic acid monohydrate Step 1. D,L-Methyl epsilon-(5-((3-oxo-3-aminopropyl)thio)-2,4-dinitrophenyloxy)-4-nonylbenzenehexanoate A mixture of the ester from Example 35 (1 g) and 3-mercaptopropionamide (0.25 g) and triethylamine (2.8 ml) in methanol (10 ml) was stirred at ambient temperature for 18 hours under N$_2$ atmosphere. The mixture was diluted with chloroform, washed with brine and reduced to dryness. The resulting oil was purified by chromatography on silica gel to provide the title compound: NMR (CDCl$_3$): 3.66 (3H, s), 5.48 (1H, m), 5.95 (2H, broad), 6.90 (1H, s), 7.30 (4H, m), 8.82 (1H, s).

Step 2. D,L-Epsilon-(5-mercapto-2,4-dinitro-phenoxy)-4-nonylbenzenehexanoic acid monohydrate The ester from Step 1 above (0.903 g) was stirred in THF (20 ml) and 1N NaOH (4.4 ml) for 24 hours. The mixture was diluted with water, washed with ether-hexane, acidified with 6N HCl, and extracted with chloroform. The CHCl$_3$ extracts were dried (Na$_2$SO$_4$) and reduced to dryness to yield an oil which was purified by chromatography on silica gel to provide the title compound as an oil.

Analysis, calculated: C, 58.89; H, 6.95; N, 5.09; S, 5.82.
Observed: C, 58.50; H, 6.63; N, 5.40; S, 6.36.

EXAMPLE 38

Preparation of D,L-Epsilon-hydroxy-(5-decylthiophene-2)-hexanoic acid

Step 1. 2-n-Decylthiophene

Thiophene (42 g) was added dropwise to a stirred soluton of n-butyllithium (0.495 mol) in hexane (330 ml) at −20° under $N_2$ atmosphere. The mixture was stirred 4 hours at −20° then 1-bromo-n-decane (110.6 g) in THF (50 ml) was added dropwise maintaining the temperature at −20°. The mixture was stirred 1 hour at −20° and 18 hours at ambient temperature then poured onto ice and extracted with ether. The ether extracts were washed with water, dried ($Na_2SO_4$) and reduced to an oil which was distilled to provide the title compound. b.p. 154° (15 mm).

Step 2. D,L-Methyl epsilon-oxo-(5-decylthiophene-2)-hexanoate 2-n-Decylthiophene (2 g) and methyl 5-(chloroformyl)penanoate (1.58 g) in benzene (15 ml) was cooled to 0° under $N_2$ atmosphere and stannous chloride ($SnCl_4$) (2.29 g) was added dropwise to the stirred mixture. After 30 minutes the mixture was poured onto ice-brine mixture and extracted with ether. The organic extracts were washed with brine, dried ($Na_2SO_4$) and reduced to dryness. The residue recrystallized from methanol gave the title compound, m.p. 43°–44°.

Step 3. D,L-Epsilon-oxo-(5-decylthiophene-2)-hexanoic acid

The ester from Step 2 was hydrolyzed following the procedure described in Example 19 (substituting for an equivalent amount of methyl epsilon-(2-carboxyethylthio)-(4-n-nonylbenzene)-hexanoate) to provide the title compound, m.p. 67°–68°.

Analysis, calculated: C, 68.14; H, 9.15; S, 9.09.
Observed: C, 68.45; H, 9.27; S, 9.16.

Step 4. D,L-Methyl-epsilon-hydroxy-(5-decylthiophene-2)-hexanoate

To the ester from Step 2 (3.3 g) in THF (300 ml) and methanol (150 ml) was added 0.4M $CeCl_3$ in methanol (25 ml) and then portionwise sodium borohydride (8 g). After 10 minutes water (500 ml) was added and the mixture was extracted with ether. The ether extracts were washed with brine, dried ($Na_2SO_4$) and reduced to dryness. Chromatography on silica gel provided the title compound as an oil.

Analysis, calculated: C, 68.44; H, 9.84; S, 8.69.
Observed: C, 68.67; H, 9.75; S, 8.93.

Step 5. D,L-Epsilon-hydroxy-(5-decylthiophene-2)-hexanoic acid

Following the procedure described in Example 19, substituting the ester from Step 4 above for methyl epsilon-(2-carboxyethylthio)-(4-n-nonylbenzene)hexanoate, was obtained the title compound as an oil.

Analysis, calculated: C, 67.75; H, 9.67; S, 9.04.
Observed: C, 66.46; H, 10.06; S, 8.87.

EXAMPLE 39

Preparation of D,L-Methyl epsilon-(butylthio)-5-decyl-2-thiophenehexanoate

Following the procedure described in Example 15, Step 3 but substituting an equivalent amount of methyl epsilon-hydroxy-5-decyl-2-thiophenehexanoate for methyl epsilon-hydroxy-(4-n-nonylphenyl)hexanoate, was obtained the title compound as an oil.

Analysis, calculated: C, 69.31; H, 10.05; S, 12.65.
Observed: C, 68.75; H, 10.22; S, 13.85.

EXAMPLE 40

Preparation of D,L-Epsilon-(butylthio)-5-decyl-2-thiophenehexanoic acid

Following the procedure described in Example 19, but substituting an equivalent amount of the ester from Example 39 for methyl epsilon-(2-carboxyethylthio)-(4-n-nonylphenyl)hexanoate, was obtained the title compound as an oil.

Analysis, calculated: C, 67.19; H, 10.36; S, 14.55.
Observed: C, 67.55; H, 9.92; S, 15.03.

EXAMPLE 41

Preparation of D,L-Methyl epsilon-(phenylthio)-5-decyl-2-thiophenehexanoate

Following the procedure described in Example 39 but substituting an equivalent amount of thiophenol for n-butylmercaptan was obtained the title compound, as an oil.

Analysis, calculated: C, 70.38; H, 8.75; s, 13.92.
Observed: C, 70.49; H, 9.30; s, 13.59.

EXAMPLE 42

Preparation of D,L-Epsilon-(phenylthio)-5-decyl-2-thiophenehexanoic acid

Following the procedure described in Example 19 but substituting an equivalent amount of the ester from Example 41 for methyl epsilon-(2-carboxyethyl)-thio-(4-n-nonylphenyl)hexanoate, was obtained the title compound as an oil.

Analysis, calculated: C, 69.90; H, 8.57; s, 14.36.
Observed: C, 69.65; H, 8.77; s, 13.72.

EXAMPLE 43

Preparation of D,L-Methyl epsilon-((2-aminophenyl)-thio)-5-decyl-2-thiophenehexanoate Following the procedure described in Example 39, but substituting an equivalent amount of 2-aminophenylmercaptan for n-butylmercaptan was obtained the title compound as an oil.

Analysis, calculated: C, 68.16; H, 8.69.
Observed: C, 68.60; H, 9.22.

EXAMPLE 44

Preparation of Epsilon-((2-aminophenyl)thio)-5-decyl-2-thiophenecarboxylic acid monohydrate Following the procedure in Example 19 but substituting an equivalent amount of the ester from Example 42 for methyl epsilon-(2-carboxyethylthio)-(4-n-nonylphenyl)hexanoate, was obtained the title compound as an oil.

Analysis, calcuated: C, 65.09; H, 8.61; s.
Observed: C, 65.68; H, 8.57; s, 12.41.

EXAMPLE 45

Preparation of
D,L-Epsilon-((4-carboxyphenyl)thio)-5-decyl-2-thiophenehexanoic acid Following the procedure described in Example 33 but substituting an equivalent amount of methyl epsilon hydroxy-5-n-decyl-2-thiophenehexanoate for methyl epsilon-hydroxy-(4-n-nonylphenyl)hexanoate was obtained methyl epsilon-((4-methoxycarbonyl)phenyl)-thio)-5-decyl-2-thiophenehexanoate as an oil.

Analysis, calculated: C, 67.14; H, 8.16, s, 12.36.
Observed: C, 67.03; H, 8.41; s, 12.10 and subsequently, the title compound, m.p. 108°–109°.
Analysis, calculated: C, 66.08; H, 7.81; s, 13.06.
Observed: C, 66.14; H, 7.94; 5, 12.23.

EXAMPLE 46

Preparation of
D,L-Methyl-7-(((6-methoxy-6-oxo-1(5-decyl-2-thiophenyl))hexyl)thio)-8-propyl-4-oxo-4H-1-benzopyran-2-carboxylate Following the procedure described in Example 23 but substituting an equivalent amount of methyl epsilon hydroxy-5-n-decyl-2-thiophenehexanoate for methyl epsilon-hydroxy-(4-n-nonylphenyl)hexanoate was obtained the title compound, as an oil. NMR (CDCl$_3$): 0.8–2.3 (3H, m), 2.74 (2H, t), 3.03 (2H, t), 3.65 (3H, s), 4.0 (3H, s), 4.5 (1H, t), 6.55 (2H, m), 7.05 (1H, s), 7.35 (1H, d), 7.90 (1H, d).

EXAMPLE 47

Preparation of
D,L-7-(((5-carboxy-1(5-decyl-2-thiophenyl)pentyl)thio-8-propyl-4-oxo-4H-1-benzopyran-2-carboxylic acid Following the procedure described in Example 19, but substituting an equivalent amount of the diester from Example 46 for methyl epsilon-(2-carboxyethyl-thio)-(4-nonylphenyl)hexanoate and using double the equivalent amount of 0.2N LiOH, was obtained the title compound, as an oil.

EXAMPLE 48

Preparation of
D,L-Erythro-epsilon-((2-carboxyethyl)-thio)-delta-hydroxy-4-nonylbenzenehexanoic acid Following the procedure described in Example 13, but substituting an equivalent amount of 4-n-nonylbenzaldehyde for benzaldehyde in Step 1 gave sequentially.

A. A mixture of E and Z methyl(4-n-nonylphenyl)-delta-hexenoate as an oil: NMR (CDCl$_3$): 0.75–2.0 (19H, m), 2.0–2.7 (6H, m), 3.60 (3H, s), 5.3–6.5 (2H, m), 7.13 (4H, m).

and B. Methyl D,L-(E)-delta, epsilon-epoxy-(4-n-nonylphenyl)hexanoate as an oil: NMR (CDCl$_3$): 0.75–2.0 (21H, m), 2.40 (2H, t), 2.56 (2H, t), 2.95 (1H, dt), 3.55 (1H, d, J=2 HZ), 3.65 (3H, s), 7.15 (4H, m).

and C. Methyl D,L-(Z)-delta, epsilon-epoxy(4-n-nonylphenyl)hexanoate as an oil: NMR (CDCl$_3$): 0.7–1.9 (21H, m), 2.28 (2H, t), 2.60 (2H, t), 3.15 (1H, m), 3.62 (3H, s), 4.00 (1H, d, J=4 HZ), 7.17 (4H, m).

and D. Methyl D,L-erythro-epsilon-((3-methoxy-3-oxo-propyl)thio)-delta-hydroxy-(4-n-nonylphenyl)hexanoate, as an oil: NMR (CDCl$_3$): 0.7–1.9 (21H, m), 2.1–2.7 (9H, m), 3.65 (3H, s), 3.83 (3H, m), 7.16 (4H, q).

and E. The title compound was obtained by treating the diester D, (575 mg) in THF (15 ml) and 0.2N LiOH (15.4 ml), stirred at ambient temperature for 1–5 hours. The mixture was diluted with water (30 ml) acidified with 12N HCl and extracted with CH$_2$Cl$_2$. The organic extracts were washed with brine, dried (Na$_2$SO$_4$), and reduced to dryness to provide the title compound, m.p. 71°–72°.

Analysis, calculated: C, 65.72; H, 8.73; S, 7.31.
Observed: C, 65.37; H, 8.95; S, 7.01.

EXAMPLE 49

Preparation of
D,L-Threo-epsilon-((2-carboxyethyl)thio)-delta-hydroxy-4-nonylbenzenehexanoic acid disodium salt Following the procedure described in example 13, but substituting an equivalent amount of methyl D,L-(Z)-delta, epsilon-epoxy-6-(4-n-nonylphenyl)hexanoate for methyl D,L-(E)-5,6-epoxy-6-phenylhexanoate in Step 3, was obtained sequentially: methyl D,L-threo-delta-hydroxy-epsilon-((3-methoxy-3-oxo-propyl)thio)-(4-n-nonylphenyl) hexanoate as an oil.

Analysis, calculated: C, 66.91; H, 9.09; S, 6.87.
Observed: C, 67.11; H, 9.86; S, 6.62. and the title compound: as an amorphous solid.
Analysis, calculated: C, 59.73; H, 7.52; S, 6.64.
Observed: C, 59.54; H, 8.05; S, 6.38. Also obtained was methyl D,L-threo-delta-((3-methoxy-3-oxopropyl)-thio)-epsilon-hydroxy-(4-nonyl-phenyl)-hexanoate: NMR (CDCl$_3$): 0.7–1.8 (21H, m), 2.20 (2H, m), 2.4–2.9 (7H, m), 3.35 (1H, m), 3.55 (3H, s), 3.63 (3H, s), 4.46 (1H, d), 7.17 (4H, q): and D,L-threo-delta-((2-carboxyethyl)thio)-epsilon-hydroxy-4-nonylbenzene-heptanoic acid disodium salt hemihydrate, as an amorphous solid.

Analysis, calculated: C, 58.63; H, 8.00; S, 6.52.
Observed: C, 58.47; H, 8.04; S, 5.84.

EXAMPLE 50

Preparation of
N-Gamma-L-glutamyl-S-(D,L-erythro-5-carboxy-2-hydroxy-1-(4-nonylphenyl)pentyl-L-cysteinyl glycine trisodium salt trihydrate Following the general procedure described in Example 14, but substituting an equivalent amount of methyl D,L-(E)-delta, epsilon-epoxy-(4-n-nonylphenyl)-hexanoate for methyl D,L-delta, epsilon-epoxy-phenylhexanoate was obtained, after purification of the product from Step 2 on a column of Amberlite XAD-8, as described in Example 24, the title compound. as an amorphous solid.

Analysis, calculated: C, 49.00; H, 6.89; N, 5.53; S, 4.22.
Observed: C, 49.22; H, 7.04; N, 5.37; S, 4.17.

EXAMPLE 51

Preparation of Methyl
D,L-erythro-epsilon-((2(L)-((4(L)-amino-5-methoxy-1,5-dioxopentyl)amino)-3-((2-methoxy-2-oxoethyl)amino)-3-oxopropyl)thio)-delta-hydroxy-4-nonylbenzenehexanoate Methyl D,L-(E)-delta, epsilon-epoxy-(4-n-nonylphenylhexanoate (155 mg) and glutathione dimethyl ester (150 mg) in methanol (3 ml) and triethylamine (0.25 ml) were stirred under N$_2$ atmosphere for 114 hours. The mixture was reduced to dryness and purified by chromatography on silica gel to provide the title compound, as an oil.

NMR (CDCl$_3$): 0.90 (3H, m), 1.0–2.0 (19H, m), 2.0–2.7 (10H, m), 2.80 (2H, m, exchanged by D$_2$O), 3.50 (1H, m), 3.60 (3H, s), 3.72 (6H, s), 3.8–4.2 (4H, m), 4.68 (1H, m), 7.22 (4H, q), 7.4–7.8 (2H, broad m).

EXAMPLE 52

Preparation of D,L-Erythro-delta-hydroxy-epsilon-(methylthio)-4-nonylbenzenehexanoic acid Step 1. Methyl D,L-erythro-delta-hydroxy-epsilon-methylthio-(4-n-nonylphenyl)hexanoate To a solution of methyl D,L-(E)-delta, epsilon-epoxy-(4-n-nonylphenyl)hexanoate (390 mg) in 1,2-dichloroethane (3 ml) was added methylthiotrimethylsilane (135 mg) and anhydrous zinc iodide (60 mg). The mixture was stirred 18 hours at ambient temperature, evaporated to dryness, dissolved in methanol (1 ml) and acetic acid (0.1 ml) and left to stand 2 hours. The mixture was evaporated to dryness and the residue was chromatographed on silica gel to provide the title compound, as an oil.

NMR (CDCl$_3$) 0.85 (3H, m), 1.0–1.8 (18H, m), 1.9 (3H, s), 2.0–2.6 (5H, m), 3.7 (5H, m and s), 7.1 (4H, m).

Step 2. D,L-erythro-delta-hydroxy-epsilon-(methylthio)-4-nonylbenzenehexanoic acid Following the procedure described in Example 19, but substituting an equivalent amount of the ester from Step 1 above for methyl epsilon-((2-carboxyethyl)thio)(4-n-nonylphenyl)hexanoate, was obtained the title compound, as an oil. NMR (CDCl$_3$): 0.85 (3H, m), 1.0–1.8 (18H, m), 1.9 (3H, s), 2.0–2.6 (5H, m), 3.7 (2H, m), 7.1 (5H m).

EXAMPLE 53

Preparation of Methyl D,L-erythro-delta-hydroxy-epsilon-(methylsulfinyl)-4-nonylbenzenehexanoate The ester from Example 52, Step 1, (100 mg) and m-chloroperbenzoic acid (43 mg) were stirred together in CH$_2$Cl$_2$ (2 ml) at 0° for 30 minutes. The mixture was diluted with CH$_2$Cl$_2$ (20 ml), washed with 5% NaHCO$_3$, brine, dried (NaSO$_4$) and evaporated to dryness to provide the title compounds, m.p. 81.5°–82°.

Analysis, calculated: C, 67.26; H, 9.33; S, 7.81.
Observed: C, 67.30; H, 9.69; S, 7.62.

EXAMPLE 54

Preparation of S-((D and L)-erythro-5-carboxy-2-hydroxy-1-(4-nonylphenyl)-pentyl)-L-cysteinylglycine disodium salts Step 1.

A mixture of methyl D,L-(E)-delta, epsilon-epoxy-(4-n-nonylphenyl)hexanoate (550 mg), N-trifluoroacetylcysteinylglycine dimethyl ester (550 mg) and triethylamine (0.89 ml) in anhydrous methanol (5.5 ml) was stirred at ambient temperature under a nitrogen atmosphere 4 days. The mixture was evaporated to dryness and the residue was chromatographed on silica gel to provide the pure diasteriomers (absolute stereochemistry unassigned): delta S, epsilon R (or delta R, epsilon S)-delta-hydroxy-epsilon-S-(N-trifluoroacetyl-cysteinylglycyl)-(4-n-nonylphenyl)hexanoic acid dimethyl ester (less polar isomer): NMR (CDCl$_3$):

0.85 (3H, m), 1.1–2.0 (19H, m), 2.32 (2H, m), 2.5–2.9 (4H, m), 3.62 (3H, s), 3.75 (3H, S), 4.00 (4H, m), 4.6 (1H, m), 7.20 (4H, m), 7.60 (1H, d). and delta R, epsilon S (or delta S, epsilon R)-delta-hydroxy-epsilon-S-(N-trifluoroacetylcysteinylglycyl)-6-(4-n-nonylphenyl)hexanoic acid dimethyl ester (more polar isomer): NMR (CDCl$_3$): 0.87 (3H, m), 1.1–1.9 (19H, m), 2.2–2.9 (6H, m), 3.62 (3H, S), 3.75 (3H, S), 3.95 (4H, m), 4.45 (1H, m), 6.75 (1H, m), 7.20 (4H, m), 7.52 (1H, d).

Step 2.

The less polar diester from Step 1 above (338 mg) was stirred in methanol (2 ml) and 0.2N NaOH (9.4 ml) for 18 hours at ambient temperature. The mixture was concentrated in vacuo to near dryness. diluted with water (5 ml) and applied to a column of Amberlite XAD-8. After standing 1 hour, the column was washed with water until the effluent was neutral pH, then with 95% ethanol. The ethanol washings were reduced to dryness to provide isomer one of the title compounds, as an amorphous solid.

Analysis, calculated: C, 56.30; H, 7.27; S, 5.78.
Observed: C, 56.38; H, 7.76; S, 5.70.

Step 3.

Following the procedure described in Step 2 above, the more polar isomer from Step 1 was converted to isomer 2 of the title compounds, as an amorphous solid, obtained as mono-hydrate. Analysis, calculated: C, 54.52; H, 7.39; S, 5.60. Observed: C, 54.66; H, 7.60; S, 5.16.

EXAMPLE 55

Preparation of D,L-Erythro-7-((5-carboxy-2-hydroxy-1-(4-nonylphenyl)pentyl)thio)-4-oxo-8-propyl-4H-1-benzopyran-2-carboxylic acid disodium salt dihydrate Following the procedure described in Example 54 (Steps 1 and 2) but substituting an equivalent amount of methyl 7-mercapto-4-oxo-8-propyl-4H-1-benzopyran-2-carboxylate for N-trifluoroacetyl cysteinylglycine methyl ester in Step 1 was obtained the title compound, m.p. 215°–230° (decomp).

Analysis, calculated: C, 60.34; H, 6.85; S, 4.74.
Observed: C, 60.55; H, 6.46; S, 5.36.

EXAMPLE 56

Preparation of D,L-erythro-7-((5-carboxy-2-hydroxy-1-(4-nonylphenyl)pentyl)thio-4-oxo-4H-1-benzopyran-2-caraboxylic acid disodium salt trihydrate Following the procedure described in Example 54 (Steps 1 and 2) but substituting an equivalent amount of methyl 7-mercapto-4-oxo-4H-1-benzopyran-2-carboxylate for N-trifluoroacetylcysteinylglycine methyl ester in Step 1, was obtained, sequentially: methyl D,L-erythro-7-((6-methoxy-6-oxo-2-hydroxy-1-(4-nonylphenyl)hexyl)thio-4-oxo-4H-1-benzopyran-2-carboxylate, m.p. 91°–93°.

Analysis, calculated: C, 65.97; H, 7.38; S, 5.33.
Observed: C, 65.83; H, 7.08; S, 4.78. and the title compound, m.p. 250° (decomp.)

Analysis, calculated: C, 57.05; H, 6.48; S; 4.91.
Observed: C, 57.06; H, 6.60; S, 4.18.

EXAMPLE 57

Preparation of
D,L-Threo-7-((5-Carboxy-2-hydroxy-1-(4-nonylphenyl)pentyl)thio)-4-oxo-8-propyl-4H-1-benzopyran-2-carboxylic acid monoammonium salt monohydrate Step 1.

Following the procedure described in Example 55, Step 1, but substituting an equivalent amount of D,L-(Z)-delta,epsilon-epoxy-(4-n-nonylphenyl)hexanoate for D,L-(E)-delta,epsilon-epoxy-(4-n-nonylphenyl)-hexanoate was obtained a product 1 g which was stirred in toluene (5 ml) and trifluoroacetic acid (0.3 ml) for 2 hours. The mixture was evaporated to dryness and chromatographed on silica gel to provide methyl D,L-threo-7-((5-carboxy-2-hydroxy-1-(4-nonylphenyl)-pentyl)thio-4-oxo-8-propyl-4H-1-benzopyran-2-carboxylate, m.p. 73°-75°.

Analysis, calculated: C, 70.92; H, 7.48; S, 5.41.
Observed: C, 70.62; H, 7.60, S, 5.45.

Step 2.

Following the procedure described in Example 54, Step 2, but substituting an equivalent amount of the lactone from Step 1 above, for (delta R,epislons) (or delta S,epsilon R)-delta-hydroxy-epsilon-S-(N-trifluoracetylcysteinylglycyl)-6-(4-n-nonylphenyl)-hexanoic acid dimethyl ester, was obtained a product which was further purified by chromatography on silica gel eluting with methanol:chloroform:12N ammonium hydroxide (4:8:1) to provide the title compound, m.p. 100°-104°.

Analysis, calculated: C, 64.63; H, 7.81; N, 2.22; S, 5.07.
Observed: C, 64.57; H, 7.74; N, 2.66; S, 4.72.

EXAMPLE 58

Preparation of
D,L-Erythro-epsilon-((4-acetyl-3-hydroxyphenyl)thio)-delta-hydroxy-4-nonylbenzenehexanoic acid sodium salt Step 1.

A mixture of the epoxide from Example 48, Step B, (1.44 g), 2-hydroxy-4-mercaptoacetophenone (0.556 g), triethylamine (1.85 ml) and anhydrous methanol (11 ml) was stirred 18 hours under an N$_2$ atmosphere at ambient temperature. The mixture was reduced to dryness and chromatographed on silica gel to provide methyl D,L-erythro-epsilon-((4-acetylhydroxyphenyl)thio)-delta-hydroxy-(4-n-nonylphenyl)-hexanoate as an oil.

Analysis, calculated: C, 70.00; H, 8.23; S, 6.23.
Observed: C, 70.18; H, 8.60; S, 6.01.

Step 2.

The ester from Step 1 (1.07 g) was stirred in THF (28 ml) and 0.2N NaOH (26 ml) for 18 hours at ambient temperature. The mixture was concentrated to remove THF and applied to a column of Amberlite XAD-8. After standing 1 hour, the column was washed with water until the effluent was neutral, then elution with 95% ethanol, and evaporation of the ethanol effluent gave the title compound, as a foam. Analysis, calculated: C, 66.64; H, 7.52; S, 6.13. Observed: C, 66.65; H, 7.81; S, 6.02.

EXAMPLE 59

Preparation of Sodium
(D,L)-epsilon-((4-acetyl-3-hydroxyphenyl)thio)-delta-hydroxy-4-nonylbenzenehexanoate monohydrate Step 1.

A mixture of the epoxide from Example 48, Step B (0.82 g), 2-hydroxy-3-propyl-4-mercaptoacetophenone (0.58 g), triethylamine (1.4 ml) and anhydrous methanol (10 ml) was stirred 18 hours at ambient temperature. The solvents were removed in vacuo and the residue was chromatographed on silica gel to provide D,L-erythro-epsilon-((4-acetyl-3-hydroxy-2-propyl(2-n-propyl-3-phenyl)thio)-deltahydroxy-(4-n-nonylphenyl)hexanoate as an oil Analysis, calculated: C, 71.18; H, 8.69; S, 5.76. Observed: C, 70.93; H, 8.70; S, 5.90.

Step 2.

The ester from Step 1 (0.82 g), THF (16 ml) and 0.2N NaOH (16 ml) was stirred together at ambient temperature for 2 hours. The mixture was treated as described in Example 58, Step 2, to provide the title compound as a foam.

Analysis, calculated: C, 65.95; H, 8.13; S, 5.50.
Observed: C, 66.20; H, 8.20; S, 5.32.

EXAMPLE 60

Preparation of D,L-Erythro-sodium
delta-hydroxyepsilon-((2-hydroxymethyl)-4-oxo-4H-1-benzopyran-7-yl)thio)-4-nonylbenzenehexanoate sesquihydrate Step 1.

A mixture of the epoxide from Example 48, Step B, (0.40 g), 2-hydroxymethyl-4-oxo-7-mercapto-4H-1-benzopyran (0.21 g), methanol (5 ml) and triethylamine (0.14 ml) was stirred together at ambient temperature for 3 days. The mixture was diluted with CH$_2$Cl$_2$, washed with water, 0.01N HCl and brine, then dried (Na$_2$SO$_4$) and evaporated to dryness. The residue was chromatographed on silica gel to provide D,L-erythro-methyl delta-hydroxyepsilon-((2-hydroxymethyl)-4-oxo-4H-1-benzopyran-7-yl)thio-4-nonylbenzenehexanoate, as an oil.

Analysis, calculated: C, 69.28; H, 7.63; S, 5.78.
Observed: C, 69.45; H, 7.59; S, 5.72.

Step 2.

A solution of the ester from Step 1 (0.696 g), THF (10 ml), and 0.2N NaOH (10 ml) was stirred for 5 minutes at ambient temperature. The mixture was treated as described in Example 58, Step 2. The resulting product was further purified by chromatography on C-18 silica gel, eluting with methanol-water, to provide the title compound, as a foam.

Analysis, calculated: C, 63.13; H, 7.18; S, 5.44.
Observed: C, 62.92; H, 6.81; S, 5.38.

EXAMPLE 61

Preparation of
D,L-Erythro-epsilon-((4-acetyl-3-(carboxymethoxy)-phenyl)thio)-delta-hydroxy-4-nonylbenzenehexanoic acid disodium salt Step 1.

A mixture of the epoxide from Example 48, Step B (0.945 g), 2-carbomethoxymethoxy-4-mercaptoacetophenone (0.787 g), triethylamine (1.5 ml) and anhydrous methanol (10 ml) was stirred under $N_2$ atmosphere at ambient temperature for 18 hours. The mixture was concentrated to an oil which was chromatographed on silica gel to provide methyl D,L-erythroepsilon-((4-acetyl-3-(2-methoxy-2-oxoethoxy)phenyl)thio)-delta-hydroxy-4-nonylbenzenehexanoate as an oil.

Analysis, calculated: C, 67.54; H, 7.90; S, 5.46.
Observed: C, 67.84; H, 8.18; S, 5.23.

Step 2.

A mixture of the diester from Step 1 (1.23 g), THF (20 ml) and 0.2N NaOH (26.2 ml) and methanol (1 ml) was stirred 1 hour at ambient temperature. The mixture was treated as described for Example 58, Step 2, to provide the title compound, as a foam.

Analysis, calculated: C, 61.77; H, 6.69; S, 5.32.
Observed: C, 61.93; H, 6.70; S, 5.07.

EXAMPLE 62

Preparation of D,L-Erythro-7-((5-carboxy-2-hydroxy-1-(4-nonylphenyl)pentyl)thio)-2-methyl-2-benzofurancarboxylic acid disodium salt Step 1.

A mixture of ethyl 3-methyl-6-mercapto-2-benzofuran carboxylate (0.61 g), the epoxide from Example 48, Step B, (0.792 g), triethylamine (1.28 ml) and methanol (10 ml) was stirred under $N_2$ atmosphere for 18 hours. The mixture was concentrated to an oil and chromatographed on silica gel to provide D,L-erythro-methyl 6-((2-hydroxy-6-methoxy-1-(4-nonylphenyl)-6-oxohexyl)thio)-3-methyl-2-benzofurancarboxylate, as an oil.

Analysis, calculated: C, 69.68; H, 7.80; H, 5.64.
Observed: C, 69.73; H, 8.27; S, 5.48.

Step 2.

A mixture of the ester from Step 1, (1.09 g), THF (24 ml) and 0.2N NaOH (24 ml) and methanol (1 ml) was stirred at ambient temperature for 18 hours. The mixture reduced to dryness, dissolved in water and treated as described in Example 58, Step 2, to provide the title compound, as a foam.

Analysis, calculated: C, 63.68; H, 6.55; S, 5.48.
Observed: C, 64.43; H, 6.94; S, 5.24.

EXAMPLE 63

Preparation of D,L-Erythro-6-((5-carboxy-2-hydroxy-1-(4-nonylphenyl)pentyl)thio)-2-oxo-2H-1-benzo-pyran-3-carboxylic acid disodium salt sesquihydrate Step 1.

A mixture of the epoxide from Example 48, Step B (0.35 g), methyl 6-mercapto-2-oxo-2H-1-benzopyran-3-carboxylate (0.24 g) and triethylamine (0.1 ml) in methanol (10 ml) was stirred at ambient temperature, under $N_2$ atmosphere for 15 hours. The solvents were removed in vacuo and the residue was purified by chromatography on silica gel to yield D,L-erythro-methyl 6-((2-hydroxy-6-methoxy-1-(4-nonylphenyl)-6-oxohexyl)thio)-2-oxo-2H-1-benzopyran-3-carboxylate, as an oil.

Analysis, calculated: C, 68.01; H, 7.27; S, 5.50.
Observed: C, 68.12; H, 7.33; S, 5.27.

Step 2.

The diester from Step 1 (200 mg) was stirred in THF (10 ml) with 1N NaOH (1.0 ml), under $N_2$ for 18 hours. The mixture was concentrated and then purified on XAD-8 resin as described in Example 58, Step 2, to provide the title compound, m.p. 195° (decomp.).

Analysis, calculated: C, 59.51; H, 6.27; S, 5.12.
Observed: C, 59.74; H, 6.68; S, 5.03.

EXAMPLE 64

Preparation of Sodium (D,L)-erythro-epsilon-(3-aminophenylthio)-delta-hydroxy-(4-nonylphenyl)-hexanoate Step 1.

A mixture of 3-mercaptoanaline (125 mg), the epoxide from Example 48, Step B (346 mg), and triethylamine (0.3 ml) in methanol (10 ml) was stirred at ambient temperature for 18 hours. The solvents were removed in vacuo and the residue was purified by chromatography on silica gel to yield the D,L-erythro-methyl epsilon-(3-aminophenylthio)-1-delta-hydroxy-(4-nonylphenyl)hexanoate.

NMR (CDCl$_3$): 0.8–1.9 (21 H, m), 2.26 (2H, t), 2.60 (2H, t), 3.22 (3H, s, exchanged by D$_2$O), 3.60 (3H, s), 3.90 (1H, m), 4.20 (1H, d), 6.4–7.0 (4H, m), 7.22 (4H, q).

Step 2.

A mixture of the ester from Step 1 (1 g) and 1N NaOH (2 ml) in methanol (10 ml) was stirred at ambient temperature for 18 hours. The mixture was concentrated and purified on XAD-8 resin as described in Example 58, Step 2, to provide the title compound as a viscous oil.

Analysis, calculated: C, 66.45; H, 7.84; N, 2.87; S, 6.57.
Observed: C, 66.22; H, 7.71; N, 2.96; S, 6.85.

EXAMPLE 65

Preparation of Erythro-sodium epsilon-((3-acetylamino)phenyl)thio)-delta-hydroxy-4-nonylbenzenehexanoate Step 1.

A mixture of the amine from Example 64, Step 1, (2 g) and acetic anhydride (2 ml) in pyridine (25 ml) was stirred at ambient temperature for 18 hours. The volatile components were removed in vacuo and the residue was chromatographed on silica gel to provide (D,L)-erythro-methyl epsilon-((3-(acetylamino)phenyl)thio)-delta-hydroxy-4-nonylbenzenehexanoate as an oil.

NMR (CDCl$_3$) 0.87 (3H, m), 1.1–1.8 (18H, m), 1.90 (3H, s), 2.80 (3H, s), 2.25 (2H, m), 2.57 (2H, t), 3.62 (3H, s), 4.31 (1H, d), 5.27 (1H, m), 6.9–7.6 (8H, m), 8.13 (1H, s).

Step 2.

The diacetate from Step 1 was stirred in methanol (25 ml) with 1N NaOH (2 ml) for 18 hours at ambient temperature. The solvents were removed by evaporation and the residue was dissolved in water and purified on a column of XAD-8 resin as described in Example 58, Step 2, to provide the title compound, m.p. 200°.

Analysis, calculated: C, 66.77; H, 7.73 N, 2.68; S, 6.15.
Observed: C, 67.00; H, 7.19; N, 2.70; S, 5.89.

EXAMPLE 66

Preparation of
Erythro-epsilon-((3-((2-carboxyethyl)-amino)phenyl)-
thio)-delta-hydroxy-4-nonylbenzenehexanoic acid
disodium salt

Step 1.

A mixture of the epoxide from Example 48, Step B, (1.5 g), 3-((3-ethoxy-3-oxopropyl)amino)-pehnylmercaptan (1 g) and triethylamine (2 ml) in methanol (30 ml) was stirred 18 hours at ambient temperature. The solvents were removed in vacuo and the residue was chromatographed on silica gel to provide D,L-erythro-methyl epsilon-((3-ethoxy-3-oxopropyl)-(3-amino)-phenyl)thio)-delta-hydroxy-(4-nonylphenyl)hexanoate as an oil.

NMR (CDCl$_3$): 0.70–1.9 (21H, m), 2.23 (2H, t), 2.50 (4H, m), 3.32 (2H, m), 3.58 (3H, s), 3.87 (1H, m), 4.12 (2H, Q), 6.3–7.4 (8H, m).

Step 2.

The diester from Step 1, (1 g) in methanol (50 ml) with 1N NaOH (3 ml) was stirred at ambient temperature 18 hours. Workup as described in Example 58, Step 2, provided the title compound as a gum.

Analysis, calculated: C, 62.80; H, 7.20; N, 2.44; S, 5.59.

Observed: C, 62.62; H, 7.37; N, 2.42; S, 5.76.

EXAMPLE 67

Preparation of
D,L-Erythro-epsilon-((3-((2-carboxyacetyl)amino)-
phenyl)thio)-delta-hydroxy-(4-nonylphenyl)hexanoic
acid disodium salt hemihydrate

Step 1.

D,L-erythio-methyl-epsilon-((3-((3-methoxy-3-oxopropionyl)amino)phenyl)thio-delta-hydroxy-(4-nonylphenyl)hexanoate A mixture of the epoxide (1.5 g) from Example 48, Step B, ethyl-N-(3-thiophenyl)malonamate (1.0 g) (from Example 12), triethylamine (2.1 ml) and methanol (30 ml) was stirred at room temperature for 18 hours under an inert atmosphere. The mixture was concentrated and chromatographed to provide the title compound as an oil.

Analysis, calculated: C, 67.22; H, 7.93; N, 2.44; S, 5.60.

Observed: C, 67.06; H, 8.06; N, 2.36; S, 5.83.

Step 2.

D,L-Erythro-epsilon-((3-((2-carboxyacetyl)-amino)-phenyl)thio)-delta-hydroxy-(4-nonylphenyl)hexanoic acid disodium salt hemihydrate A mixture of the diester (1.7 g) from Step 1, above, 1N sodium hydroxide (7.0 ml) and methanol (30 ml) was stirred at room temperature for 30 minutes. The mixture was concentrated and purified on XAD-8 type resin to provide the title compound, m.p. 162° C. (dec.)

Analysis, calculated: C, 60.38; H, 6.75; N, 2.34; S, 5.37.

Observed: C, 60.34; H, 6.95; N, 2.31; S, 5.54.

EXAMPLE 68

Preparation of the two diastereomeric Erythroepsilon-((3-((carboxyacetyl)amino)phenyl)sulfinyl)-delta-hydroxy-4-nonylbenzenehexanoic acid disodium salts

Step 1.

To a solution of the diester from Example 67, Step 1 (4 g) in dichloromethane (1.4 ml) at 0°, was added m-chloroperbenzoic acid (1.21 g) in CH$_2$Cl$_2$ (100 ml). The mixture was stirred 10 minutes, then calcium hydroxide (3 g) was added, the mixture was stirred 15 minutes, filtered through celite; and the filtrate was evaporated to dryness to yield a residue which was chromatographed on silica gell to yield diastereomer 1 (more polar):

NMR (CDCl$_3$): 0.87 (3H, m), 1.17–1.9 (1H, m), 2.27 (2H, t), 2.60 (2H, t), 3.52 (2H, s), 3.59 (3H, s), 3.79 (3H, s), 4.40 (1H, broad), 4.63 (1H, broad m), 6.4 (1H, d), 7.1 (5H, m), 7.73 (1H, m), 8.1 (1H, broader), 9.91 (1H, s).

and diastereomer 2 (less polar): NMR (CDCl$_3$): 0.87 (3H, m), 1.1–1.9 (18H, m), 2.2–2.7 (4H, m), 3.43 (2H, s), 3.65 (3H, s), 3.82 (3H, s), 4.45 (1H, m), 5.1 (1H, m), 6.9–8.1 (7H, m), 9.35 (1H, s).

Step 2.

The more polar diastereomer (isomer 1) from Step 1 (1 g) was stirred with 1N NaOH (3 ml) and methanol (15 ml) at ambient temperature for 18 hours. Workup as described for Example 58, Step 2, provided one of the title diastereomers, as a hygroscopic monohydrate, m.p. 175°–178°.

Analysis, calculated: C, 57.96; H, 6.64; N, 2.25; S, 5.15.

Observed: C, 58.30; H, 6.88; N, 2.19; S, 5.14.

Step 3.

The less polar diastereomer (isomer 2) from Step 1 (0.8 g) was stirred with 1N NaOH (3 ml) and methanol (50 ml) was stirred at ambient temperature for 18 hours. Workup as described for Example 58, Step 2, provided the other title diastereomer, as a hygroscopic solid, m.p. 175°–178°.

EXAMPLE 69

Preparation of
Erythro-epsilon-((3-((carboxy-methyl)amino)-
phenyl)thio-delta-hydroxy-4-nonylbenzenehexanoic
acid disodium salt monohydrate

Step 1. 3,3'-Dithiodiaminobenzene

To 3-mercaptoanaline (5 g) in methanol (75 ml) at 0° was added hydrogen peroxide (one equivalent). The mixture was stirred 1 hour at ambient temperature, diluted with water, and extracted with ethyl acetate. The extracts were dried (Na$_2$SO$_4$) and the solvents were removed in vacuo to provide the title compound. NMR (CDCl$_3$): 3.6 (2H, exchanged by D$_2$O), 6.35 (1H, dd), 6.6–7.1 (3H).

Step 2.

3,3'-Dithio-bis-(((2-ethoxy-2-oxoethyl)amino)-benzene)

A mixture of the disulfide from Step 1, (4 g), ethylbromoacetate (5.34 g) and diisopropylethylamine (4.14 g) was heated 1 hour at 100°. The mixture was cooled, diluted with water and extracted with ethyl acetate. The extracts were dried (Na$_2$SO$_4$) concentrated to dryness in vacuo and the residue was chromatographed on silica gel to provide the title compound. NMR (CDCl$_3$): 1.24 (3H, t), 3.80 (2H, s), 4.18 (2H, s), 6.40 (1H, dd), 6.7–7.2 (3H, m).

Step 3. N-(2-ethoxy-2-oxoethyl)-3-mercaptoanaline

A mixture of the bis-ester from Step 2 (1.86 g), triphenyl phosphine (1.28 g), dioxane (3 ml) and water (2 ml) was stirred at 40° under $N_2$ atmosphere for 2 days. The mixture was evaporated to dryness and the residue was purified by chromatography on silica gel to provide the title compound. NMR ($CDCl_3$): 1.24 (3H, t, 3.36 (1H, s), 3.88 (2H, s), 4.20 (2H, q), 6.2–7.1 (4H, m).

Step 4.

Erythro-epsilon-((3-((carboxymethyl)amino)-phenyl)-thio)-delta-hydroxy-4-nonylbenzenehexanoic acid disodium salt monohydrate Following the procedure described in Example 66, a mixture of the epoxide from Example 47, Step B, (1.23 g), N-(2-ethoxy-2-oxoethyl)-3-mercapto)analine (0.8 g) and triethylamine (2 ml) was converted to a diester which after hydrolysis, ((1.05 g) diester, 1N NaOH (1 ml) and methanol (25 ml)) gave the title compound as a gum.

Analysis, calculated: C, 60.30; H, 7.10; N, 2.42; S, 5.55.

Observed: C, 59.91; H, 7.06; N, 2.24; S, 5.66.

EXAMPLE 70

Preparation of Erythro-epsilon-((3-((carboxymethyl)-formylamino)-phenyl)thio)-delta-hydroxy-4-nonylbenzenehexanoic acid disodium salt Step 1.

A mixture of the epoxide from Example 48, Step B, (0.60 g), 3-mercapto-N-formyl-N-(2-ethoxy-2-oxoethyl-)analine (0.70 g) and triethylamine (1.4 ml) in methanol (25 ml) was reacted following the procedure described in Example 66, to provide D,L-erythro methyl-epsilon-((3-((2-methoxy-2-oxoethyl)formylamino)phenyl)thio)-delta-hydroxy-(4-nonylphenyl)hexanoate, as an oil; NMR ($CDCl_3$): 0.7–1.8 (22H, m), 2.30 (2H, m), 2.58 (2H, m), 3.61 (3H, s), 3.70 (3H, s), 4.00 (1H, m), 4.27 (1H, d), 4.35 (2H, s), 7.2 (8H, m), 8.32 (1H, s).

Step 2.

The diester from Step 1 (0.8 g), 1N NaOH (3 ml) and methanol (25 ml) was reacted following the procedure described in Example 58, Step 2, to provide the title compound, m.p. 270° (decomp.)

Analysis, calculated: C, 61.31; H, 6.68; N, 2.38.
Observed: C, 61.08; H, 7.60; N, 2.06

EXAMPLE 71

Preparation of Erythro-epsilon-((3-((carboxyacetyl)amino)phenyl)sulfonyl)-delta-hydroxy-4-nonylbenzenehexanoic acid disodium salt trihydrate Step 1.

To a solution of the diastereomer 1 from Example 68, Step 1 (1 g) in $CH_2Cl_2$ (50 ml) was added m-chloroperbenzoic acid (0.3 g) and the mixture was stirred 18 hours at ambient temperature. The mixture was concentrated and the residue was chromatographed on silica gel to provide erythromethyl epsilon-((3-((2-methoxy-2-oxoethyl)amino)phenyl)sulfonyl)-delta-hydroxy-4-nonyl-benzenehexanoate as an oil:

NMR ($CDCl_3$): 0.7–1.9 (21H, m), 2.27 (2H, m), 2.52 (2H, m), 3.50 (2H, s), 3.60 (3H, s), 3.77 (3H, s), 4.10 (1H, d), 4.74 (1H, m), 5.48 (1H, broad), 6.9–7.6 (7H, m), 7.7–8.2 (3H, m), 9.37 (1H, s).

Step 2.

The diester from Step 1 (0.8 g), 1N NaOH (3 ml) and methanol (50 ml) were reacted following the procedure described in Example 58, Step 2, to provide the title compound as a hygroscopic solid, m.p. 175°–180°.

Analysis, calculated: C, 53.49; H, 6.68; N, 2.07; S, 4.76.
Observed: C, 53.02; H, 6.46; N, 2.07; S, 5.00.

EXAMPLE 72

Preparation of Erythro-sodium epsilon-((4-aminophenyl)thio)-delta-hydroxy-4-nonylbenzenehexanoate hemihydrate Step 1.

A mixture of 4-mercaptoanaline (250 mg) the epoxide from Example 48, Step B (700 mg) and triethylamine (0.5 ml) in methanol (15 ml) was stirred at ambient temperature for 18 hours. The solvents were removed in vacuo and the residue was purified by chromatography on silica gel to provide D,L-erythro-methyl epsilon-((4-aminophenyl)thio)-delta-hydroxy-(4-nonylphenyl)hexanoate.

NMR ($CDCl_3$): 0.8–1.9 (2H, m), 2.22 (2H, t), 2.59 (2H, t), 3.56 (3H, s), 3.5–4.1 (5H, m), 6.48 (2H, d), 7.10 (6H, m).

Step 2.

A mixture of the ester from Step 1 (1 g) and 1N NaOH (2 ml) in methanol (20 ml) was stirred at ambient temperature of 18 hours. The mixture was concentrated and purified on XAD-8 resin as described in Example 58, Step 2, to provide the title compound, m.p. 180°–200°.

Analysis, calculated: C, 66.70; H, 8.00; N, 2.81; S, 6.68.
Observed: C, 66.37; H, 8.04; N, 2.86; S, 6.56.

EXAMPLE 73

Preparation of D,L-Erythro-sodium epsilon-((4-acetylamino)phenylthio)-delta-hydroxy-(4-nonylphenyl)hexanoate Step 1.

A mixture of the amine from Example 72, (Step 1) (1 g) and acetic anhydride (1 ml) in pyridine (20 ml) was stirred at ambient temperature for 18 hours. The volatile components were removed in vacuo and the residue was chromatographed on silica gel to provide D,L-erythromethyl deltaacetoxy-epsilon-((4-(acetylamino)-phenyl)thio)-(4-nonylphenyl)hexanoate, which was used directly in the next step.

Step 2.

The diacetate from Step 1 (1 g) was stirred in methanol (10 ml) and 1N NaOH (2 ml) for 18 hours. The solvents were removed by evaporation and the residue was dissolved in water and purified on a column of XAD-8 resin as described in Example 58, Step 2, to provide the title compound, m.p. 124°–130°.

Analysis, calculated: C, 66.71; H, 7.72; N, 2.68; S, 6.15.
Observed: C, 66.24; H, 8.18; N, 3.23; S, 6.00.

EXAMPLE 74

Preparation of
D,L-Erythro-epsilon-((4-((carboxyacetyl)amino)-phenyl)thio)-delta-hydroxy-(4-nonylphenyl)hexanoic acid disodium salt Step 1.
4-((3-oxo-3-ethoxypropionyl)amino)phenylmercaptan.

A mixture of 4-aminophenylmercaptan (3 g) and diethyl malonate (15 ml) was heated at 165° for 3 hours. The mixture was cooled and chromatographed on silica gel to provide the title compound, m.p. 69°.

Analysis, calculated: C, 55.21; H, 5.47; N, 5.85; S, 13.40.

Observed: C, 55.30; H, 4.91; N, 5.56; S, 13.29.

Step 2.

A mixture of the thiol from Step 1 (1 g), the epoxide from Example 48, Step B (1.45 g) and triethylamine (1 ml) in methanol (25 ml) was stirred under an $N_2$ atmosphere, at ambient temperature for 18 hours. The mixture was evaporated to dryness and the residue was chromatographed on silica gel to provide D,L-erythromethyl epsilon-((4-((3-oxo-3-ethoxypropionyl)amino)-phenyl)thio)-delta-hydroxy-(4-nonylphenyl)hexanoate as an oil.

NMR (CDCl$_3$): 0.87 (3H, m), 1.2–2.9 (22H, m), 2.27 (2H, m), 2.57 (2H, 5), 3.43 (2H, s), 3.60 (3H, s) 3.88 (1H, m), 4.2 (3H, m), 7.27 (8H, m), 9.25 (1H, s).

Step 3.

A mixture of the diester from Step 2 (1.5 g), in NaOH (2 ml) in methanol (10 ml) was stirred at ambient temperature for 18 hours. The mixture was reduced to dryness, the residue was dissolved in water and purified on a column of XAD-8 resin as described in Example 58, Step 2, to provide (D,L)-erythro-epsilon-((4-((carboxyacetyl)amino)phenyl)thio)-delta-hydroxy-(4-nonylphenyl)hexanoic acid disodium salt, m.p. 150°.

Analysis, calculated: C, 61.31; H, 6.69; N, 2.38; s, 5.45.

Observed: C, 61.19; H, 6.63; N, 2.77; S, 5.63.

EXAMPLE 75

Preparation of (D,L)-Erythro-sodium epsilon-((2-aminophenyl)thio)-delta-hydroxy-(4-nonylbenzene)hexanoate monohydrate Step 1.

A mixture of the epoxide from Example 48, Step B, (1.38 g), 2-mercaptoanaline (0.5 g) and triethylamine was stirred together for 18 hours at ambient temperature. The solvents were removed by evaporation in vacuo and the residue was purified by chromatography on silica gel o provide D,L-erythromethyl epsilon-((2-aminophenyl)thio)-delta-hydroxy-(4-nonylbenzene)-hexanoate.

NMR (CDCl$_3$): 0.90 (3H, m), 1.1–1.9 (18H, m), 2.21 (2H, t), 2.59 (2H, t), 3.60 (3H, s), 3.80 (4H, m, 3H exchange by D$_2$O), 4.04 (1H, d), 6.7 (2H, m), 7.25 (6H, m).

Step 2.

A mixture of the ester from Step 1 (1 g) and 1N NaOH (2 ml) in methanol (20 ml) was stirred 18 hours at ambient temperature. The solvents were removed in vacuo and the residue was purified on XAD-8 resin as described in Example 58, Step 2, to provide the title compound. m.p. 150°.

Analysis, calculated: C, 65.17; H, 8.10; N, 2.81; S, 6.44.

Observed: C, 65.50; H, 8.23; N, 2.84; S, 6.31.

EXAMPLE 76

Preparation of
D,L-Erythro-sodium-epsilon-(((2-acetylamino)phenyl)-thio)-delta-hydroxy-(4-nonylbenzene)hexanoate The ester from Example 75, Step 1, (1 g) and acetic anhydride (0.22 ml) in pyridine (10 ml) was stirred 18 hours at ambient temperature. The mixture was reduced to dryness in vacuo and the residue was dissolved in methanol (10 ml) and 1N NaOH (2 ml) and stirred 18 hours at ambient temperature. The solvents were removed in vacuo and the residue was purified on XAD-8 resin as described in Example 58, Step 2, to provide the title compound.

Analysis, calculated: C, 66.63; H, 7.01; N, 2.63; S, 5.83.

Observed: C, 66.76; H, 7.72; N, 2.68; S, 6.15.

EXAMPLE 77

Preparation of
D,L-Erythro-epsilon-((2-((2-carboxyacetylamino)-phenyl)thio)-delta-hydroxy-(4-nonylphenyl)hexanoic acid disodium salt dihydrate A mixture of the ester from Example 75, Step 1 (2 g) and diethylmalonate (100 ml) was heated at 165°, under an atmosphere of $N_2$ for 3 days. The mixture was cooled and chromatographed on silica gel, eluting with hexane to remove unreacted diethyl malonate and then with hexane-10% ethyl acetate to provide a mixture of D,L-erythro-methyl-epsilon-((2-((3-oxo-3-ethoxypropionyl)amino)phenyl)thio)-deltahydroxy-4-nonylphenyl)hexanoate and its corresponding delta-lactone which was dissolved in methanol (20 ml) and 1N NaOH (3 ml) and stirred 18 hours at ambient temperature. The solvents were removed in vacuo and the residue was purified on XAD-8 resin as described in Example 58, Step 2, to provide the title compound, m.p. 130°–140°.

Analysis, calculated: C, 57.78; H, 6.94; N, 2.24; S, 5.14.

Observed: C, 57.75; H, 6.84; N, 2.02; S, 5.38.

EXAMPLE 78

Preparation of
Erythro-7-((5-carboxy-2-hydroxy-1-(4-nonylphenyl)-pentyl)thio-2-naphthalenecarboxylic acid disodium salt Step 1. Methyl 7-[dimethylaminothioxomethoxy)-naphthalene-2-carboxylate Sodium hydride (1.425 g) and methyl 7-hydroxynaphthalene-2-carboxylate (6.0 g) in dimethylformamide (200 ml) were stirred at 0° under nitrogen atmosphere for 1.5 hours. N,N-dimethylthiocarbamylchloride (11.0 g was added and the mixture was heated at 80° for 54 hours. The mixture was cooled, diluted with water (200 ml) and the resulting crystals were collected by filtration and dried to provide the title compound, m.p. 124.5°–126°.

Step 2. Methyl 7-((dimethylamino)carbonyl)thionaphthalene-2-carboxylate

The product from Step 1 above (4.0 g) was dissolved in Dow Therm (biphenyl and diphenyl ether 26:74) (100 ml) and heated at 250° for 6 hours. The mixture was cooled and chromatographed on silica gel to provide the title compound, m.p. 123°–124°.

Step 3. 7-Mercaptonaphthalene-2-carboxylic acid

The ester from Step 2 (4.0 g) was refluxed in methanol (100 ml) and 3N NaOH (27 ml) for 4 hours under an atmosphere of nitrogen. The methanol was then removed by evaporation. The mixture was next diluted with water (10 ml) and acidified with 1N HCl. The resulting crystals were collected by filtration, washed with water and air dried to provide the title compound, m.p. 211°–216°.

Step 4. Methyl 7-mercaptonaphthalene-2-carboxylate

The acid from Step 3 was dissolved in methanol-10% HCl and after 2 hours, the solvents were removed in vacuo to provide the title compound. NMR (CDCl$_3$): 3.90 (3H, s), 4.01 (1H, S, SH), 7.37 (1H, dd), 7.6–7.8 (3H, m), 7.90 (1H, dd), 8.37 (1H, d).

Step 5. D,L-Erythro-methyl-7-((6-methoxy-6-oxo-2-hydroxy-1-(4-nonylphenyl)hexyl)thio)-2-naphthalene carboxylate A mixture of the ester from Step 4 (1 g), the epoxide from Example 48, Step B (1.59 g) and triethylamine (2 ml) in methanol (30 ml) was stirred 48 hours at ambient temperature. The solvents were removed by evaporation and the residue was chromatographed on silica gel to provide the title compound as an oil.

NMR (CDCl$_3$): 0.7–1.8 (21H, m), 2.30 (2H, t), 2.56 (2H, t), 3.60 (3H, 57, 3.95 (4H, S and m), 4.32 (1H, d), 7.0–8.05 (9H, m), 8.45 (1H, S).

Step 6. Erythro-7-((5-carboxy-2-hydroxy-1-(4-nonylphenyl)pentyl)thio)-2-naphthalenecarboxylic acid disodium salt The diester from Step 5 (0.8 g) was stirred with methanol (25 ml) and 1N NaOH (2 ml) at ambient temperature for 24 hours. Concentration to remove methanol and purification on XAD-8 resin (as described in Example 58, Step 2) provided the title compound, m.p. 330°.

Analysis, calculated: C, 66.08; H, 6.68; S, 5.35.
Observed: C, 66.19; H, 6.59; S, 5.52.

EXAMPLE 79

Preparation of Erythro-6-((5-carboxy-2-hydroxy-1-(4-n-nonylphenyl)pentyl)thio)naphthalene-2-carboxylic acid disodium salt pentahydrate

Step 1. Ethyl 6-((dimethylamino)thioxomethoxy)-2-naphthalene carboxylate

A mixture of ethyl 6-hydroxy-2-naphthalene carboxylate (3 g) and sodium hydride (0.5 g) in dimethyl formamide (22.6 ml) was stirred at 0° under an N$_2$ atmosphere for 1.5 hours. N,N-dimethylthiocarbamylchloride (2.06 g) was added and the mixture was stirred 3 hours at 80° C. The mixture was cooled, diluted with dichloromethane and washed with excess aqueous ammonium chloride. The organic phase was dried, reduced to dryness in vacuo and the residue was chromatographed on silica gel to provide the title compound, m.p. 128°–130°.

Analysis, calculated: C, 63.34; H, 5.65; N, 4.62; S, 10.57.
Observed: C, 63.01; H, 5.65; N, 4.78; S, 10.32.

Step 2. 6-((Ethyl 6-((dimethylamino)carbonylthionaphthalene-2-carboxylate

The ester from Step 1 (2.1 g) was heated. neat, at 200° under N$_2$ atmosphere for 2 days. The residue was recrystallized from ethanol to provide the title compound, m.p. 145°–146°.

Step 3. 6-Mercapto-2-naphthalene carboxylic acid

The ester from step 3 (0.65 g) was added to a solution of sodium (0.2 g) in absolute methanol (50 ml). The mixture was stirred 2 hours at ambient temperature, poured into water (100 ml), acidified with concentrated HCl, and the resulting crystals were collected by filtration and dried in air to provide the title compound. NMR (DMSO-d$_6$): 3.4 (1H, broad, changed by D$_2$O), 7.6–8.2 (6H, 1H exchanged by D$_2$O), 8.60 (1H, m).

Step 4. Methyl 6-mercapto-naphthalene-2-carboxylate

The acid from step 3 (0.28 g) was dissolved in anhydrous methanol and the solution was saturated with HCl (gas). After 2 hours the volatile components were removed in vacuo and chromatography of the residue on siica gel provided the title compound, m.p. 150°–151°.

Step 5. D,L-Erythro-methyl 6((6-methoxy-6-oxo-2-hydroxy-1-(4-nonylphenyl)hexyl-thio)-naphthalene-2-carboxylate A mixture of the ester from Step 4 (0.35 g) and the expoxide from Example 48, Step B (0.56 g) in methanol (4 ml) and triethylamine (0.9 ml) was stirred at ambient temperature, under an N$_2$ atmosphere, for 18 hours. The solvents were removed in vacuo and the residue was chromatographed on silica gel to provide the title compounds as an oil.

NMR (CDCl$_3$): 0.7–1.8 (21H, m), 2.27 (2H, t), 2.52 (2H, t), 3.56 (3H, s), 3.89 (4H, s, and m), 4.37 (1H, d), 7.0–8.1 (9H, m), 8.45 (1H, s).

Step 6. Erythro-6-((5-carboxy-2-hydroxy-1-(4-n-nonylphenyl)pentyl)thio)naphthalene-2-carboxylic acid disodium salt pentahydrate The diester from Step 5 (0.22 g) was dissolved in methanol (5 ml) and 1N NaOH (0.78 ml) and stirred one hour at ambient temperature. Concentration to remove the methanol and purification of the aqueous solution on XAD-8 resin (as described in Example 58, Step 2) provided the title compound, m.p. 270°.

Analysis, calculated: C, 57.30, H, 7.19; S, 4.78.
Observed: C, 57.32; H, 7.41; S, 5.00.

EXAMPLE 80

Preparation of Erythro-(D,L)-sodium epsilon-(2-((((4-chlorophenyl)methyl)amino)carbonyl)-phenyl)thio-deltahydroxy-(4-nonylbenzene)hexanoate

Step 1. D,L-Erythro-methyl epsilon-(2-((((4-chlorophenyl)methyl)amino)carbonyl)-phenyl)thiodelta-hydroxy(4-nonylphenyl)hexanoate A mixture of the thiol from Example 3 (440 mg) and the epoxide from Example 48, Step B (625 mg) in methanol (5 ml) and triethylamine (0.86 ml) was stirred at ambient temperature under an $N_2$ atmosphere for 18 hours. The volatile components were removed by evaporation and the residue was chromatographed on silica gel to provide the title compound, as an oil.

Analysis, calculated: C, 69.26; H, 7.43; N, 2.24; S, 5.14.

Observed: C, 69.42; H, 7.40; N, 2.27; S, 5.19.

Step 2. Erythro-sodium epsilon-(2-((((4-chlorophenyl)methyl)amino)carbonyl-phenyl)thiodelta-hydroxy(4-nonylbenzene)hexanoate A mixture of the ester from Step 1 (780 mg), methanol (10 ml) and 1N NaOH (1.3 ml) was stirred at ambient temperature under $N_2$ atmosphere, for 18 hours. The mixture was concentrated to remove methanol and purified on XAD-8 resin as described in Example 58, Step 2, to provide the title compound, m.p. 78°–85°.

Analysis, calculated: C, 66.49; H, 6.86; N, 2.22; S, 5.07.

Observed: C, 66.27; H, 6.54; N, 2.05; S, 4.88.

EXAMPLE 81

Preparation of (+)-Erythro-2-methoxy-7-((5-carboxy-2-hydroxy-1-(4-nonylphenyl)pentyl)thio)-3-quinolinecarboxylic acid

Step 1. Methyl (±)-erythro-5-hydroxy-6((2-methoxy-3-carbomethoxyquinolin-7-yl)thio)-6-(4-methyl-nonylphenyl)hexanoate A mixture of methyl 7-mercapto-2-methoxy-3-quinoline carboxylate (from Example 9) (712 mg) and the epoxide from Example 48, Step B (1.04 g) in methanol (20 ml) and triethylamine (1 ml) was stirred at ambient temperature under argon atmosphere for 54 hours. Solids were removed by filtration and the filtrate reduced to dryness in vacuo. The residue was dissolved in $CH_2Cl_2$ and washed with water, then dried ($MgSO_4$) and evaporated to an oil which was chromatographed on silica gel to provide the title compound as a gum.

Analysis, calculated: C, 68.13; H, 7.45; N, 2.41; S, 5.51.

Observed: C, 68.31; H, 7.68; N, 2.26; S, 5.27.

Step 2.
(+)-Erythro-2-methoxy-7-((5-carboxy-2-hydroxy-1-(4-nonylphenyl)pentyl)thio)-3-quinolinecarboxylic acid A mixture of the diester from Step 1 (9.70 g), methanol (370 ml) and 5N KOH (12.8 ml) was refluxed under argon atmosphere for 2.25 hours. The mixture was concentrated by evaporation in vacuo to 100 ml, then diluted with water (100 ml) and $CH_2Cl_2$ (100 ml). Concentrated HCl (4.7 ml) in water (50 ml) was added the organic phase was separated. The aqueous layer was then extracted with $CH_2Cl_2$ (100 ml). The combined organic extracts were washed with water, dried ($Na_2SO_4$) and evaporated to dryness. The residue was slurried with acetonitrile and the solids were collected by filtration to provide the title compound, m.p. 133°–134°.

Analysis, calculated: C, 67.70; H, 7.30; N, 2.47; S, 5.65.

Observed: C, 67.74; H, 7.31; N, 2.48; 5.75.

EXAMPLE 82

Preparation of D,L-Erythro-5-methyl-2-oxo-1,3-dioxo-4-yl 7-((2-hydroxy-6-((5-methyl-2-oxo-1,3-dioxol-4-yl)methoxy)-1-(4-nonylphenyl)-6-oxohexyl)thio)-2-methoxy-3-quinolinecarboxylate A mixture of the dicarboxylic acid from Example 81, Step 2 (284 mg), 4-bromomethyl-5-methyl-1,3-dioxolenone (200 mg) and $K_2CO_3$ (250 ml) in dimethylformamide (7.5 ml) and hexamethylphosphoramide (0.2 ml) was stirred at 5° for 24 hours. Ether (50 ml) was added and the mixture was washed with water (6×20 ml), then brine and dried over $MgSO_4$. The ether layer was evaporated to dryness and the residue was chromatographed on silica gel to provide the title compound as a gum.

Analysis, calculated: C, 63.70; H, 6.24; N, 1.77; S, 4.05.

Observed: C, 63.87; H, 6.33; N, 1.82; S, 4.03.

EXAMPLE 83

Preparation of (±)-Erythro-2-butoxy-7((5-carboxy-2-hydroxy-1-(4-nonylphenyl)pentyl)thio)-3-quinolinecarboxylic acid

Step 1. Butyl 2-butoxy-7-((5-methoxy-oxomethane-2-hydroxy-1-(4-nonylphenyl)pentyl)thio)-3-quinoline carboxylate A mixture of the epoxide from Example 48, Step B. (3.46 g) and butyl 2-n-butoxy-7-mercapto-3-quinoline carboxylate (3.57 g) in methanol (60 ml) and triethylamine (3.3 ml) was stirred under argon atmosphere at ambient temperature for 48 hours. The mixture was evaporated to dryness and the residue was purified by chromatography on silica gel to provide the title compound, as an oil.

Analysis, calculated: C, b 70.65; H, 8.45; N, 2.06; S, 4.72.

Observed: C, 70.84; H, 9.06; N, 2.37; S, 4.71.

Step 2.

The diester from Step 1 (2.38 g) was dissolved in methanol (100 ml) and 5N KOH (2.5 ml) and the mixture was stirred under argon atmosphere for 2 days. The mixture was refluxed 6 hours, cooled, concentrated to 20 ml, and diluted with water (50 ml). The solution was acidified with 12N HCl, extracted with $CH_2Cl_2$, and the organic extract was washed with water, dried ($MgSO_4$) and evaporated to dryness to provide a solid which, after trituration with acetonitrile, provided the title compound, m.p. 128°–129°.

Analysis, calculated: C, 68.93; H, 7.77; N, 2.30; S, 5.26.

Observed: C, 69.15; H, 7.78; N, 2.17; S, 5.01.

EXAMPLE 84

Preparation of D,L-Erythro-sodium delta-hydroxyepsilon-((3-((3-hydroxy-1-oxopropyl)amino)phenyl)thio)-4-nonyl-benzenehexanaote

Step 1.
3-((3-Hydroxy-1-oxopropyl)amino)phenylmercaptan

A mixture of β-propiolactone (160 mg), and 3-aminophenylmercaptan (250 mg) in acetonitrile (3 ml) was stirred at 45° under argon for 4 days. The mixture was reduced to dryness and chromatographed on silica gel to provide the title compound, m.p. 103°–104°.

Analysis, calculated: C, 54.80; H, 5.62; N, 7.10; S, 16.25.

Observed: C, 54.88; H, 5.70; N, 7.28; S, 16.25.

Step 2. D,L-Erythro-methyl delta-hydroxy-epsilon-((3-((3-hydroxy-1-oxopropyl)amino)phenyl)thio)-4-nonylbenzenehexanoate A mixture of the thiol from Step 1 (591 mg) and the epoxide from Example 48, Step B (1.038 g) in methanol (20 ml) and triethylamine (1 ml) was stirred at ambient temperature under argon for 48 hours. The mixture was evaporated to dryness and the residue was chromatographed on silica gel to provide the title compound as an oil.

Analysis, calculated: C, 68.56; H, 8.34; N, 2.58; S, 5.90.

Observed: C, 68.24; H, 8.28; N, 2.76; S, 5.64.

Step 3.

The ester from Step 2 (471 mg) was stirred in methanol (4 ml) and 5N KOH (0.8 ml) under argon at ambient temperature for 2 hours. The mixture was acidified with 0.5N HCl and extracted with CH$_2$Cl$_2$. The organic extracts were reduced to dryness and redissolved in 0.5N NaOH (2 ml). The solution was applied to a column of XAD-8 resin and after standing 1 hour the column was washed with water (1.25 l). Elution with ethanol provided (after removal of the solvents in vacuo) the title compound, m.p. 88°–89°.

Analysis, calculated: C, 65.31; H, 7.67; N, 2.54; S, 5.81.

Observed: C, 65.10; H, 7.79; N, 2.58; S, 5.75.

EXAMPLE 85

Preparation of Epsilon-D,L-erythro-((3-(cyanoacetylamino)phenyl)thio)-delta-hydroxy-4-nonylbenzenehexanoic acid sodium salt

Step 1. 3-((Cyanoacetyl)aminophenylmercaptan

A mixture of 3-mercaptoaniline (3.25 g) and ethyl cyanoacetate (22 ml) was heated under nitrogen at 165°–170° for 4 hours. The excess ethyl cyanoacetate was removed by evaporation at 0.1 torr at 140°. The residue was dissolved in ethyl acetate, filtered and chromotographed on silica gel to provide the title compound m.p. 198°–201°.

Step 2. D,L-Erythro-methyl epsilon((3-(cyanoacetylamino)phenyl)thio)delta-hydroxy-4-nonylbenzenehexanoate A mixture of the thiol from Step 1 (384 mg) and the epoxide from Example 48, Step B (692 mg) was stirred in methanol (10 ml) and triethylamine (1.27 ml) under argon, at ambient temperature for 48 hours. The volatile solvents were removed by evaporation and the residue was chromatographed on silica gel to provide the title compound as an oil.

Analysis, calculated: C, 69.11; H, 7.86; N, 5.20; S, 5.95.

Observed: C, 69.01; H, 7.81; N, 5.61; S, 5.74.

Step 3. Epsilon-(D,L)-erythro-((3-(cyanoacetyl)-amino)-phenyl)thio)-delta-hydroxy-4-nonylbenzenehexanoic acid sodium salt The ester from Step 2 (492 mg) was stirred in methanol (4 ml) and 5N KOH (0.8 ml) for 4 hours. The solution was diluted with water, acidified with 2N HCl, and extracted with CH$_2$Cl$_2$. The organic extracts were reduced to dryness by evaporation and the residue was dissolved in water (25 ml) and 2N NaOH (1 ml) and the solution was purified on XAD-8 resin as described in Example 58, Step 2, to provide the title compound, m.p. 104°–7°.

Analysis, calculated: C, 65.91, H, 7.19; N, 5.12; S, 5.86.

Observed: C, 65.91; H, 6.88; N, 4.60; S, 5.71.

EXAMPLE 86

Preparation of D,L-Erythro-delta-hydroxy-epsilon-(((5-hydroxy-4-oxo-4H-pyran-2-yl)methyl)thio)-4-nonylbenzenehexanoic acid disodium salt

Step 1. 5-t-Butyldiphenylsiloxy-2-hydroxymethyl-4-oxo-4H-pyran)

A mixture of kojic acid (2.84 g) and t-butyldimethylsilylchloride (5.20 ml) in acetonitrile (30 ml) and triethylamine (3 ml) was stirred 1 hour at ambient temperature. The mixture was partitioned between CH$_2$Cl$_2$ and water. The organic phase was dried (Na$_2$SO$_4$) and reduced to dryness. The residue was chromatographed on silica gel to provide the title compound, m.p. 108.5°–109.5°.

Analysis, calculated: C, 69.44; H, 6.36.

Observed: C, 69.57; H, 6.32.

Step 2. t-Butyldiphenylsiloxy-2-bromomethyl-4-oxo-4H-pyran

A mixture of triphenylphosphine (2.28 g), and carbontetrabromide (4.20 g) in anhydrous CH$_2$Cl$_2$ (40 ml) was stirred at 0° under argon for 30 minutes. The alcohol from Step 1 (950 mg) was added and the mixture was stirred at 0° C. for 2 hours. The mixture was filtered, evaporated to dryness and the residue was chromatographed on silica gel to provide the title compound as an oil.

Analysis, calculated: C, 59.59; H, 5.23; Br, 18.02.

Observed: C, 59.57; H, 5.14; Br, 18.30.

Step 3. D,L-Erythro-methyl delta-hydroxy-epsilonmercapto-(4-nonylphenyl)hexanoate A solution of the epoxide from Example 48, Step B (1.60 g) in methanol (20 ml) and triethylamine (1 ml) was saturated with H$_2$S gas. The mixture was stirred at ambient temperature for 24 hours. The mixture was reduced to dryness in vacuo, the residue was dissolved in CH$_2$Cl$_2$ and washed with 5% aqueous acetic acid and water, then dried (N$_2$SO$_4$) and evaporated to give the title compound as an unstable oil which was used directly in the next step.

Step 4. D,L-Erythro-methyl delta-hydroxy-epsilon-(((5-t-butyldiphenylsiloxy-4-oxo-4H-pyran-2-yl)-methyl)thio)-4-nonylbenzenehexanoate To a solution of the sulfide from Step 3 (400 mg) in anhydrous acetonitrile (5 ml) under argon was added anhydrous K$_2$CO$_3$ (276 mg) and then the bromide from Step 2 (443 mg) in acetonitrile (5 ml). After 30 minutes the solution was filtered and evaporated to dryness. The residue was chromatographed on silica gel to provide the title compound as an oil.

Analysis, calculated: C, 71.11; H, 7.87; S, 4.32.
Observed: C, 71.33; H, 7.96; S, 4.50.

Step 5. (D,L-Erythro-delta-hydroxy-epsilon-(((5-hydroxy-4-oxo-4H-pyran-2-yl)methyl)thio)-4-nonylbenzenehexanoic acid disodium salt A mixture of the ester from Step 4 (1.455 g) and tetrabutylammonium fluoride dihydrate (1.0 g) in THF (50 ml) was stirred at 0° for 30 minutes. The mixture was diluted with water (50 ml) and CH$_2$Cl$_2$ (50 ml) and the aqueous layer was adjusted to pH 2 with HCl. The organic phase was separated, dried (Na$_2$SO$_4$) and evaporated to dryness. The residue was dissolved in methanol (50 ml) and 5N NaOH (1.2 ml). The solution was concentrated to near dryness, redissolved in water (20 ml), washed with ether (2×25 ml), concentrated to remove residual ether, and then purified on a column of XAD-8 resin as described in Example 58, Step 2 to provide the title compound.

Analysis, calculated: C, 60.66; H, 6.86; S, 6.20.
Observed: C, 60.72; H, 6.79; S, 6.00.

EXAMPLE 87

Preparation of (+ −)Erythro-epsilon-(3-(carboxymethyl)amino-3-oxo-2-(phenylmethyl)propyl)thio-deltahydroxy-4-nonylbenzenehexanoic acid disodium salt hemihydrate (isomer I and isomer II)

Step 1. (+)-Erythro-methyl delta-hydroxy-epsilon-(3-(2-methoxy-2-oxo-ethyl)amino)-3-oxo-2-(phenylmethyl)propyl)thio)-4-nonyl-benzene hexanoates A mixture of the trans-epoxide (1.94 g) (from Example 48, Step B), D,L,-3-((2-methoxy-2-oxo-ethyl)amino)-3-oxo-2-(phenylmethyl)propane)thiol (1.5 g), triethylamine (2.8 ml) and methanol (40 ml) was stirred at room temperature for 120 hours. The mixture was concentrated and chromatographed to obtain the title compounds; isomer I as an oil and isomer II having m.p. 38°–40° C.

Analysis, calculated: C, 68.48; H, 8.37; N, 2.28; S, 5.22.
Isomer I, Observed: C, 68.35; H, 8.40; N, 2.41; S, 5.27.
Isomer II, observed; C, 68.57; H, 8.46; N, 2.36; S, 5.33.

Step 2. (+ −)-Erythro-epsilon-((3-((carboxymethyl)amino-3-oxo-2-(phenylmethyl)propyl)thio)-delta-hydroxy-4-nonylbenzenehexanoic acid disodium salt hemihydrate (isomer I and isomer II)

A mixture of the di-ester (736 mg) (from Step 1, Isomer I), in sodium hydroxide solution (4.8 ml) and methanol (25 ml) was stirred at room temperature for 30 minutes. The mixture was concentrated and purified on XAD-8 resin to obtain the title compound. (Isomer I) m.p. 200°–201°.

Similarly (661 mg) (from Step 1, Isomer II) gave the title compound (Isomer II) m.p. 226°–227°.

Analysis, calculated: C, 62.04; H, 7.25; N, 2.19; S, 5.01.
Isomer I, Observed: C, 61.96; H, 7.22; N, 2.14; S, 5.06.
Isomer II, Observed: C, 62.21; H, 7.27; N, 2.13; S, 4.98.

EXAMPLE 88

Preparation of Erythro-epsilon-((3-((carboxycarbonyl)amino)phenyl)-thio)-delta-hydroxy-4-nonylbenzenehexanoic acid disodium salt Step 1. Ethyl-2(3-mercaptophenyl)amino-2-oxo-acetate A mixture of 3-aminothiophenol (5.0 g) and diethyl oxalate (40 ml) was heated under a nitrogen atmosphere for 2 hours at 165°–170° C. The mixture was diluted with 500 ml of n-hexane, and the resulting crystals were collected by filtration to provide the title compound.

Analysis, calculated: C, 53.31; H, 4.92; N, 6.21; S, 14.23.
Observed: C, 53.36; H, 4.85; N, 6.21; S, 13.51.

Step 2. Erythro-methyldelta-hydroxy-epsilon-((3-((methoxyoxoacetyl)amino)phenyl)thio)-(4-nonylbenzene hexanoate A mixture of the epoxide (1.5 g), (from Example 48, Step B), the thiol from Step 1 (975 mg), triethylamine (2.1 ml) and methanol (30 ml) was stirred at room temperature for 18 hours under an inert atmosphere. The mixture was concentrated and chromatographed to provide the title compound as an oil.

Analysis, calculated: C, 66.75; H, 7.77; N, 2.51; S, 5.74.
Observed: C, 66.50; H, 7.63; N, 2.62; S, 5.70.

Step 3. Erythro-epsilon-(3-((carboxycarbonyl)amino)phenyl)-thio)-delta-hydroxy-4-nonylbenzenehexanoic acid disodium salt A mixture of the diester from Step 2 (1.5 g), 1N sodium hydroxide (6.0 ml) and methanol (30 ml) was stirred at room temperature for 30 minutes. The mixture was concentrated and purified on XAD-8 resin to provide the title compound, m.p. 215°–220°.

Analysis, calculated: C, 60.71; H, 6.50; N, 2.44; S, 5.58.
Observed: C, 60.33; H, 6.83; N, 2.49; S, 5.60.

EXAMPLE 89

Preparation of D,L-Epsilon-((3-((carboxyacetyl)amino)-phenyl)thio)-4-nonylbenzenehexanoic acid disodium salt Step 1. Methyl epsilon-((3-((3-ethoxy-1,3-dioxopropyl)amino)phenyl)-thio)-4-nonylbenzenehexanoate A mixture of the alcohol from Example 15, Step 2 (2.2 g), the thiol from Example 12 (1.6 g), anhydrous zinc iodide (4.4 g) and methylene chloride (50 ml) was stirred at ambient temperature for 1 hour. The mixture was filtered and the filtrate was washed with 1N sodium bicarbonate (10 ml), dried (Na$_2$SO$_4$), concentrated in vacuo and chromatographed on silica gel to provide the title compound as an oil.

Analysis, calculated: C, 69.56; H, 8.31; N, 2.45; S, 5.62.

Observed: C, 69.49; H, 8.32; N, 2.29; S, 5.83.

Step 2.
D,L-Epsilon-((3-((carboxyacetyl)amino)-phenyl)thio)-4-nonylbenzenehexanoic acid disodium salt A mixture of the diester from Step 1 (2.5 g), 1N sodium hydroxide (10 ml) and methanol (30 ml) was stirred at room temperature for 30 minutes and then heated to reflux for 5 minutes. The mixture was concentrated and purified on XAD-8 resin to provide the title compound, m.p. 174° (dec.).

Analysis, calculated: C, 63.02; H, 6.87; N, 2.45; S, 5.60.

Observed: C, 62.87; H, 7.08; N, 2.35; S, 5.65.

EXAMPLE 90

Preparation of Erythro-epsilon-((3-((2-carboxy-1-oxopropyl)amino)-phenyl)thio)-delta-hydroxy-4-nonylbenzenehexanoate disodium salt monohydrate (mixture of diastereomers)

Step 1.
3-((3-Ethoxy-2-methyl-1,3-dioxopropyl)amino)-phenylmercaptan

A mixture of 3-aminothiophenol (5.0 g) and diethyl 2-methylmalonate (40 ml) was heated under nitrogen for 2 hours at 165°–170° C. The mixture was diluted with diethyl ether (200 ml), washed with 1N HCl (25 ml), water (50 ml), dried (Na$_2$SO$_4$), concentrated and chromatographed on silica gel to provide the title compound, m.p. 73°–75°.

Analysis, calculated: C, 56.89; H, 5.96; N, 5.52; S, 12.65.

Observed: C, 56.88; H, 5.83; N, 5.49; S, 12.87.

Step 2. Erythro-methyl delta-hydroxy-epsilon-((3-((3-methoxy-2-methyl-1,3-dioxopropyl)amino)-phenyl)thio-4-nonylbenzenehexanoate A mixture of the epoxide from Example 48, Step B (1.5 g), the mercaptan from Step 1 above (1.0 g), triethylamine (2.1 ml) and methanol (30 ml) was stirred at room temperature for 18 hours under nitrogen. The mixture was concentrated and chromatographed on silica gel to provide the title compound as an oil.

Analysis, calculated: C, 67.66; H, 8.08; N, 2.39; S, 5.47.

Observed: C, 67.16; H, 8.29; N, 2.49; S, 5.40.

Step 3.
Erythro-epsilon-((3-((2-carboxy-1-oxopropyl)-amino)-phenyl)thio)-delta-hydroxy-4-nonylbenzenehexanoic acid disodium salt monohydrate (mixture of diastereomers)

A mixture of the diester from Step 2, above 2.3 g), 1N sodium hydroxide (12 ml) and methanol (30 ml) was stirred at room temperature for 30 minutes. The mixture was concentrated and purified on XAD-8 resin to provide the title compound, m.p. 155° (dec.)

Analysis, calculated: C, 60.00; H, 6.99; N, 2.26; S, 5.17.

Observed: C, 59.69; H, 6.97; N, 2.24; S, 5.39.

EXAMPLE 91

Preparation of D,L-Erythro-epsilon-((3-((3-carboxyl-1-oxopropyl)amino)phenyl)thio)-delta-hydroxy-4-nonylbenzenehexanoic acid disodium salt sesquihydrate Step 1. Erythro-methyl epsilon-((3-((3-carboxy-1-oxopropyl)amino)phenyl)thio)-delta-hydroxy-4-nonylbenzenehexanoate monohydrate A mixture of the amino derivative from Example 64, Step 1 (2.1 g), succinic anhydride (1.3 g) and pyridine (100 ml) was stirred at room temperature for 18 hours. The mixture was concentrated and chromatographed on silica gel to provide the title compound as an oil.

Analysis, calculated: C, 65.16; H, 8.03; S, 5.43.

Observed: C, 65.32; H, 8.09; S, 5.73.

Step 2.
D,L-Erythro-epsilon-((3-((3-carboxyl-1-oxopropyl)amino)phenyl)thio)delta-hydroxy-4-nonylbenzenehexanoic acid disodium salt sesquihydrate A mixture of the monoester from Step 1, above (2.1 g), 1N sodium hydroxide (15 ml) and methanol (30 ml) was stirred at room temperature for 30 minutes. The mixture was concentrated and purified on XAD-8 resin to provide the title compound, m.p. 145° (dec.)

Analysis, calculated: C, 59.21; H, 7.05; N, 2.22; S, 5.09.

Observed: C, 59.18; H, 7.11; N, 2.18; S, 5.34.

EXAMPLE 92

Preparation of D,L-Epsilon-((3-((carboxyacetyl)aminophenyl)thio)-delta-oxo-4-nonylbenzenehexanoic acid Step 1. D,L-Methyl epsilon-((3-((3-methoxy-1,3-dioxopropyl)amino)-phenyl)thio)-4-nonyl-delta-oxobenzenehexanoate A mixture of the 5-hydroxy derivative from Example 67, Step 1 (1.5 g), pyridinium chlorochromate (2.2 g), anhydrous sodium acetate (430 mg) and methylene chloride (80 ml) was stirred at room temperature for 5 hours. Diethylether (500 ml) was added and the mixture filtered through celite. The filtrate was concentrated and chromatographed on silica gel to provide the title compound, m.p. 44°–46°.

Analysis, calculated: C, 67.45; H, 7.60; N, 2.45; S, 5.62.

Observed: C, 67.12; H, 7.79; N, 2.44; S, 5.78.

Step 2.
D,L-Epsilon-((3-((carboxyacetyl)amino)phenyl)thio)-delta-oxo-4-nonylbenzenehexanoic acid A mixture of the diester from Step 1, above (815 mg), 1N sodium hydroxide (4.0 ml) and methanol (25 ml) was stirred at room temperature for 1 hour. The mixture was concentrated, acidified with 1N hydrochloric acid (10 ml), extracted with diethylether, dried over Na$_2$SO$_4$ and reconcentrated to obtain a residue which, after chromatography on silica gel, provided the title compound, m.p. 88°–91°.

Analysis, calculated: C, 66.51; H, 7.25; N, 2.58; S, 5.91.

Observed: C, 66.64; H, 7.53; N, 2.67; S, 6.04.

EXAMPLE 93

Preparation of
D,L-Erythro-3-((3-(((4-nonylphenyl)-(tetrahydro-6-oxo-2H-pyran-2-yl)methyl)thio)phenyl)-amino)-3-oxopropanoic acid monohydrate An aqueous solution of the disodium salt from Example 91, Step 2 (1.0 g), was acidified with 1N HCl. The mixture was extracted with chloroform, dried over $Na_2SO_4$ and concentrated. The residue was dissolved in acetic acid (25 ml) and heated at 90° C. for 2 hours. The solution was concentrated and chromatographed on silica gel to provide the title compound as an oil.

Analysis, calculated: C, 66.27; H, 7.60; N, 2.57; S, 5.89.

Observed: C, 66.53; H, 7.78; N, 251; S, 6.22.

EXAMPLE 94

Preparation of
D,L-Erythro-epsilon-((3-((carboxyacetyl)methylamino)phenyl)thio)-delta-hydroxy-4-nonylbenzenehexanoic acid disodium salt monohydrate

Step 1. 3-Formylamino-phenylmercaptan

A mixture of 3-aminothiophenol (5.0 g), formic acid (15 ml) and formic acetic anhydride (15 ml) was stirred at room temperature for 3 hours. The mixture was diluted with ethyl acetate (100 ml), washed with brine (2×50 ml), dried ($Na_2SO_4$) and concentrated to provide the title compound as a thick oil.

Analysis, Calculated: C, 54.88; H, 4.61; N, 9.14; S, 20.93.

Observed: C, 54.77; H, 4.75; N, 9.46; S, 20.78.

Step 2. 3-N-methylaminophenylmercaptan

A solution of 3-formylaminophenylmercaptan from Step 1 (4.4 g), in THF (50 ml) was added dropwise to lithium aluminumhydride (5 g) in THF (200 ml). The mixture was refluxed for 2 hours and then decomposed with ammonium chloride solution. The pH mixture was adjusted to pH 7.0 and then extracted with ethyl acetate (2×250 ml). The organic layer was washed with brine, dried over $Na_2SO_4$ and concentrated to provide the title compound as an oil after distillation. b.p. 100° at 0.1 mm. The hydrochloride salt melted at 138°–140°.

Analysis of HCl salt, Calculated: C, 47.86; H, 5.74; N; 7.97; S, 18.25; Cl, 20.18.

Observed: C, 47.97; H, 5.73; N, 8.11; S, 18.06; Cl, 20.03.

Step 3. Methyl erythro-delta-hydroxy-epsilon-(3-((methylamino)-phenyl)thio)-4-nonylbenzenehexanoate A mixture of the epoxide from Example 48, Step B (3.0 g), 3-N-methylaminophenylmercaptan (2.0 g), triethylamine (4.3 ml) and methanol (60 ml) was stirred at room temperature for 18 hours. The mixture was concentrated and chromatographed to provide the title compound as an oil. M+ at 485 m/e was observed in mass spectrum.

Step 4. D,L-Methyl erythro-epsilon-((3-((3-methoxy-1,3-dioxopropyl)methylamino)phenyl)thio)-deltahydroxy-4-nonylphenylhexanoate A mixture of the ester from Step 3 (4.1 g) and dimethylmalonate (20 ml) was heated under nitrogen for 1 hour at 165°–170°. The mixture was chromatographed on silica gel to provide the title compound as an oil.

Analysis, calculated: C, 67.66; H, 8.08; N, 2.39; S, 5.47.

Observed: C, 67.73; H, 8.30; N, 2.34; S, 5.53.

Step 5. D,L-erythro-3-((3-(((4-nonylphenyl)(tetrahydro-6-oxo-2H-pyran-2-yl)methyl)thio)-phenyl)methylamino)-3-oxopropanoic acid monohydrate A mixture of the diester from Step 4 (3.2 g), 1N sodium hydroxide (11 ml) and methanol (50 ml) was stirred at room temperature for 18 hours. The mixture was concentrated and purified on XAD-8 resin to provide the title compound, m.p. 100° (dec.)

Analysis, calculated: C, 60.08; H, 7.00; N, 2.26; S, 5.17.

Observed: C, 59.85; H, 7.41; N, 2.77; S, 4.81.

EXAMPLE 95

Preparation of
D,L-erythro-epsilon-((3-(carboxyacetyl)amino)-phenyl)thio)-delta-hydroxy-4(phenylmethyl)benzenehexanoic acid disodium salt trihydrate

Step 1. Methyl epsilon-oxo-(4-phenylmethyl)benzenehexanoate

Aluminum chloride (15.0 g) was added in portions to an ice-cold mixture of diphenylmethane (8.4 g), monomethyl adipic acid chloride (8.98 g) and methylene chloride (150 ml). The mixture was stirred 30 minutes at ambient temperature and then poured onto ice. The organic phase was separated, washed with water, dried ($MgSO_4$) and evaporated to an oil. Chromatography on silica provided the title compound, as an oil.

Analysis, calculated: C, 77.39; H, 7.14.

Observed: C, 77.47; H, 7.16.

Step 2. Methyl delta-hydroxy-4(phenylmethyl)benzenehexanoate

Sodium borohydride (1.22 g) was added in portions to a solution of the ester from Step 1 (7.95 g) in methanol (100 ml). After 2 hours the mixture was acidified with HCl, diluted with water, and extracted with dichloromethane. The extract was dried ($MgSO_4$) and evaporated to an oil. Chromatography on silica gel provided the title compound as an oil.

Analysis, calculated: C, 76.89; H, 7.74.

Observed: C, 76.59; H, 7.16.

Step 3. (E)-Methyl 4-(phenylmethyl)benzenehex-5-enoate

A mixture of the hydroxy ester from Step 2 (5.755 g), p-toluenesulfonic acid hydrate (0.5 g) and toluene (60 ml) was refluxed under a Dean Stark water separator for 45 minutes. The mixture was cooled, diluted with ether (60 ml), washed with 1N NaOH, brine, dried ($MgSO_4$) and evaporated to an oil. Chromatography on silica gel provided the title compound as an oil.

Analysis, calculated: C, 81.60; H, 7.53.

Observed: C, 81.78; H, 7.61.

Step 4. (E)-Methyl 5,6-epoxy-(4-phenylmethylphenyl)hexanaoate

A mixture of the unsaturated ester from Step 4 (3.256 g) and 85% m-chloroperbenzoic acid (2.25 g) in methylene chloride (200 ml) was stirred at 0° for 4 hours. Calcium hydroxide (4.5 g) was added. The mixture was stirred 20 minutes, filtered, concentrated to an oil, and the residue was chromatographed on silica gel to provide the title compound, as an oil.

Analysis, calculated: C, 77.39; H, 7.14.
Observed: C, 77.17; H, 7.16.

Step 5. Methyl erythro-epsilon-((3-((3-methoxy-1,3-dioxopropyl)amino)phenyl)thio)-delta-hydroxy-4-(phenylmethyl)-benzenehexanoate A mixture of the epoxide from Step 4 (1.0 g), the thiol from Example 12 (770 mg), triethylamine (1.6 ml) and methanol (25 ml) was stirred at room temperature for 18 hours. The mixture was concentrated and chromatographed on silica gel to provide the title compound as an oil.

Analysis, calculated: C, 67.26; H, 6.20; N, 2.61; S, 5.98.
Observed: C, 66.91; H, 6.27; N, 2.62; S, 5.75.

Step 6. D,L-Erythro-epsilon-((3-((carboxyacetyl)amino)-phenyl)thio)-delta-hydroxy-4(phenylmethyl)-benzenehexanoic acid disodium salt trihydrate A mixture of the diester from Step 5 (1.5 g), 1N sodium hydroxide (8.0 ml) and methanol (25 ml) was stirred at room temperature for 30 minutes. The mixture was concentrated and purified on XAD-8 resin to provide the title compound, m.p. 225°–233° (dec.)

Analysis, calculated: C, 55.53; H, 5.49; N, 2.31; S, 5.29.
Observed: C, 56.08; H, 5.26; N, 2.30; S, 5.16.

EXAMPLE 96

Preparation of Erythro-epsilon-((3-((carboxyacetyl)-amino)phenyl)thio)-1,2-dihydro-delta-hydroxy-5-acenaphthalenehexanoic acid disodium salt sesterhydrate Step 1. Methyl 1,2-dihydro-epsilon-oxo-5-acenaphthalene hexanoate To a mixture of 1,2-dihydro-acenaphthene (15.4 g), adipic acid monomethyl ester monoacid chloride (17.8 g) and 1,2-dichloroethane (250 ml) at 0° C. was added, in portions, aluminum chloride (30 g). The mixture was permitted to rise to room temperature over 2 hours, poured onto ice and then extracted with ethyl acetate (1 l) which was then washed with brine, dried over Na$_2$SO$_4$ and concentrated to obtain a residue which after chromatography on silica gel and recrystallization from methanol gave the title compound, m.p. 51°–55°.

Analysis, calculated: C, 77.00; H, 6.80.
Observed: C, 77.66; H, 6.88.

Step 2. Methyl 1,2-dihydro-epsilon-hydroxy-5-acenaphthalenehexanoate

To a mixture of the ketone from Step 1 (20 g) and methanol (500 ml) cooled to 5° C., was added sodium borohydride (4.0 g). The mixture was stirred for 2 hours, concentrated and the residue partitioned between chloroform and water. The chloroform layer was dried over Na$_2$SO$_4$ and concentrated to obtain the title compound as an oil.

Analysis, calculated: C, 76.48; H, 7.43
Observed: C, 76.00; H, 7.49

Step 3. (E)-Methyl 1,2-dihydro-acenaphthenehex-5-enoate

A mixture of the alcohol from Step 2 (22 g), toluene (500 ml) and p-toluenesulfonic acid (0.5 g) was refluxed for 30 minutes and the water produced was collected in a Dean Stark apparatus. The mixture was washed with water, dried over Na$_2$SO$_4$ and concentrated. The residue was chromatographed on silica gel to give the title compound.

Analysis, calculated: C, 81.39; H, 7.19.
Observed: C, 81.43; H, 7.25.

Step 4. (E)-Methyl 1,2-dihydro-delta, epsilon-epoxy(5-acenaphthalene)hexanoate

To a mixture of the trans-olefin from Step 3 (1.0 g), methylene chloride (250 ml) and 1N NaHCO$_3$ (50 ml) was added m-chloroperbenzoic acid (1.1 g). The mixture was stirred for 2 hours and then calcium hydroxide (3.0 g) was added. After stirring for 15 additional minutes, the mixture was filtered and the filtrate concentrated and chromatographed on silica gel to obtain the title compound, m.p. 58°–60°.

Analysis, calculated: C, 77.00; H, 6.80.
Observed: C, 77.13; H, 6.76.

Step 5. D,L-Erythro-methyl epsilon-((3-((3-ethoxy-1,3-dioxopropyl)amino)phenyl)-thio)1,2-dihydro-delta-hydroxy-5-acenaththalenehexanoate A mixture of the epoxide from Step 4 (2.0 g), the thiol from Example 12 (3.2 g), triethylamine (3.0 ml) and methanol (50 ml) was stirred at room temperature for 18 hours under nitrogen. The mixture was concentrated and chromatographed on silica gel to provide the title compound as an oil.

Analysis, calculated: C, 67.26; H, 6.21; N, 2.61; S, 5.98.
Observed: C, 66.82; H, 6.36; N, 2.58; S, 5.99.

Step 6. D,L-Erythro-epsilon-((3-((carboxyacetyl)-amino)-phenyl)thio)-1,2-dihydro-delta-hydroxy-5-acenaphthalenehexanoic acid disodium salt sesterhydrate A mixture of the diester from Step 5 (2.8 g), 1N sodium hydroxide (15 ml) and methanol (50 ml) was heated to 50° C. for 30 minutes. The mixture was concentrated and purified on XAD-8 resin to provide the title compound, m.p. 233° (dec.).

Analysis, calculated: C, 55.66; H, 5.19; N, 2.40; S, 5.50.
Observed: C, 55.45; H, 5.21; N, 2.46; S, 5.56.

EXAMPLE 97

Preparation of Erythro-7-((5-carboxy-1-(1,2-dihydro-5-acenaphthalenyl)-2-hydroxypentyl)thio)-2-methoxy-3-quinolinecarboxylic acid disodium salt trihydrate Step 1. Erythro-methyl 7-((1-(1,2-dihydro-5-acenaphthylenyl)-2-hydroxy-6-oxohexyl)thio)-2-methoxy-3-quinolinecarboxylate hemihydrate A mixture of the epoxide from Example 96, Step 4 (1.0 g), the thiol from Example 9 (880 mg), triethylamine (1.5 ml) and methanol (25 ml) was stirred at room temperature for 18 hours. The mixture was concentrated and chromatographed on silica gel to provide the title compound which was recrystallized from methanol, m.p. 122°–124°.

Analysis, calculated: C, 67.12; H, 5.81; N, 2.52; S, 5.78.

Observed: C, 67.22; H, 6.05; N, 2.41; S, 5.87.

Step 2.
Erythro-7-((5-carboxy-1-(1,2-dihydro-5-acenaphthalenyl)-2-hydroxypentyl)thio-2-methoxy-3-quinolinecarboxylic acid disodium salt trihydrate A mixture of the diester from Step 1, above (825 mg), 1N sodium hydroxide (5 ml) and methanol (50 ml) was refluxed for 3 hours. The mixture was concentrated and purified on XAD-8 resin to provide the title compound, m.p. 255° (dec.)

Analysis, calculated: C, 56.58; H, 5.07; N, 2.27; S, 5.20.

Observed: C, 56.77; H, 4.94; N, 2.09; S, 5.20.

EXAMPLE 98

Preparation of
D,L-Erythro-3-((3-(((1,2-dihydro-5-acenaphthylenyl)-tetrahydro-6-oxo-2H-pyran-2-yl)methyl)-thio)phenyl)amino)-3-oxopropanoic acid sesquihydrate A solution of the disodium salt from Example 96, Step 6 (1.0 g), in water was acidified with 1N HCl. The mixture was extracted with diethylether, dried over Na2SO4 and concentrated to obtain the free acid as an oil which was dissolved in acetic acid (30 ml) and heated at 50°–60° for 2 hours. The mixture was concentrated and the residue chromatographed on silica gel eluting with chloroform:methanol:ammonium hydroxide (8:4:1) as the ammonium salt. Pumping under high vacuum liberated the title compound as the free acid, m.p. 110° C. (dec.)

Analysis, calculated: C, 64.52; H, 5.61; N, 2.78; S, 6.37.

Observed: C, 64.58; H, 6.14; N, 3.66; S, 6.27.

EXAMPLE 99

Preparation of
Erythro-7-((5-carboxy-1-(1,2-dihydro-3-acenaphthylenyl)-2-hydroxypentyl)thio)-2-methoxy-3-quinolinecarboxylic acid disodium salt sesquihydrate Step 1. Methyl epsilon-oxo-1,2-dihydro-3-acenaphthalene hexanoate To a solution of acenaphthalene (30 g) in THF (600 ml) at 0° C. was added 1 molar borane-THF complex (200 ml). The solution was then permitted to stir at room temperature for 2 hours. The mixture was re-cooled to 0° C. and adipic acid monomethyl ester (32 g) in THF (120 ml) was added over 30 minutes. The mixture was stirred at room temperature for 18 hours. Water (100 ml) was added and the mixture concentrated and chromatographed on silica gel to provide the title compound, recrystallized from ethyl acetate/hexane mixture, m.p. 97°–98°.

Analysis, calculated: C, 77.00; H, 6.80.

Observed: C, 76.76; H, 6.71.

Step 2. Methyl epsilon-hydroxy-1,2-dihydro-3-acenaphthalenehexanoate

To a mixture of the ketone from Step 1 (4.9 (g), and methanol (150 ml) cooled to 5° C. was added in portions sodium borohydride (1.5 g). The mixture was stirred for 2 hours, concentrated and the residue partitioned between methylene chloride and water. The methylene chloride layer was dried over Na2SO4, concentrated and the residue was chromatographed on silica to provide the title compound as an oil.

Analysis, calculated: C, 76.48; H, 7.43.

Observed: C, 76.40; H, 7.42.

Step 3. (E)-methyl 1,2-dihydro-3-acenaphthalenedelta-hexenoate

A mixture of the alcohol from Step 2 (4.0 g), benzene (200 ml) and p-toluene-sulfonic acid (250 mg) was refluxed for 15 minutes and the water produced was collected in a Dean Stark apparatus. The mixture was washed with water, dried over Na2SO4, concentrated and chromatographed on silica gel to provide the title compound, m.p. 52°–54°.

Analysis, calculated: C, 81.39; H, 7.19.

Observed: C, 81.58; H, 7.27.

Step 4. (E)-Methyl delta,epsilon-epoxy-1,2-dihydro-3-acenaphthalenehexanoate

A mixture of m-chloroperbenzoic acid (1.8 g), anhydrous potassium fluoride (626 mg) and methylene chloride (100 ml) was stirred at room temperature for 1 hour. The olefin from Step 3 (2.0 g) was added and the mixture stirred for and additional 1.5 hours after which the heterogeneous mixture was filtered. The filtrate was concentrated and the residue chromatographed on silica gel to provide the title compound, m.p. 58°–60°.

Analysis, calculated: C, 77.00; H, 6.80.

Observed: C, 77.10; H, 7.08.

Step 5. Erythro-methyl 7-((1-(1,2-dihydro-3-acenaphthylenyl)-2-hydroxy-6-methoxy-6-oxohexyl)-thio)-2-methoxy-3-quinolinecarboxylate A mixture of the epoxide from Step 4 (770 mg), the thiol from Example 9 (680 mg), triethylamine (1.5 ml) and methanol (25 ml) was stirred at room temperature for 18 hours. The mixture was filtered, concentrated and chromatographed on silica gel to provide the title compound, m.p. 56°–59°.

Analysis, calculated: C, 68.23; H, 5.72; N, 2.56; S, 5.87.

Observed: C, 68.37; H, 5.61; N, 2.43; S, 5.53.

Step 6.
Erythro-7-((5-carboxy-1-(1,2-dihydro-3-acenaphthylenyl)-2-hydroxypentyl)thio)-2-methoxy-3-quinolinecarboxylic acid disodium salt sesquihydrate A mixture of the diester from Step 5 (1.0 (g), 1N sodium hydroxide (7.3 ml) and methanol (40 ml) was refluxed for 3 hours. The mixture was concentrated and purified on XAD-8 resin to provide the title compound, m.p. 255° (dec.)

Analysis, calculated: C, 59.17; H, 4.79; N, 2.37; S, 5.44.

Observed: C, 58.96; H, 4.92; N, 2.15; S, 5.42.

EXAMPLE 100

Preparation of
D,L-Erythro-epsilon-((3-((carboxyacetyl)amino)-phenyl)thio)-delta-hydroxy-4-(2-phenylethyl)benzenehexanoic acid disodium salt dihydrate Step 1: Methyl epsilon-oxo-4-(2-phenylethyl)benzene hexanoate To a mixture of aluminum chloride (40 g) in dichloromethane (250 ml) was added adipic acid monomethylester monoacid chloride (17.8 g). The mixture was stirred for 15 minutes and then 1,2-diphenylethane (18.2 g) was added. The mixture was stirred for 3 hours, poured onto ice, extracted with dichloromethane. The organic extracts were dried over $Na_2SO_4$, concentrated and chromatographed on silica gel to provide the title compound.

NMR ($CDCl_3$) 7.8–8.0 (d, 2H), 6.85–7.5 (m, 7H), 3.65 (s, 3H), 2.65–3.15 (m, 4H), 2.1–2.55 (m, 4H) 1.5–1.95 (m, 4H).

Step 2: Methyl epsilon-hydroxy-4-(2-phenylethyl)benzenehexanoate

To a mixture of the ketoester from Step 1 (12.8 g), in methanol (50 ml) was added sodium borohydride (2.0 g). The mixture was stirred at room temperature for 4 hours, poured into water, extracted with ethyl acetate. The organic phase was washed with brine, dried over $Na_2SO_4$, concentrated and chromatographed on silica gel to provide the title compound, m.p. 56°–58°.

NMR ($CDCl_3$) 6.9–7.4 (m, 9H), 4.45–4.75 (broad, 1H), 3.65 (s, 3H), 2.8–3.1 (s, 4H), 2.1–2.5 (m, 2H), 1.2–2.0 (m, 6H).

Step 3: (E)-Methyl 4-(2-phenethyl)benzenehex-deltaenoate

A mixture of the alcohol from Step 2 (9.0 g), benzene (250 ml) and p-toluenesulfonic acid (250 mg) was refluxed for 30 minutes as the water produced was collected in a Dean Stark apparatus. The mixture was concentrated and chromatographed to obtain the title compound as an oil. NMR ($CDCl_3$) 7.0–7.4 (m, 9H), 5.9–6.5 (m, 2H), 3.65 (s, 3H), 2.9 (s, 4H), 2.05–2.55 (m, 4H), 2.65–2.0 (quartet, 2H).

Step 4: (E)-Methyl delta,epsilon-epoxy-4-(2-phenylethylbenzenehexanoate

To a mixture of the trans olefin from Step 3 (2.93 g), methylene chloride (400 ml) and 1N $NaHCO_3$ (120 ml) was added m-chloroperbenzoic acid (2.4 g). The mixture was stirred for 2 hours and then calcium hydroxide (15 g) was added. After stirring for 15 minutes more, the mixture was filtered and the filtrate concentrated and chromatographed on silica gel to provide the title compound as an oil.

NMR ($CDCl_3$) 7.0–7.4 (m, 9H), 3.65 (s, 3H), 3.5–3.6 (d, 1H), 2.7–3.1 (m, 5H), 2.25–2.6 (m, 2H), 1.55–2.1 (m, 4H).

IR: (Thin film) 1735 $cm^{-1}$ (C=O)

Step 5: Erythro-methyl delta-hydroxy-epsilon-((3-((3-methoxy-1,3-dioxopropyl)amino)phenyl)thio)-4-(2-phenylethyl)benzenehexanoate A mixture of the epoxide from Step 4 (1.1 g), the thiol from Example 12 (811 mg), triethylamine (2.0 ml) and methanol (50 ml) was stirred at room temperature for 18 hours under nitrogen. The mixture was concentrated and chromatographed on silica gel to provide the title compound as an oil.

Analysis, calculated: C, 67.73; H, 6.41; N, 2.54; S, 5.83.

Observed: C, 67.39; H, 6.63; N, 2.44; S, 5.65.

Step 6: Erythro-epsilon-((3-((carboxyacetyl)amino)-phenyl)thio)-delta-hydroxy-4-(2-phenylethyl)-benzenehexanoic acid disodium salt dihydrate A mixture of the diester from Step 5 (1.0 g), 1N sodium hydroxide (7.0 ml) and methanol (30 ml) was stirred at room temperature for 30 minutes. The mixture was concentrated and purified on XAD-8 resin to provide the title compound, m.p. 168°–180°.

Analysis, calculated: C, 57.89; H, 5.52; N, 2.32; S, 5.32.

Observed: C, 57.89; H, 5.19; N, 2.13; S, 5.62.

EXAMPLE 101

Preparation of
Erythro-7-((5-carboxy-2-hydroxy-1-(4-(2-phenylethyl)-phenyl)pentyl)thio)-2-methoxy-3-quinolinecarboxylic acid disodium salt dihydrate Step 1. Erythro-methyl 7-((2-hydroxy-6-methoxy-6-oxo-1-(4-(2-phenylethyl)-phenyl)hexyl)thio)-2-methoxy-3-quinolinecarboxylate A mixture of the epoxide from Example 100, Step 4 (1.1 g), the thiol from Example 9 (923 mg), triethylamine (2.0 ml) and methanol (40 ml) was stirred at room temperature for 18 hours. The mixture was filtered, concentrated and chromatographed on silica gel to provide the title compound as an oil.

Analysis, calculated: C, 69.08; H, 6.15; N, 2.44; 5.58.

Observed: C, 68.62; H, 6.28; N, 2.42; S, 5.53.

Step 2: D,L-Erythro-7-((5-carboxy-2-hydroxy-1-(4-(2-phenylethyl)phenyl)pentyl)thio)-2-methoxy-3-quinolinecarboxylic acid disodium salt dihydrate A mixture of the diester from Step 1 (1.3 g), 1N sodium hydroxide (9.0 ml) and methanol (40 ml) was stirred at room temperature for 18 hours. The mixture was concentrated and purified on XAD-8 resin to provide the title compound, m.p. 247° (dec.).

Analysis, calculated: C, 59.51; H, 5.31; N, 2.23; S, 5.12.

Observed: C, 59.70; H, 4.99; N, 2.23; S, 5.13.

EXAMPLE 102

Preparation of
Erythro-epsilon-((3-((carboxyacetyl)-amino)phenyl)thio)-5,6,7,8-tetrahydro-delta-hydroxy-2-naphthalenehexanoic acid disodium salt sesquihydrate Step 1. Methyl 5,6,7,8-tetrahydro-epsilon-oxo-2-naphthalene hexanoate To a mixture of aluminum chloride (40 g) in dichloromethane (250 ml) was added adipic acid monomethylester monoacid chloride (17.8 g). The mixture was stirred for 15 minutes and then 5,6,7,8-tetrahydronaphthalene (13.2 g) was added dropwise. The mixture was stirred for 3 hours, poured onto ice, extracted with dichloromethane, dried over $Na_2SO_4$ and concentrated to obtain the title compound as an oil.

Analysis, calculated: C, 74.42; H, 8.08.

Observed: C, 74.38; H, 8.17.

Step 2: Methyl Epsilon-hydroxy-5,6,7,8-tetrahydro-2-naphthalenehexanoate

To a mixture of the ketoester from Step 1 (35 g), in methanol (125 ml) was added sodium borohydride (4.0 g) over 20 minutes. The mixture was stirred at room temperature for 4 hours, poured into water, extracted with ethyl acetate, washed with brine, dried over $Na_2SO_4$, concentrated and chromatographed on silica gel to provide the title compound, m.p. 107°–108°.

Analysis, calculated: C, 73.88; H, 8.75.
Observed: C, 73.72; H, 8.73.

Step 3: (E)-Methyl 5,6,7,8-tetrahydro-2-naphthalenehex-delta-enoate

A mixture of the alcohol from Step 2 (22.6 g), benzene (15.0 ml) and p-toluenesulfonic acid (500 mg) was refluxed for 30 minutes as the water produced was collected in a Dean Stark apparatus. The mixture was concentrated and chromatographed on silica gel to provide the title compound as an oil.

NMR ($CDCl_3$) 6.75–7.15 (m, 3H), 5.85–6.5 (m, 2H), 3.65 (s, 3H), 2.5–2.9 (m, 4H), 1.2–2.4 (m, 10H).

Step 4: (E)-Methyl delta,epsilon-epoxy-5,6,7,8-tetrahydronaphthalenehexanoate To a mixture of the (E)-olefin from Step 3 (5 g), dichloromethane (750 ml) and 1N $NaHCO_3$ (250 ml) was added m-chloroperbenzoic acid (4.9 g). The mixture was stirred for 2 hours and then calcium hydroxide (15 g) was added. After stirring for 15 minutes more, the mixture was filtered and the filtrate concentrated and chromatographed on silica gel to provide the title compound as an oil.

NMR ($CDCl_3$): 6.7–7.1 (m, 3H), 3.8–4.0 (m, 1H), 3.6 (s, 1H), 3.45–3.55 (d, 1H), 1.1–3.1 (m, 14H).

Step 5: D,L-Erythro-methyl epsilon-((3-((3-methoxy-1,3-dioxopropyl)amino)-phenyl)thio)-5,6,7,8-tetrahydro-delta-hydroxy-2-naphthalenehexanoate A mixture of the epoxide from Step 4 (1.5 g), the thiol from Example 12 (1.3 g), triethylamine (3.0 ml) and methanol (50 ml) was stirred at room temperature for 18 hours. The mixture was concentrated and chromatographed on silica gel to provide the title compound as an oil.

NMR ($CDCl_3$) 9.0–9.3 (broad, 1H), 6.85–7.65 (m, 7H), 4.1–4.25 (d, 1H), 3.7–3.9 (broad, 1H), 3.8 (s, 3H), 3.6 (s, 3H), 3.45 (s, 2H), 2.5–2.85 (m, 3H), 2.1–2.4 (m, 2H), 1.2–1.9 (m, 10H).

Step 6: Erythro-epsilon-((3-((carboxyacetyl)amino)-phenyl)thio)-5,6,7,8-tetrahydro-delta-hydroxy-2-naphthalenehexanoic acid disodium salt sesquihydrate A mixture of the diester from Step 5 (1.7 g), 1N sodium hydroxide (12 ml) and methanol (65 ml) was stirred at room temperature for 2 hours. The mixture was concentrated and purified on XAD-8 resin to provide the title compound.

Analysis, calculated: C, 54.34; H, 5.57; N, 2.58; S, 5.90.
Observed: C, 55.32; H, 5.61; N, 2.53; S, 5.94.

EXAMPLE 103

Preparation of D,L-Erythro-7-((5-carboxy-2-hydroxy-1-(5,6,7,8-tetrahydro-2-naphthalenyl)pentyl)thio)-2-methoxy-3-quinolinecarboxylic acid disodium salt sesquihydrate

Step 1. Erythro-methyl 7-((2-hydroxy-6-methoxy-6-oxo-1-(5,6,7,8-tetrahydro-2-naphthalenyl)-hexyl)thio)-2-methoxy-3-quinolinecarboxylate A mixture of the epoxide from Example 102, Step 4 (1.6 g), the thiol from Example 9 (1.5 g), triethylamine (3.0 ml) and methanol (50 ml) was stirred at room temperature for 18 hours. The mixture was filtered and the filtrate concentrated and chromatographed on silica gel to provide the title compound.

Analysis, calculated: C, 66.51; H, 6.35; N, 2.67; S, 6.12.
Observed: C, 65.27; H, 6.21; N, 2.91; S, 6.87.

Step 2: D,L-Erythro-7-((5-carboxy-2-hydroxy-1-(5,6,7,8-tetrahydro-2-naphthalenyl)pentyl)-thio)-2-methoxy-3-quinolinecarboxylic acid disodium salt sesquihydrate A mixture of the diester from Step 1 (1.8 g), 1N sodium hydroxide (14 ml) and methanol (75 ml) was stirred at room temperature for 18 hours. The mixture was concentrated and purified on XAD-8 resin to provide the title compound, m.p. 235° (dec.)

Analysis, calculated: C, 57.23; H, 5.33; N, 2.47; S, 5.65.
Observed C, 57.35; H, 5.22; N, 2.45; S, 5.93.

EXAMPLE 104

Preparation of 6-((2-carboxyethyl)thio)-5-hydroxyhexanoic acid bis(dicyclohexylamine) salt

Step 1. 6-((2-carboxyethyl)thio)-5-hydroxyhexanoic acid-delta-lactone

Dimethyldithiopropionate (1.5 g) in $CHCl_3$ (40 ml) was cooled to $-30°$ C. and treated with $Cl_2$ gas dissolved in $CCl_4$ (5.25 ml of 85 mg $Cl_2$ ml$^{-1}$). The above solution was added to a $-30°$ C. mixture of 6-hexenoic acid (750 mg) and trimethylamine (0.9 ml) in $CHCl_3$ (15 ml). The mixture was maintained at $-30°$ C. for 1 hour then stirred 15 hours at room temperature. Sodium bicarbonate (10 ml, 5% solution) was added and the reaction stirred 12 hours at room temperature. The organic layer was separated and concentrated. The residue was purified by chromatography on silica gel to yield the title compound as a viscous oil.

NMR ($CDCl_3$): 4.5 (1H, m), 3.7 (3Hs, $OCH_3$), 2.8 (2H, t), 2.6 (2H, t), 2.4 (2H, m), 1.9 (4H, m).

Step 2. 6-((2-carboxyethyl)thio)-5-hydroxyhexanoic acid bis(dicyclohexylamine)salt The lactone from Step 1 above (600 mg) was stirred in a mixture of THF (20 ml), 2N lithium hydroxide (3 ml) and $H_2O$ (10 ml). After 10 hours stirring the THF was removed by concentration, the solution was diluted with $H_2O$, made strongly acidic with conc. HCl (2 ml) and extracted with $CHCl_3$ (5×20 ml). The $CHCl_3$ extracts were dried with anhydrous sodium sulphate and filtered. To the $CHCl_3$ solution was added dicyclohexylamine (540 mg). The solution was then stirred 1 hour, and the $CHCl_3$ was removed under reduced pressure to yield a white solid, which yielded upon crystallization from ethyl acetate/methanol the title compound, m.p. 152°–154°.

Analysis, calculated: C, 66.179; H, 10.434; N, 4.677; Observed: C, 65.96; H, 10.77; N, 4.53

EXAMPLE 105

Preparation of D,L-Erythro-7-((5-carboxy-1-(3,4-dichlorophenyl)-2-hydroxypentyl)thio)-4-oxo-4H-1-benzopyran-2-carboxylic acid disodium salt sesquihydrate Step 1. Methyl epsilon-oxo-(3,4-dichlorophenyl)-hexanoate Monomethyl adipic acid chloride (10 g) was combined with aluminum chloride (14.5 g) without solvent at 0° C. 1,2-dichlorobenzene (8 g) was then added and the mixture was heated under $N_2$ for 6 hours at 100°. Upon cooling the reaction mixture was poured onto ice water (300 ml) and $CHCl_3$ (300 ml). The organic phase was dried and concentrated to yield an oil. This residue was purified on silica gel to yield the title compound, m.p. 49°–51°.

Step 2. Methyl epsilon-hydroxy-(3,4-dichlorophenyl)hexanoate

The keto ester from Step 1 (8 g) was taken up in methanol (120 ml) to which was added in 3 portions, at room temperature, sodium borohydride (1.6 g). After 20 minutes the reaction was quenched with a saturated solution of ammonium chloride (150 ml) followed by acidification with conc. HCl. The methanol was removed under reduced pressure, and the aqueous solution was extracted with methylene chloride (8×50 ml). The residue after concentration was chromatographed on silica gel to yield the title compound.

NMR ($CDCl_3$) 7.4 (1H, d), 7.3 (1H, s), 7.2 (1H, dd), 4.6 (1H, t), 3.6 (3H, s, $OCH_3$), 2.3 (2H, t), 1.6 (6H, m).

Step 3. (E)-Methyl(3,4-dichlorophenyl)-hex-delta-enoate

The hydroxy ester from Step 2 (5 g) and p-toluene sulfonic acid (650 mg) in dry toluene (80 ml) was refluxed under $N_2$ in a Dean Stark apparatus for 8 hours. The reaction mixture was concentrated, dissolved in methylene chloride (200 ml) and washed with 5% sodium bicarbonate (2×50 ml) and $H_2O$ (50 ml). The organic phase was dried and concentrated. The residue was chromatographed on silica gel to provide the title compound as an oil.

NMR ($CDCl_3$): 7.4 (1H, d), 7.3 (1H, s), 7.2 (1H, dd), 6.2 (2H, m), 3.6 (3H, s, $OCH_3$), 2.3 (4H, m), 1.9 (2H, m).

Step 4. (E)-methyl delta,epsilon-epoxy-(3,4-dichlorophenyl)hexanoate

The ester from Step 3 (2 g) was dissolved in methylene chloride (25 ml) to which was added a solution of m-chloroperbenzoic acid (1.78 g) in methylene chloride (20 ml). The mixture was stirred 15 hours at room temperature. Calcium hydroxide (1.8 g) was added and reaction was filtered after 10 minutes. The filtrate was concentrated, and residue chromatographed on silica gel to yield the title compound, m.p. 36°–38°.

Step 5. D,L-Erythro-methyl 7-((1-(3,4-dichlorophenyl)-2-hydroxy-6-methoxy-6-oxohexyl)thio)-4-oxo-4H-1-benzopyran-2-carboxylate The epoxide from Step 4 (1.5 g) was combined with methyl 7-mercapto-4-oxo-4H-1-benzopyran-2-carboxylate (1.1 g) in methanol (15 ml) and triethylamine (7.5 ml) and stirred at room temperature under $N_2$ for 20 hours. The residue, upon concentration, was crystallized from methylene chloride/ethyl acetate/hexane to yield the title compound; m.p. 121°–123°.

Analysis, calculated: C, 54.87; H, 4.22; S, 6.10; Observed: C, 54.65; H, 4.26; S, 6.09

Step 6. D,L-Erythro-7-((5-carboxy-1-(3,4-dichlorophenyl)-2-hydroxypentyl)thio)-4-oxo-4H-1-benzopyran-2-carboxylic acid disodium salt sesquihydrate The diester from Step 5 (1.0 g) was stirred in 0.2N sodium hydroxide (19.9 ml) and tetrahydrofuran (20 ml) at room temperature under $N_2$ for 20 hours. The solvent was removed in vacuo to yield the title compound; m.p. dec 250°.

Analysis, calculated: C, 46.49; H, 3.40; S, 5.83; Observed: C, 46.33; H, 3.62; S, 5.74

EXAMPLE 106

Preparation of D,L-erythro-7-(5-carboxy-2-hydroxy-1-(3-nonylphenyl)pentylthio)-4-oxo-8-propyl-4H-1-benzopyran2-carboxylic acid disodium salt dihydrate Step 1. meta-Bromobenzyltriphenylphosphonium bromide meta-Bromobenzylbromide (100 g) was taken up in toluene (1.5 l) to which was added triphenyl phosphine (100 g). The mixture was refluxed under $N_2$ for 2.5 hours then stirred at room temperature for 20 hours. The resulting precipitate was filtered to yield the title compound: m.p. 302°–304°.

Step 2. 3-(1-nonenyl)bromobenzene

The phosphonium salt from Step 1 (150 g) was added to a suspension at 0° C. of potassium t-butoxide (33 g) in tetrahydrofuran (1800 ml). After stirring 30 minutes at 0° C. under $N_2$, octylaldehyde (37.6 g) in tetrahydrofuran (50 ml) was added dropwise. After addition the mixture was warmed to room temperature for 2 hours. Diethyl ether (1 l) was added, the mixture was filtered, washed with water, dried and concentrated. Chromatography on silica gel provided the title compound as an oil.

NMR ($CDCl_3$); 7.4 (1H, m), 7.25 (3H, m), 6.25 (2H, m), 2.2 (2H, m), 1.3 (10H, m), 0.95 (3H, t).

Step 3. 3-nonylbromobenzene

The olefin from Step 2 (30 g) in ethyl alcohol (450 ml) and platinum oxide (500 mg) was reduced with hydrogen at 3 psi for 20 minutes. The catalyst was removed by filtration through a bed of Celite/sodium sulphate and the ethanol was concentrated to yield the title compound as an oil.

NMR ($CDCl_3$) 7.4 (1H, d), 7.3 (1H, m), 7.2 (2H, dd), 2.6 (2H, t), 1.7 (2H, m), 1.3 (12H, m), 0.9(3H, t).

Step 4. Methyl epsilon-hydroxy-(3-nonylbenzene)hexanoate

The bromide from Step 3 (20 g) in tetrahydrofuran (25 ml) was added to a suspension of magnesium metal (1.9 g) in anhydrous tetrahydrofuran (30 ml). The solution was refluxed under $N_2$ for 2 hours following the addition. In parallel, methyl 5-formylpentanoate (13 g) was taken up in tetrahydrofuran (20 ml) and cooled to −78° C. The Grignard reagent was then cooled to −20° C. and added to the aldehyde maintained at −78° C. Stirring was continued 30 minutes at −78° C. The reaction was quenched with saturated ammonium chloride (120 ml) and then was extracted with diethyl ether (5×50 ml). The residue after concentration of the ether extracts were purified on silica gel to provide the title compound as an oil.

NMR (CDCl$_3$) 7.2 (4H, m), 4.7 (1H, m), 3.7 (3H, s), 2.6 (2H, t), 2.3 (3H, m), 1.65 (9H, m), 1.3 (11H, m), 0.95 (3H, t).

Step 5. (E)-methyl (3-nonylbenzene)hex-delta-enoate

The hydroxy ester from Step 4 (10 g) was dissolved in toluene (200 ml) containing p-toluene-sulphonic acid (1.1 g) and refluxed with a Dean Stark apparatus for 3 hours. The mixture was concentrated in vacuo and dissolved in chloroform (300 ml). The chloroform solution washed with 5% sodium bicarbonate (2×75 ml), saturated sodium chloride (1×100 ml), then dried and concentrated. The residue was purified on silica gel to provide the title compound as an oil.

NMR (CDCl$_3$): 7.2 (4H, m), 6.3 (1H, d), 6.2 (1H, q), 3.7 (3H, s), 2.6 (2H, q), 2.3 (3H, m), 1.8 (2H, m), 1.7 (2H, m), 1.3 (13H, m), 0.95 (3H, m).

Step 6. (E)-methyl delta,epsilon-epoxy-(3-nonylbenzene)hexanoate

The olefin from Step 5 (5.6 g) was dissolved in methylene chloride (75 ml) to which was added m-chloroperbenzoic acid (4.0 g). The reaction was stirred 2 hours at room temperature. Calcium hydroxide (6 g) was then added, the mixture was stirred 10 minutes, and then filtered through Celite. After concentration of the filtrate, the residue was chromatographed on silica gel to provide the title compound as an oil.

NMR (CDCl$_3$), 7.2 (4H, m), 3.7 (3H, s), 3.6 (1H, d), 3.0 (1H, m), 2.6 (4H, m), 1.9 (7H, m), 1.3 (11H, m), 0.95 (3H, m).

Step 7. D,L-erythro-methyl 7-((2-hydroxy-6-methoxy-1-(3-nonylphenyl)thio)-6-oxohexyl)-4-oxo-8-propyl-4H-1-benzopyran-2-carboxylate The epoxide from Step 6 (1 g) was combined with methyl 8-propyl-7-mercapto-4-oxo-4H-1-benzopyran-2-carboxylate (730 mg) in methyl alcohol (15 ml) and triethylamine (7.5 ml) and resulting solution was stirred at room temperature under N$_2$ for 15 hours. The reaction mixture was concentrated in vacuo and the residue chromatographed on silica gel to provide the title compound as an oil.

Analysis, calculated: C, 69.20; H, 7.74; S, 5.13;
Observed: C, 69.25; H, 7.91; S, 4.86

Step 8. D,L-erythro-7-(5-carboxy-2-hydroxy-1-(3-nonylphenyl)pentylthio)4-oxo-8-propyl-4H-1-benzopyran 2-carboxylic acid disodium salt dihydrate The diester from Step 7 (1 g) was dissolved in tetrahydrofuran (17 ml) and 0.2N sodium hydroxide (16.8 ml) and stirred at room temperature for 48 hours. The solution was filtered and concentrated to yield the title compound, m.p. 192°–195°.

Analysis, calculated: C, 60.34; H, 6.85; S, 4.73;
Observed: C, 60.39; H, 6.60; S, 4.85.

EXAMPLE 107

Preparation of D,L-erythro-7-((1-(4-butylphenyl)-5-carboxy-2-hydroxypentyl)thio)-4-oxo-8-propyl-4H-1-benzopyran-2-carboxylic acid disodium salt sesquihydrate Step 1. Methyl D,L-erythro-7-((1-(4-butylphenyl)-6-methoxy-6-oxo-2-hydroxyhexyl)thio)-4-oxo-8-propyl-4H-1-benzopyran-2-carboxylate The epoxide from Example 120, Step 1 (1 g) was combined with methyl 8-propyl-7-mercapto-4-oxo-4H-1-benzopyran-2-carboxylate (915 mg) in methyl alcohol (10 ml) and triethylamine (8 ml) and stirred at room temperature under N$_2$ for 15 hours. The reaction mixture was filtered and concentrated. The residue was chromatographed on silica gel to provide the title compound as an oil.

NMR (CDCl$_3$); 7.9 (1H,d), 7.3 (6H, m), 4.4 (2H, d), 4.1 (2H, broad), 4.0 (3H, s), 3.65 (3H, s), 3.15 (2H, t), 2.6 (2H, t), 2.3 (2H, m), 1.7 (10H, m), 1.3 (2H, m), 1.0 (5H, m).

Step 2. D,L-erythro-7-((1-(4-butylphenyl)-5-carboxy-2-hydroxypentyl)thio)-4-oxo-propyl-4H-1-benzopyran-2-carboxylic acid disodium salt sesquihydrate The diester from Step 1 (1.0 g) was taken up in tetrahydrofuran (19 ml) and 0.2N sodium hydroxide (18.93 ml) and stirred at room temperature under N$_2$ for 48 hours. The reaction mixture was concentrated and the solid residue triturated with diethyl ether, to provide the title compound, m.p. 210°.

Analysis, calculated: C, 58.28; H, 5.90; S, 5.36;
Observed: C, 57.91; H, 5.56; S, 5.16

EXAMPLE 108

D,L-erythro-7-((5-carboxy-2-hydroxy-1-(2-nonylphenyl)-pentyl)thio)-4-oxo-8-propyl-4H-1-benzopyran-2-carboxylic acid disodium salt dihydrate Step 1. ortho-Bromo(phenylmethyl)triphenyl phosphonium bromide ortho-Bromobenzylbromide (100 g) was taken up in toluene (1.5 l) to which was added triphenyl phosphine (100 g). The solution was refluxed for 3 hours, then cooled and stirred at room temperature for 15 hours. The solid precipitate was filtered to yield the title compound.

Step 2. 2-(1-Nonenyl)bromobenzene

The phosphonium salt from Step 1 (150 g) was added to a suspension at 0° C. of potassium t-butoxide (33 g) in tetrahydrofuran (1800 ml). After stirring for 30 minutes at 0° C. under N$_2$, a solution of octylaldehyde (37.6 g) in tetrahydrofuran (50 ml) was added dropwise. The reaction mixture was then stirred at room temperature for 15 hours. Diethyl ether (1 l) was added and the mixture was filtered, washed with water, dried and concentrated to provide the title compound as an oil.

NMR (CDCl$_3$); 7.5 (1H, m), 7.2 (3H, m), 5.6–6.6 (2H, m), 2.2 (2H, t), 1.4 (10H, m), 0.95 (3H, m).

Step 3. 2-Nonylbromobenzene

The olefin from Step 2 (20 mg) was dissolved in ethyl alcohol (140 ml) and platinum oxide (200 mg) was added. The olefin was reduced with hydrogen at 3 psi for 20 minutes. The mixture was filtered through a bed of Celite/sodium sulfate and the filtrate was concentrated to yield the title compound as an oil.

NMR (CDCl$_3$), 7.5 (1H, d), 7.2 (3H, m), 2.7 (2H, t). 1.7 (2H, m), 1.4 (12H, m), 0.95 (3H, m).

Step 4. Methyl epsilon-hydroxy-2-nonylbenzenehexanoate

The bromide from Step 3 (12.3 g) in tetrahydrofuran (15 ml) was added to a suspension of magnesium (1.2 g) in tetrahydrofuran and the mixture was refluxed 3 hours. In parallel, methyl 5-formylpentanoate (8 g) was taken up in tetrahydrofuran (20 ml) and cooled to −78° C. The Grignard reagent was then cooled to −20° and added to the aldehyde maintained −78° C. Stirring was continued for 30 minutes at −78°. The reaction was quenched with saturated ammonium chloride (100 ml) and then extracted with diethyl ether (5×50 ml). The residue after concentration of the ether extracts was purified on silica gel to provide the title compound as an oil.

NMR (CDCl$_3$): 75 (1H, m), 7.2 (3H, m), 4.9 (1H, m), 3.65 (3H, s), 2.6 (2H, t), 2.3 (2H, t), 1.7 (9H, m), 1.3 (13H, m), 0.95 (3H, m).

Step 5. (E)-methyl (2-nonylbenzene)hex-delta-enoate

The hydroxy ester from Step 4 (4 g) was taken up in toluene (80 ml) containing p-toluene-sulphonic acid (450 mg) and refluxed with a Dean Stark apparatus for 3 hours. The reaction mixture was concentrated, and taken up in chloroform (150 ml), washed with 5% sodium bicarbonate (2×40 ml), saturated sodium chloride (1×50 ml), dried and concentrated. The residue was purified on silica gel to provide the title compound as an oil.

NMR (CDCl$_3$) 7.5 (1H, m), 7.2 (3H, m), 6.7 (1H, d), 6.1 (1H, m), 3.7 (3H, s), 2.6 (2H, t), 2.3 (4H, m), 1.8 (2H, m), 1.7 (2H, m), 1.3 (12H, m), 0.95 (3H, m).

Step 6. (E)-methyl delta-epsilon-epoxy-(2-nonylbenzene)hexanoate

The olefin from Step 5 (2.5 g) was taken up in methylene chlorine (40 ml) to which was added m-chloroperbenzoic acid (1.85 g) in methylene chloride (20 ml). The reaction was stirred at room temperature for 2 hours at which time calcium hydroxide (4 g) was added. After stirring 10 minutes the mixture was filtered on a bed of celite. The solvent was evaporated and the residue was chromatographed on silica gel to provide the title compound as an oil.

NMR (CDCl$_3$): 7.2 (4H, s), 3.8 (1H, d), 3.7 (3H, s), 2.9 (1H, m), 2.6 (2H, m), 2.3 (4H, m), 1.9 (4H, m), 1.4 (12H, m), 0.95 (3H, m).

Step 7. Methyl D,L-erythro-7-((2-hydroxy-6-methoxy-1-(2-nonylphenyl)-6-oxo-hexyl)thio)4-oxo-8-propyl-4H-1-benzopyran-2-carboxylate The epoxide from Step 6 (1.0 g) was combined with methyl 8-propyl-7-mercapto-4-oxo-4H-1-benzopyran-2-carboxylate (730 mg) in methyl alcohol (15 ml) and triethyl amine (7.5 ml). The reaction was stirred 20 hours at room temperature under N$_2$. The mixture was concentrated and purified on silica gel to yield the title compound as an oil.

NMR (CDCl$_3$): 7.9 (1H, d), 7.3 (5H, m), 7.1 (1H, s), 4.7 (1H, d), 4.0 (3H, s), 4.0 (1H, broad) singlet), 3.6 (3H, s), 3.1 (2H, t), 2.5 (2H, m), 2.2 (4H, m), 1.7 (9H, m), 1.2 (13 m), 0.95 (3H, t).

Step 8. D,L-erythro-7-((5-carboxy-2-hydroxy-1-(2-nonylphenyl)pentyl)thio)-4-oxo-8-propyl-4H-1-benzopyran-2-carboxylic acid disodium salt dihydrate The diester from Step 7 (1.0 g) was taken up in tetrahydrofuran (16 ml) and 0.2N sodium hydroxide (16.0 ml) and stirred at room temperature under N$_2$ for 24 hours. Reaction was concentrated to yield the title compound, m.p. 202°–205°.

Analysis: calculated: C, 62.34; H, 6.85; S, 4.73; Observed: C, 59.95; H, 6.85; S, 4.79

EXAMPLE 109

Preparation of D,L-erythro-epsilon-((3-carboxylacetyl)-amino)-phenyl)thio)-delta-hydroxy-3-nonylbenzenehexanoic acid disodium salt monohydrate

Step 1. Methyl D,L-erythro-epsilon-((3-((3-methoxy-3-oxopropyl)amino)phenyl)thio)-delta-hydroxy-3-nonylbenzenehexanoate The epoxide from Example 106, Step 6 (1.19 g) was combined with the thiol from Example 12 (890 mg) in methyl alcohol (15 ml) and triethylamine (7.5 ml) and stirred at room temperature under N$_2$ for 20 hours. The reaction was concentrated and the residue chromatographed on silica gel to yield the title compound as an oil.

NMR (CDCl$_3$): 9.0 (1H, s), 7.5 (1H, s), 7.4 (1H, d), 7.2 (5H, m), 4.2 (1H, d), 3.9 (1H, bs), 3.8 (3H, s), 3.6 (3H, s), 3.4 (2H, s), 2.5 (2H, t), 2.3 (2H, m), 1.6 (9H, m), 1.3 (11, m), 0.95 (3H, t).

Step 2. D,L-erythro-epsilon-((3-((carboxyacetyl)amino)-phenyl)thio)-delta-hydroxy-3-nonylbenzenehexanoic acid disodium salt monohydrate The ester from Step 1 (1.0 g) was taken up in tetrahydrofuran (17.5 ml) and 2N sodium hydroxide (17.5 ml) and stirred for 24 hours under N$_2$ at room temperature. The reaction mixture was concentrated to yield the title compound, m.p. 200° (dec).

Analysis, calculated: C, 59.49; H, 6.82; S, 5.29; Observed: C, 59.09; H, 6.71; S, 5.17.

EXAMPLE 110

Preparation of D,L-erythro-epsilon-(((3-carboxyphenyl)methyl)thio)-delta-hydroxy-4-nonylbenzenehexanoic acid disodium salt dihydrate

Step 1. Methyl D,L-erythro-delta-hydroxy-epsilon-(((3-methoxyoxomethyl)phenyl)methyl)thio)-4-nonylbenzenehexanoate The epoxide from Example 48, Step B (1 g) was combined with 3-(methoxyoxomethyl)phenylmethylmercaptan (500 mg) in methyl alcohol (15 ml) and trimethylamine (7.5 ml) under N$_2$ at rom temperature. After 30 hours the solvents were removed in vacuo and the residue chromatographed on silica gel to yield the title compound as an oil.

NMR (CDCl$_3$): 7.9 (2H, m), 7.2 (6H, m), 3.9 (3H, s), 3.8 (1H, m), 3.55 (3H, s), 3.5 (3H, m), 2.6 (2H, t), 2.3

(2H, t), 1.9 (1H, d), 1.6 (7H, m), 1.2 (11H, m), 0.95 (3H, t).

Step 2. D,L-Erythro-epsilon-(((3-carboxyphenyl)-methyl)thio)-delta-hydroxy-4-nonylbenzenehexanoic acid disodium salt dihydrate The ester from Step 1 (1 g) was taken up in tetrahydrofuran (20 ml) and 0.2N sodium hydroxide (19.4 ml) and stirred at room temperature under N$_2$ for 48 hours. The residue upon concentration was triturated with 20% methanol/ether to yield the title compound, m.p. 270° (dec).

Analysis, calculated: C, 59.98; H, 7.28; S, 5.52;
Observed: C, 61.12; H, 7.02; S, 5.21

EXAMPLE 111

Preparation of D,L-Erythro-epsilon-((3-((carboxyacetyl)amino)-phenyl)thio)-delta-hydroxy-4-nonylbenzenehexanoic acid disodium salt sesterhydrate

Step 1. Methyl D,L-erythro-delta-hydroxy-epsilon-((3-methoxy-1,3-dioxopropyl)amino)phenyl)thio)-4-nonylbenzenehexanoate The expoxide from Example 48, Step B (1.5 g) was combined with the thiol from Example 12 (1.18 g) in methanol (25 ml) and triethylamine (10 ml) and stirred 15 hours at room temperature under N$_2$. The reaction mixture was concentrated, and the residue was chromatographed on silica gel to yield the title compound as an oil.

NMR (CDCl$_3$): 9.1 (1H, s), 7.6 (1H, m), 7.4 (1H, m), 7.3 (2H, m), 7.2 (4H, m), 4.3 (1H, d), 3.9 (1H, bs), 3.8 (3H, s), 3.6 (3H, s), 3.4 (2H, s), 2.6 (2H, t), 2.3 (2H, t), 1.6 (9H, m), 0.95 (3H, t).

Step 2. D,L-Erythro-epsilon-((3-((carboxyacetyl)amino)-phenyl)thio)-delta-hydroxy-4-nonylbenzenehexanoic acid disodium salt sesterhydrate The diester from Step 1 (1.95 g) was taken up in tetrahydrofuran (40 ml) and 0.2N sodium hydroxide (40 ml) and stirred at room temperature under N$_2$ for 48 hours. The solvent was removed to yield the title compound, m.p. 240° (dec).

Analysis, calculated: C, 53.37; H, 6.09; N, 2.49; S, 5.69;
Observed: C, 53.72; H, 5.74; N, 2.51; S, 5.49

EXAMPLE 112

Preparation of (2S,5S),(2S,5R),(2R,5S),(2R,5R)-2-Butyl-6-((3-((carboxyacetyl)amino)phenyl)thio)-5-hydroxyhexanoic acid disodium salt monohydrate

Step 1. 2-Butylhex-delta-enoic acid

Delta-hexenoic acid (2 g) in tetrahydrofuran (25 ml) was cooled to $-20°$ C. under N$_2$. Lithium diisopropylamide (2.1 eq) was then added and the reaction mixture was warmed to room temperature for 30 minutes. The reaction mixture was again cooled to $-20°$ C. and then n-butyliodide (2.1 ml) was added and the reaction mixture was warmed to room temperature where it was maintained for 12 hours. Ice water was added and the mixture was made acidic with 12N HCl. The mixture was extracted with diethyl ether, the ether was dried and concentrated to yield the title compound as an oil.

NMR (CDCl$_3$): 10.6 (1H, bs), 5.7 (1H, m), 4.9 (2H, m), 2.3 (1H, m), 2 (2H, m), 1.6 (4H, m), 1.2 (4H, m), 0.95 (3H, m).

Step 2. Methyl-2-butylhex-delta-enoate

The acid from Step 1 (3.3 g) was dissolved in diethyl ether (940 ml) to which was added an excess of diazomethane in diethyl ether. The solvent was evaporated to yield the title compound as an oil. NMR (CDCl$_3$): 5.7 (1H, m), 4.9 (2H, m), 3.6 (3H, s), 2.3 (1H, m), 2.0 (2H, m), 1.6 (4H, m), 1.2 (4H, m), 0.95 (3H, m).

Step 3. Methyl 2-butyl-delta,epsilon-epoxy-hexanoate

The ester from Step 2 (2.0 g) was taken up in methylene chloride (100 ml) to which was added m-chloroperbenzoic acid (4.1 g) and the mixture was stirred at room temperature under N$_2$ for 4.5 hours. The mixture was concentrated and chromatographed on silica gel to yield the title compound as an oil.

NMR (CDCl$_3$): 3.6 (3H, s), 2.9 (1H, m), 2.7 (1H, t), 2.5 (2H, m) 1.6 (6H, m), 1.2 (4H, m), 0.95 (3H, t).

Step 4. Methyl (2S,5S) (2S,5R) (2R,5S) (2R,5R)-5-hydroxy-6-((3-((3-methoxy-1,3-dioxopropyl)-amino)phenyl)thio)-2-n-butyl-hexanoate The epoxide from Step 3 (800 g) was combined with the thiol from Example 12 (910 mg) in methanol (20 ml) and triethylamine (7 ml) and stirred under N$_2$ at room temperature for 15 hours. The solvent was removed in vacuo and the residue was chromatographed on silica gel to yield the title compound as an oil.

NMR (CDCl$_3$): 9.2 (1H, bs), 7.6 (1H, m), 7.3 (2H, m), 7.1 (1H, m), 3.8 (3H, s), 3.65 (1H, bs), 3.65 (3H, s), 3.45 (2H, s), 3.0 (2H, m), 2.4 (2H, m), 1.6 (6H, m), 1.2 (4H, m), 0.95 (3H, t).

Step 5. (2S,5S) (2S,5R) (2R,5S) (2R,5R)-2-Butyl-6-((3-((carboxyacetyl)amino)phenyl)-thio)-5-hydroxyhexanoic acid disodium salt monohydrate The diester from Step 4 (1.1 g) was taken up in tetrahydrofuran (28 ml) and 0.2N sodium hydroxide (27 ml) and stirred at room temperature under N$_2$ for 48 hours. The solvent was removed in vacuo to yield the title compound, m.p. 150° (dec).

Analysis, calculated: C, 49.67; H, 5.92; N, 3.05; S, 7.00.
Observed: C, 50.07; H, 6.03; N, 2.93; S, 7.56.

EXAMPLE 113

Preparation of 7-(((2S,5S),(2S,5R),(2R,5S)-(2R,5R)-5-Carboxy-2-hydroxynonyl)thio)-4-oxo-8-propyl-4H-1-benzopyranyl-2-carboxylic acid disodium salt monohydrate

Step 1. Methyl 7-(((2S,5S),(2S,5R),(2R,5S),(2R,5R)-2-hydroxy-3-(methoxycarbonyl)nonyl)thio)-4-oxo-8-propyl-4H-1-benzopyran-2-carboxylate The epoxide from Example 112, Step 3 (453 mg) was combined with methyl 8-propyl-7-mercapto-4-oxo-4H-1-benzopyran-2-carboxylate (600 mg) in methanol (15 ml) and triethylamine (5 ml) and stirred at room temperature under N$_2$ for 30 hours. The solvent was removed in vacuo and the residue was chromatographed on silica gel to provide the title compound, m.p. 70°–72°.

Analysis: calculated: C, 62.74; H, 7.16; S, 6.70.
Observed: C, 62.66; H, 7.15; S, 6.79.

Step 2.
7-(((2S,5S),(2S,5R),(2R,5S),(2R,5R)-5-Carboxy-2-hydroxynonyl)thio)-4-oxo-8-propyl-4H-1-benzopyran-2-carboxylic acid disodium salt monohydrate The diester from Step 1 (600 mg) was taken up in tetrahydrofuran (13 ml) and 0.2N sodium hydroxide (13.0 ml). The mixture was stirred at room temperature under $N_2$ for 36 hours, then concentrated in vacuo. The residue was triturated with ether/methanol to yield the title compound, m.p. 195°–200°.

Analysis, calculated: C, 53.90; H, 5.90; S, 6.26.
Observed: C, 53.98; H, 5.82; S, 6.37.

EXAMPLE 114

Preparation of D,L-7-((5-Carboxy-2-(3-((butylthio)-methyl)phenyl)-pentyl)oxy)-4-oxo-8-propyl-4H-1-benzopyran-2-carboxylic acid disodium salt

Step 1. 1-Bromo-3-((butylthio)methyl)-benzene

1-Butanethiol (9.5 g) was taken up in tetrahydrofuran (250 ml) and cooled to 0° C. under $N_2$. To this solution was added aqueous sodium hydroxide (59.6%) and the mixture was stirred for 30 minutes at 0° C. 3-Bromobenzylbromide (25 g) was then added and the mixture was stirred at room temperature for 15 hours. Ice water was added and reaction mixture was extracted with chloroform. The organic extracts were dried and concentrated. The residue was chromatographed on silica gel to yield the title compound as an oil.

NMR (CDCl$_3$): 7.5 (1H, m), 7.4 (1H, m), 7.25 (2H, m), 3.65 (2H, s), 2.45 (2H, t), 1.5 (4H, m), 0.95 (3H, t).

Step 2. Methyl delta-hydroxy-3-((butylthio)methylbenzenehexanoate

Magnesium metal (2.3 g) was suspended in tetrahydrofuran (25 ml). The bromide from Step 1 (22 g) in THF (60 ml) was added to maintain reflux, and at the end of addition the mixture was refluxed for 3 hours. Methyl 5-formylpentanoate (15.2 g) was taken up in tetrahydrofuran (60 ml) and cooled to −78° C. under $N_2$. The Grignard reagent was cooled to 0° C. and added to the solution of aldehyde at −78° C. The reaction mixture was maintained at −78° C. for 30 minutes, then warmed to 0° C. and quenched with saturated ammonium chloride (100 ml). The mixture was extracted with ether. The ether was dried and concentrated and the residue was chromatographed on silica gel to yield title compound as an oil.

NMR (CDCl$_3$): 7.3 (4H, m), 4.6 (1H, m), 3.7 (3H, s), 3.7 (2H, s), 3.7 (1H, m), 2.4 (6H, m), 1.6 (8H, m), 0.95 (3H, t).

Step 3. Methyl D,L-7-((6-methoxy-6-oxo-2-((butylthio)methyl)-phenyl)hexyl)oxy)-4-oxo-8-propyl-4H,1-benzopyran-2-carboxylate The alcohol from Step 2 (1 g) and ethyl-8-propyl-7-hydroxy-4-oxo-4H-1-benzopyran-2-carboxylate (940 mg) were combined in tetrahydrofuran (50 ml) with diethylazodicarboxylate (1.07 g) at 0° C. under $N_2$. Triphenylphosphine (1.9 g) in THF (20 ml) was added dropwise over 30 minutes to the cooled solution. The mixture stirred 15 hours at room temperature, then concentrated. The residue was chromatographed on silica gel to yield the title compound as an oil.

NMR (CDCl$_3$): 7.4 (1H, d), 7.3 (4H, m) 7.0 (1H, s), 6.8 (1H, d), 5.2 (1H, t), 4.4 (2H, q), 3.6 (3H, s), 3.6 (2H, s), 3.0 (2H, t), 2.4 (4H, m), 1.7 (7H, m), 1.4 (8H, m), 1.0 (3H, t), 0.95 (3H, t).

Step 4.
7-((5-Carboxy-2-(3-((butylthio)methyl)phenyl)-oxy)-4-oxo-8-propyl-4H-1-benzopyran-2-carboxylic acid disodium salt The ester from Step 3 (1.08 g) was taken up in tetrahydrofuran (20 ml) and 0.2N sodium hydroxide (19.5 ml) under $N_2$ and was stirred at room temperature for 48 hours. The reaction mixture was concentrated to yield the title compound, m.p. 175°–180° (dec).

Analysis, calculated: C, 61.63; H, 5.86; S, 5.48.
Observed: C, 61.49; H, 5.67; S, 5.23.

EXAMPLE 115

Preparation of D,L-7-((1-(3-((Butylthio)methyl)-phenyl)-5-carboxypentyl)thio)-4-oxo-8-propyl-4H-1-benzopyran-2-carboxylic acid disodium salt

Step 1. D,L-Methyl 7-((1-(3-((butylthio)methyl)-phenyl)-6-methoxy-6-oxo-hexyl)thio)-4-oxo-8-propyl-4H-1-benzopyran-2-carboxylate Triphenylphosphine (1.2 g) was taken up in tetrahydrofuran at 0° C. under $N_2$. To this solution was added diethylazodicarboxylate (800 mg) with stirring for 30 mins. A mixture of the alcohol from Example 114, Step 2 (740 mg) and methyl 7-mercapto-8-propyl-4-oxo-4H-1-benzopyran-2-carboxylate (700 mg) in tetrahydrofuran (25 ml) was added to the above mixture at 0° C. After stirring 1 hour at room temperature the reaction mixture was concentrated and the residue was chromatographed on silica gel to yield the title compound as an oil.

NMR (CDCl$_3$): 7.8 (1H, d), 7.3 (5H, m) 7.0 (1H, s), 4.3 (1H, m), 4.0 (3H, s), 3.6 (3H, s), 3.6 (2H, s), 3.0 (2H, t), 2.3 (4H, m), 2.0 (2H, m), 1.5 (10H, m), 1.0 (3H, t), 0.95 (3H, t).

Step 2.
7-((1-(3-((Butylthio)methyl)phenyl)-5-carboxypentyl)-thio)-4-oxo-8-propyl-4H-1-benzopyran-2-carboxylic acid disodium salt The ester from Step 1 (700 mg) was taken up in tetrahydrofuran (13 ml) and 0.2N sodium hydroxide (12.5 ml) at room temperature under $N_2$ with stirring for 48 hours. The reaction mixture was concentrated to yield the title compound, m.p. 200° (dec).

Analysis, calculated: C, 59.97; H, 5.71; S, 10.67.
Observed: C, 59.77; H, 5.90; S, 10.48.

EXAMPLE 116

Preparation of D,L-Erythro-7-((5-carboxy-1-(4-(1,1-dimethylethyl)-phenyl)-2-hydroxypentyl)thio)-4-oxo-8-propyl-4H-1-benzopyran-2-carboxylate disodium salt monohydrate

Step 1. D,L-Methyl (E)-delta,epsilon-epoxy-4-(1,1-dimethylethyl)benzenehexanoate Following the procedure described in Example 105, Steps 1, 2, 3 and 4, but substituting an equivalent amount of 4-t-butylbenzene for 3,4-dichlorobenzene in Step 1, was obtained sequentially:

A—Methyl epsilon-oxo-(4-(1,1-dimethylethyl)-benzene)hexanoate, as an oil: NMR (CDCl): 1.4₃(9H, s), 1.6–2.0 (4H, m), 2.3–2.6 (2H, m), 2.9–3.2 (2H, m), 3.75 (3H, s), 7.5 (2H, d, J=7.5 Hz), 8.0 (2H, d, J=7 5 Hz).

B—Methyl epsilon-hydroxy-(4-(1,1-dimethylethyl)-benzene)hexanoate, as an oil:NMR (CDCl): 1.4₃(9H, s), 1.4–2.0 (6H, m), 2.4 (2H, t, J=6 Hz), 2.5 (2H, s), 3.7 (3H, s), 4.6 (1H, t, 5=6 Hz), 7.25 (2H, d, J=9 Hz), 7.45 (2H, d, 5=9 Hz).

C—(E)-(4-(1,1-Dimethylethyl)benzene)hex-deltaenoate, as an oil:NMR (CDCl₃): 1.4 (9H, s), 1.8 (2H, quint.), 2.3 (4H, quint.), 3.65 (3H, s), 5.9–6.5 (2H, m), 7.35 (4H, s).

D—and the title compound, as an oil:NMR (CDCl): 1.3₃(9H, s), 1.55–2.0 (4H, m), 2.4 (2H, t), 2.85–3.05 (1H, m), 3.6 (1H, d), 3.7 (3H, s), 7.2 (2H, d), 7.4 (2H, d).

Step 2. D,L-Erythro-methyl 7-((1-(4-(1,1-dimethylethyl)phenyl)-2-hydroxy-6-methoxy-6-oxohexyl)-thio)-4-oxo-8-propyl-4H-1-benzopyran-2-carboxylate Following the procedure described in Example 113, Step 1, but substituting an equivalent amount of the epoxide from Step 1 above for methyl 2-butyldelta,epsilon-epoxy-hexanoate was obtained the title compound, as an oil.

Analysis, calculated: C, 67.12; H, 6.90; S, 5.78.
Observed: C, 67.05; H, 6.92; S, 5.54.

Step 3. D,L-Erythro-7-((5-carboxyl-(4-(1,1-dimethylethyl)-phenyl)-2-hydroxypentyl)thio)-4-oxo-8-propyl-4H-1-benzopyran-2-carboxylate disodium salt monohydrate The diester from Step 2 (715 mg) was stirred in THF (10 ml) and 0.2N NaOH (18.4 ml) at ambient temperature for 18 hours. The mixture was concentrated in vacuo to remove the THF and applied to a column of Amberlite XAD-8 resin. The column was washed with water until the effluent was neutral. Eluting with ethanol gave after concentration to dryness, the title compound, as a foam.

Analysis, calculated: C, 59.17; H, 5.82; S, 5.45.
Observed: C, 58.93; H, 5.45; S, 5.57.

EXAMPLE 117

Preparation of D,L-Erythro-7-((6-carboxy-2-hydroxy-1-(4-nonylphenyl)hexyl)thio)-4-oxo-8-propyl-4H-1-benzopyran-2-carboxylic acid disodium salt

Step 1. Methyl delta-oxo-(4-octylphenyl)pentanoate

Methyl 4-(chloroformyl)butyrate (15.2 ml) was added to a stirred suspension of anhydrous aluminum chloride (32 g) in anhydrous 1,2-dichloroethane and the mixture was stirred under N₂ atmosphere at ambient temperature for 15 minutes. n-phenyloctane (15.2 ml) was added slowly and after 30 minutes the mixture was poured into water and ice. The mixture was extracted with CH₂Cl₂ (2×100 ml) and the combined organic phases were washed with brine, dried (Na₂SO₄) and reduced to dryness to provide the title compound, as an oil: NMR (CDCl₃): 0.9 (3H, t), 1.1–1.8 (12H, m), 2.0 (2H, quint.), 2.45 (2H, t), 2.6 (2H, t), 3.0 (2H, t), 3.6 (3H, s), 7.2 (2H, d), 7.85 (2H, d).

Step 2. 2-(4-Octylphenyl)tetrahydro-6-oxo-2H-pyran

A solution of the ketone from Step 1 (30 g) in methanol (150 ml) was stirred with aqueous 3N NaOH (47.3 ml) at 50° for 30 minutes. The mixture was cooled to ambient temperature and the mixture was diluted with water (200 ml). Sodium borohydride (5.4 g) was added by portions and the mixture was vigourously stirred at ambient temperature for 1.5 hours. The mixture was slowly poured into a mixture of ice, water (400 ml) and concentrated HCl (12 ml) to be finally acidified with more concentrated HCl to pH3. The mixture was extracted with CH₂Cl₂ (2X) and the combined organic phases were washed with H₂O, dried (Na₂SO₄) and reduced to dryness to provide an oil. This oil was dissolved in toluene (200 ml) and hydrated p-toluenesulfonic acid (1.8 g) was added. The mixture was stirred at ambient temperature and after 45 minutes the mixture was evaporated to dryness and the residue was chromatographed on silica gel to provide the title compound.

NMR (CDCL₃): 0.95 (3H, t), 1.2–1.9 (12H, m), 1.9–2.3 (4H, m), 2.5–2.8 (4H, m), 5.3 (1H, t), 7.1–7.4 (4H, m).

Step 3. 2-(4-Octylphenyl)-6-hydroxy-tetrahydro-2H-pyran

A solution of lactone from Step 2 (15g) in anhydrous toluene (260 ml) was cooled under N₂ at −78° and a solution of 25% by weight diisobutylaluminium hydride in toluene (57 ml) was added. The mixture was stirred at −78° and after 5 minutes, the mixture was poured into a solution of concentrated HCl (14 ml) and water (200 ml) and extracted with diethyl ether (2X). The combined organic phases were washed with water, dried (Na₂SO₄) and evaporated in vacuo to provide the title compound, as an oil: NMR (CDCl₃): 0.9 (3H, t), 1.1–2.1 (18H, m), 2.6 (2H, t), 3.5–5.4 (3H, m), 7.0–7.3 (4H, m).

Step 4. Methyl (E)- and (Z)-zeta-hydroxy-(4-octylphenyl)hept-alpha-enoates

A solution of lactol from Step 5 (15 g) and (carbomethoxymethylene)triphenylphosphorane (26 g) in CHCl₃ (200 ml) was refluxed for 4 hours. The mixture is cooled to ambient temperature and reduced to dryness in vacuo. The residue was chromatographed on silica gel to provide the title compound, as an oil: NMR (CDCl₃): 0.9 (3H, t), 1.1–1.85 (16H, m), 1.9 (1H, s), 2.0–2.4 (2H, m), 2.6 (2H, t), 3.7 (3H, s), 4.65 (1H, t), 5.75 and 5.8 (d and d resp. 1H), 5.85–6.2 and 6.85 (m and t resp., 1H), 7.0–7.3 (4H, m).

Step 5. Methyl Zeta-hydroxy-4-octylbenzeneheptanoate

A solution of olefin from Step 4 (15.3 g) in THF (150 ml) was hydrogenated under 40 psi of hydrogen in the presence of 5% palladium on charcoal (1.0 g) for 10 minutes. Then the reaction mixture was filtered on a bed of celite, washed with THF and the filtrate was evaporated in vacuo to provide the title compound, as a white solid: m.p. 49°–50°.

Step 6. Methyl (E)-4-octylbenzenehept-epsilon-enoate

A solution of alcohol from Step 5 (12.3 g) in toluene (150 ml) was refluxed in the presence of hydrated p-toluenesulfonic acid (1.34 g) and after 20 minutes the mixture was cooled to ambient temperature and reduced to dryness. The residue was chromatographed on silica gel to provide the title compound, as an oil:

NMR (CDCl₃): 0.9 (3H, t), 1.1–1.9 (16H, m), 2.1–2.5 (4H, m), 2.6 (2H, t), 3.7 (3H, s), 5.95–6.5 (2H, m), 7.1 (2H, d), 7.3 (2H, d).

Step 7. Methyl (E)-epsilon,zeta-epoxy-4-octylbenzenehept-epsilon-enoate

To a solution of olefin from Step 6 (9.0 g) in CH₂Cl₂ (75 ml) was added a solution of 85% m-chloroperbenzoic acid (6.6 g) in CH₂Cl₂ (100 ml). The mixture was stirred at ambient temperature and after 2 hours, treated with calcium hydroxide (7.3 g). The heterogeneous solution was stirred for 10 minutes and the salts were filtered and the filtrate was reduced to dryness. The residue was chromatographed on silica gel to provide the title compound, as an oil: NMR (CDCl₃): 0.9 (3H, t), 1.1–1.5 (12H, m), 1.5–1.9 (6H, m), 2.4 (2H, t), 2.65 (2H, t), 2.95 (1H, m), 3.6 (1H, d), 3.7 (3H, s), 7.2 (4H, s).

Step 8. D,L-Erythro-methyl 7-((2-hydroxy-7-methoxy-1-(4-octylphenyl)-7-oxoheptyl)thio)-4-oxo-8-propyl-4H-1-benzopyran-2-carboxylate Following the procedure described in Example 113, Step 1, but substituting an equivalent amount of the epoxide from Step 7 for methyl 2-butyl-delta, epsilon-epoxyhexanoate was obtained the title compound, as an oil.

Analysis, calculated: C, 69.20; H, 7.74; S, 5.13.
Observed: C, 69.16; H, 8.00; S, 5.04.

Step 9. D,L-Erythro-7-((6-carboxy-2-hydroxy-1-(4-nonylphenyl)hexyl)thio)-4-oxo-8-propyl-4H-1-benzopyran-2-carboxylic acid disodium salt The diester from Step 8 (287 mg) was stirred in THF (8 ml) and 0.2N NaOH (4.8 ml) at ambient temperature for 18 hours. The mixture was concentrated in vacuo to remove the THF and purified on a column of amberlite XAD-8 resin as described in Example 116, Step 3 to provide the title compound, as a foam.

Analysis, calculated: C, 63.73; H, 6.61; S, 5.00.
Observed: C, 63.42; H, 6.79; S, 4.86.

EXAMPLE 118

Preparation of (Epsilon S, zeta R) and (epsilon R, zeta S)-zeta-3-((((carboxyacetyl)amino)phenyl)thio)-epsilon-hydroxy-4-nonylbenzeneheptanoic acid disodium salt

Step 1. D,L-Erythro-methyl epsilon-hydroxy-zeta-((3-((3-methoxy-1,3-dioxopropyl)amino)phenyl)-thio)-4-octylbenzeneheptanoate Methyl (E)-epsilon,zeta-epoxy-4-octylbenzeneheptanoate methyl ester (364 mg) and the thiol from Example 12 (210 mg) in anhydrous methanol (5 ml) and triethylamine (0.37 ml) were stirred under N₂ atmosphere at ambient temperature for 18 hours. The mixture was reduced to dryness and chromatographed on silica gel to provide the title compound, as an oil.

Analysis, calculated: C, 67.22; H, 7.93; N, 2.45, S, 5.61.
Observed: C, 66.96; H, 8.37; N, 2.75; S, 5.42.

Step 2. (Epsilon S, zeta R) and (epsilon R, zeta S)-zeta-3-((((carboxyacetyl)amino)phenyl)thio)-epsilon-hydroxy-4-nonylbenzeneheptanoic acid disodium salt The diester from Step 1 (315 mg) was stirred in THF (10 ml) and 0.2N NaOH (5.8 ml) at ambient temperature for 18 hours. The mixture was concentrated in vacuo to remove the THF and then purified on a column of amberlite XAD-8 resin as described in Example 117, Step 3 to provide the title compound, as a foam.

Analysis, calculated: C, 61.31; H, 6.69; N, 2.38; S, 5.46.
Observed: C, 61.31; H, 6.67; N, 2.42; S, 5.45.

EXAMPLE 119

Preparation of 7-((5-Carboxy-2(S)-hydroxy-1(R)-(2(E)-(4-octylphenyl)ethenyl)pentyl)thio)-4-oxo-8-propyl-4H-1-benzopyran-2-carboxylic acid disodium salt

Step 1. 4-(Bromomethyl)-n-octylbenzene

A solution of 4-n-octylbenzenemethanol (22.8 g) in benzene (90 ml) was added dropwise to cooled (0°) phosphorus tribromide (4.9 ml). After complete addition, the reaction mixture was diluted with diethyl ether (200 ml), washed with water (2×200 ml), 5% sodium bicarbonate, brine, dried (Na₂SO₄) and reduced to dryness. The residue was chromatographed on silica gel to provide the title compound, as a white solid, m.p. 31°–33°.

Step 2. ((4-n-Octylphenyl)methyl)triphenylphosphonium bromide

A solution of bromide from Step 1 (25 g) and triphenylphosphine (16.7 g) in dry toluene (150 ml) was refluxed for 3 hours. The reaction mixture was cooled to ambient temperature and a white solid was formed. The mixture was diluted with diethyl ether (200 ml) and stirred for 30 minutes. The solid was filtered, washed with diethyl ether, dried under vacuum to provide the title product, as a white solid, m.p. 155°–157°.

Step 3. Methyl delta(S),epsilon(R)-delta,epsilonepoxy-(2(E)-(4-octylphenyl)ethenyl)hexanoate A suspension of the phosphonium bromide from Step 2 (13.9 g) in anhydrous THF (28 ml) was cooled to 0° under N₂ atmosphere and was added a solution of 1.6N n-butyllithium in hexane (4.7 ml). The mixture was stirred for 10 minutes and a solution of methyl 6-formyl-5S,6R-epoxy hexanoate (1.0 g) in anhydrous THF (10 ml) was added. After 10 minutes, the reaction mixture was warmed to ambient temperature and diluted with water and diethyl ether. The aqueous layer was extracted with diethyl ether (3×) and the combined organic layers were washed with water, dried (Na₂SO₄) and reduced to dryness. The residue was chromatographed on a column of deactivated silica gel to provide the title compound, as a solid, m.p. 25°, [α]_D −155° (C=0.667, CHCl₃).

Analysis, calculated: C, 77.05; H, 9.56.
Observed: C, 76.90; H, 9.38.

Step 4. Methyl 7-((2(S)-hydroxy-6-methoxy-1(R)-(2(E)-4-nonylphenyl-)ethenyl)-6-oxohexyl)thio)-4-oxo-8-propyl-1H-1-benzopyran-2-carboxylate Chiral epoxyde from Step 3 (250 mg), methyl 7-mercapto-8-propyl-4'-oxo-4H-1-benzopyran-2-carboxylate (128 mg) and anhydrous methanol (0.06 ml) were mixed together for 1 minutes. To this mixture was added more anhydrous methanol (1.2 ml). After 10 minutes the mixture was reduced to dryness and the residue was chromatographed on deactivated silica gel to provide the title product, as an oil, $[\alpha]_D -139°$ (C=0.887, CHCl$_3$).

Analysis, calculated: C, 69.78; H, 7.60; S, 5.04.
Observed: C, 69.63; H, 7.45; S, 5.29.

Step 5. 7-((5-Carboxy-2(S)-hydroxy-1(R)-(2(E)-(4-octylphenyl-)ethenyl)pentyl)thio)-4-oxo-8-propyl-4H-1-benzopyran-2-carboxylic acid disodium salt hydrate The diester from Step 4 (225 mg) was stirred in THF (13 ml) and 0.2N NaOH (3.7 ml) at ambient temperature for 18 hours. The mixture was concentrated in vacuo to remove the THF and then purified on a column of Amberlite XAD-8 resin as described in Example 117, Step 3 to provide the title compound, as a foam, $[\alpha]_D -223°$ (C=0.78, CHCl$_3$).

Analysis, calculated: C, 64.40; H, 6.49; S, 4.91.
Observed: C, 64.27; H, 6.56; S, 4.82.

EXAMPLE 120

Preparation of D,L-Erythro-7((1-(4-butylphenyl)-5-carboxy-2-hydroxypentyl)thio)-4-methyl-2-oxo-2H-1-benzopyran-3-acetic acid disodium salt monohydrate

Step 1. D,L-Methyl delta,epsilon-(E)-epoxy-(4-butylbenzene)hexanoate

Following the procedure described in Example 105, Steps 1, 2, 3 and 4 but substituting an equivalent amount of 4-n-butylbenzene for 3,4-dichlorobenzene in Step 1 was obtained, sequentially:

A—Methyl epsilon-oxo-(4-butylphenyl)hexanoate as an oil: NMR (CDCl$_3$): 1.0 (3H, t), 1.3–2.0 (8H, m), 2.4 (2H, t), 2.7 (2H, 5), 3.0 (2H, t), 3.7 (3H, s), 7.3 (2H, d), 7.95 (2H, d).

B—Methyl epsilon-hydroxy-(4-butylphenyl)-hexanoate as an oil: NMR (CDCl$_3$): 0.9 (3H, t), 1.0–2.0 (10H, m), 2.3 (2H, t), 2.5 (1H, s), 2.6 (2H, t), 3.6 (3H, s), 4.6 (1H, t), 7.2 (4H, t).

C—(E)-(4-Butylphenyl-hex-delta-enoate as an oil: NMR (CDCl$_3$): 0.95 (3H, t), 1.2–2.1 (6H, m), 2.2–2.55 (4H, m), 2.6 (2H, t), 3.7 (3H, s), 5.9–6.5 (2H, m), 7.1 (2H, d), 7.3 (2H, d).

D—D,L-Methyl delta, epsilon-(E)-epoxy-(4-butylphenyl)hexanoate as an oil. NMR (CDCl$_3$): 0.9 (3H, t), 1.2–2.1 (8H, m), 2.3–2.8 (4H, m), 3.0 (1H, td), 3.65 (1H, d), 3.7 (3H, s), 7.2 (4H, s).

Step 2. D,L-Erythro-methyl 7-((1-(4-butylphenyl)-2-hydroxy-6-methoxy-6-oxohexyl)thio)-4-methyl-2-oxo-8-propyl-2H-1-benzopyran-3-acetate The epoxide from Step 1 (522 mg) and methyl 7-mercapto-4-methyl-2-oxo-8-propyl-2H-1-benzopyran-3-acetate, (from Example 11), (526 mg) in anhydrous methanol (10 ml) and triethylamine (0.72 ml) were stirred under N$_2$ atmosphere at ambient temperature for 18 hours. The mixture was reduced to dryness and chromatographed on silica gel to provide the title compound, as a white solid, m.p. 91°–9.3°.

Analysis, calculated: C, 68.01; H, 7.27; S, 5.50.
Observed: C, 67.95; H, 7.20; S, 5.20.

Step 3. D,L-Erythro-7-((1-(4-butylphenyl)-5-carboxy-2-hydroxypentyl)thio)-4-methyl-2-oxo-2H-1-benzopyran-2-acetic acid disodium salt monohydrate The diester from Step 2 (771 mg) was stirred in THF (10 ml) and 0.2N NaOH 93 ml) at ambient temperature for 18 hours. The mixture was concentrated to remove the THF and then purified on a column of Amberlite XAD-8 resin as described in Example 117, Step 3 to provide the title compound, as a foam.

Analysis, calculated: C, 60.37; H, 6.21; S, 5.20.
Observed: C, 60.11; H, 6.38; S, 5.23.

EXAMPLE 121

Preparation of D,L-(E)-Erylthro-7-((5-carboxy-2-hydroxy-1-(2-(4-octylphenyl)ethenyl)pentyl)thio)-4-oxo-8-propyl-4H-1benzopyran-2-carboxylic acid disodium salt dihydrate

Step 1. Ethyl (4-octylphenyl)-prop-alpha-enoate

A solution of 4-octylbenzaldehyde (22 g) and (carboethoxymethylene)triphenylphosphorane (46 g) in CH$_2$Cl$_2$ (250 ml) was stirred at ambient temperature. After 1 hour, the mixture is reduced to dryness and the residue was chromatographed on silica gel to provide the title compound, as an oil.

NMR (CDCl$_3$): 0.9 (3H, t), 1.1–1.8 (12H, m), 2.65 (2H, t), 4.25 (2H, q), 6.35 (1H, d), 7.15 (2H, d), 7.4 (2H, d), 7.65 (1H, d).

Step 2. 3-(4-Octylphenyl)-2-propen-1-ol

A solution of ester from Step 1 (20.5 g) in THF (60 ml) was added to a cooled suspension of aluminium hydride (5 g) in THF (50 ml). The mixture was stirred at ambient temperature and after 2 hours, a saturated aqueous solution of ammonium chloride was added and extracted with hexane (2X). The combined organic layers were washed with water, dried (Na$_2$SO$_4$) and reduced to dryness. The residue was chromatographed on silica gel to provide the title compound, m.p. 30°.

NMR (CDCl$_3$): 0.87 (3H, t), 1.1–1.8 (13H, m, 1h exchanged with D$_2$O), 2.57 (2H, t), 4.23 (1H, t, d after D$_2$O exchange), 6.23 (2H, dt), 6.53 (1H, d), 7.07 and 7.25 (4H, ABq).

Step 3. 1-Bromo-3-(4-octylphenyl)-2-propene

Following the procedure described in Example 119, Step 1 but substituting an equivalent amount of alcohol from Step 2 above for 4-n-octylbenzenemethanol was obtained the title compound, as an oil: NMR (90 MHz) (CDCl$_3$): 0.90 (3H, t), 1.1–1.8 (12H, m), 2.60 (2H, t), 4.13 (2H, d), 6.30 (1H, dt), 6.62 (1H, d), 7.07 and 7.25 (4H, ABq).

Step 4. D,L-Methyl delta,epsilon-(E)-epoxy-(2(E)-(4-octylphenyl)ethenyl)-hexanoate Following the procedure described in Example 122, Step 1 but substituting an equivalent amount of bromide from Step 3 for cinnamyl bromide was obtained the title compound, as an oil: NMR (90 MHz) (CDCl$_3$): 0.87 (3H, t), 1.1–2.1 (16H, m), 2.37 (2H, t), 2.60 (2H, t), 2.92

(1H, td), 3.23 (1H, dd), 3.67 (3H, s), 5.82 (1H, dd), 6.70 (1H, d), 7.03 and 7.30 (4H, ABq).

Step 5. D,L-Methyl (E)-erythro-7-((2-hydroxy-6-methoxy-6-oxo-1-(2-(4-octylphenyl)ethenyl)hexyl)thio)-4-oxo-8-propyl-4H-1-benzopyran-2-carboxylate Following the procedure described in Example 119, Step 4 but substituting an equivalent amount of epoxyde from Step 4 above for methyl delta(S)-epsilon(R)-delta,epsilon-epoxy-(2-(E)-(4-octylphenyl)-ethenyl)hexanoate was obtained the title compound, as an oil:

NMR (CDCl$_3$): 0.87 (3H, t), 1.00 (3H, t), 1.1–2.2 (19H, m, 1H exchanged with D$_2$O), 2.37 (2H, t), 2.55 (2H, t), 3.09 (2H, t), 3.63 (3H, s), 3.8–4.2 (5H, m; including 3H, s), 6.17 (1H, dd), 6.45 (1H, d), 7.00 (1H, s), 7.0–7.25 (4H, ABq), 7.43 (1H, d), 7.9 (1H, d).

Step 6. D,L-(E)-Erythro-7-((5-carboxy-2-hydroxy-1-(2-(4-octylphenyl)ethenyl)pentyl)thio)-4-oxo-8-propyl-4H-1-benzopyran-2-carboxylic acid disodium salt dihydrate The diester from Step 5 (138 mg) was stirred in THF (10 ml) and 0.2N NaOH (2.3 ml) at ambient temperature for 18 hours. The mixture was concentrated in vacuo to remove the THF and then purified on a column of Amberlite XAD-8 resin as described in Example 117, Step 3 to provide the title compound, as a foam.

Analysis, calculated: C, 61.03; H, 6.73; S, 4.66.
Observed: C, 60.94; H, 6.75; S, 5.15.

EXAMPLE 122

Preparation of D,L-(E)-Erythro-7-((5-carboxy-2-hydroxy-1-(2-phenylethenyl)pentyl)thio)-4-oxo-8-propyl-4H-1-benzopyran-2-carboxylic acid disodium salt monohydrate Step 1. D,L-Methyl delta,epsilon(E)-epoxy-(2-(E)-phenylethenyl)hexanoate Tetrahydrothiophene (8.6 ml) was added to a suspension of cinnamyl bromide (16 g) in a mixture of methanol (80 ml) and water (8 ml) and the mixture was stirred at ambient temperature for 1 hour. The mixture was concentrated in vacuo to remove the solvent and the residue was dissolved in dichlorometane (120 ml). Methyl 4-formylbutyrate (11.6 g, 65% pure) and triethylbenzylammonium chloride (0.60 g) were added. The mixture was cooled to −30° C., 10N NaOH (100 ml) was added and the mixture was vigorously stirred for 5 minutes. The mixture was cooled to −70° and extracted with diethyl ether (4×500 ml). The combined organic phases were washed with cold water, brine, dried (Na$_2$SO$_4$) and reduced to dryness and chromatographed on silica gel to provide the title compound, m.p. 40°–41°.

Analysis, calculated: C, 73.15; H, 7.37.
Observed: C, 73.03; H, 7.40.

Step 2. D,L-Methyl (E)-erythro-7-((2-hydroxy-6-methoxy-6-oxo-1-(2-phenylethenyl)hexyl)thio)-4-oxo-8-propyl-4H-1-benzopyran-2-carboxylate A solution of the epoxide from Step 1 (0.39 g) and methyl 7-mercapto-8-propyl-4-oxo-4H-1-benzopyran-2-carboxylate (0.44 g) in methanol (10 ml) was cooled to 0° C. under of nitrogen and triethylamine (70 µl) was added. The mixture was stirred at 0° C. for 15 minutes, poured into crushed ice, and extracted with diethyl ether (30 ml×4). The combined organic phases were washed with brine, dried over Na$_2$SO$_4$ and reduced to dryness to provide the title compound as an oil.

NMR (CDCl$_3$): 1.00 (3H, t), 1.4–2.0 (6H, m), 2.30 (2H, t), 2.7 (1H), 3.10 (2H, t), 3.63 (3H, s), 3.8–4.15 (5H, m, including 3H, s), 6.20 (1H, dd), 6.50 (1H, dd), 7.00 (1H, s), 7.1–7.4 (5H, m), 7.43 (1H, d), 7.90 (1H, d).

Step 3. D,L-(E)-Erythro-7-((5-carboxy-2-hydroxy-1-(2-phenylethenyl)pentyl)thio)-4-oxo-8-propyl-4H-1-benzopyran-2'-carboxylic acid disodium salt monohydrate The diester from Step 2 (130 mg) was stirred in THF (10 ml) and 0.2N NaOH (2.6 ml) at ambient temperature for 18 hours. The mixture was concentrated in vacuo to remove the THF and purified on a column of Amberlite XAD-8 resin as described in Example 117, Step 3 to provide the title compound, as a foam.

Analysis, calculated: C, 58.06; H, 5.05; S, 5.74.
Observed: C, 58.08, H, 5.03; S, 5.71.

EXAMPLE 123

Preparation of D,L-(E)-Erythro-6-((3-((carboxyacetyl)-amino)-phenyl)thio)-5-hydroxy-8-phenyl-7-octenoic acid disodium salt sesquihydrate Step 1. D,L-(E)-Erythro-methyl 5-hydroxy-6-((3-((3-methoxy-1,3-dioxopropyl)phenyl)-thio)-8-phenyl-7-octenoate The epoxide from Example 122, Step 1 (261 mg) was added to a solution of the thiol from Example 12 (254 mg) in anhydrous methanol (0.5 ml) and triethylamine and stirred at ambient temperature for 18 hours. The mixture was reduced to dryness and chromatographed on silica gel to provide the title compound, as an oil.

Analysis, calculated: C, 63.67; H, 6.20; N, 2.97; S, 6.80.
Observed: C, 63.79; H, 6.32; N, 2.88; S, 6.61.

Step 2. D,L-(E)-Erythro-6-((3-((carboxyacetyl)amino)phenyl)-thio)-5-hydroxy-8-phenyl-7-octenoic acid disodium salt sesquihydrate The diester from Step 1 (300 mg) was stirred in THF (8 ml) and 0.2N NaOH (6.7 ml) at ambient temperature for 5 minutes. The mixture was concentrated in vacuo to remove the THF and purified on a column of Amberlite XAD-8 resin as described in Example 117, Step 3 to provide the title compound, as a foam.

Analysis, calculated: C, 53.69; H, 5.09; N, 2.72; S, 6.23.
Observed: C, 53.55; H, 5.15; N, 2.53; S, 6.66.

EXAMPLE 124

Preparation of (E)-(5(S),6(R) and 5(R),6(S)-6-((3-((Carboxyacetyl)amino)phenyl)thio)-5-hydroxy-8-(4-octylphenyl)-7-octenoic acid disodium salt monohydrate Step 1. Methyl (E)-(5(S),6(R) and 5(R),6(S)-5-hydroxy-6-((3-((3-methoxy-1,3-dioxopropyl)-amino)phenyl)thio)-8-(4-octylphenyl)-7-octenoate A mixture of the epoxide from Example 121, Step 4 (220 mg) and the thiol from Example 12, in methanol (2 ml) and triethylamine (50 µl) was stirred at −10° for 1 hour, then 18 hours at ambient temperature. The volatile components were removed by evaporation and chromatography of the residue on silica gel provided the title compound, as an oil.

Step 2. (E)-(5(S),6(R) and 5(R),6(S)-6-((3-((Carboxyacetyl)amino)phenyl)thio)-5-hydroxy-8-(4-octylphenyl)-7-octenoic acid disodium salt monohydrate The diester from Step 1 (270 mg) in THF (3 ml) and 1N NaOH (1.2 ml) was stirred under $N_2$ for 18 hours at ambient temperature. The mixture was concentrated to remove methanol and the aqueous solution purified on XAD-8 resin to provide the title compound, m.p. 190°–195°.

Analysis, calculated: C, 60.28; H, 6.68; N, 2.26; S, 5.19;
Observed: C, 60.12; H, 6.96; N, 2.10; S, 5.73.

EXAMPLE 125

Preparation of D,L-Erythro-epsilon-((3-((carboxyacetyl)amino)-phenyl)thio)-delta-hydroxy-4-phenoxybenzenehexanoic acid

Step 1. Methyl epsilon-oxo-(4-phenoxybenzene)-hexanoate

A mixture of diphenyl ether (850 mg), monomethyl adipic mono acid chloride (898 mg) and 1,2-dichloroethane (15 ml), at 0° was treated with aluminum chloride (1.50 g) with stirring for 30 minutes. The mixture was poured onto ice, and extracted with $CH_2Cl_2$. The extract was dried ($MgSO_4$) and concentrated by evaporation, and the residue was puried by chromatography on silica gel to provide the title compound as an oil.

Analysis, calculated: C, 73.06; H, 6.45.
Observed: C, 73.21; H, 6.40.

Step 2. Methyl epsilon-hydroxy-(4-phenoxybenzene)hexanoate

A mixture of the ketone from Step 1 (12.48 g), in methanol (156 ml) was treated with sodium borohydride (1.87 g) added in portions with stirring at ambient temperature. After 2 hours the mixture was diluted with water, acidified with conc. HCl and extracted with $CH_2Cl_2$. The organic extract was dried ($MgSO_4$) and evaporated to provide the title compound as an oil.

Analysis, calculated: C, 72.58; H, 7.09.
Observed: C, 72.58; H, 7.10.

Step 3. Methyl (E)-4-phenoxybenzenehex-delta-enoate

A mixture of the alcohol from Step 2 (9.27 g) and toluene sulphonic acid monohydrate (800 mg) in toluene (100 ml) was refluxed under a Dean Stark water separator for 45 minutes. The mixture was cooled, diluted with ether (100 ml), washed with 10% $K_2CO_3$, brine, dried ($MgSO_4$) and evaporated to yield a residue which was purified by chromatography on silica gel to provide the title compound as an oil.

Analysis, calculated: C, 77.00; H, 6.80.
Observed: C, 77.19; H, 6.87.

Step 4. Methyl (E)-delta,epsilon-epoxy-4-phenoxybenzenehexanoate

A mixture of the olefin from Step 3 (4.25 g), 85% m-chloroperbenzoic acid (3.34 g) and $CH_2Cl_2$ (200 ml) was stirred at 0° for 15 minutes the 4 hours at ambient temperature. Calcium hydroxide (6.7 g) was added, the mixture was stirred 2 hours, then filtered and evaporated to an oil. Chromatography on silica gel gave the title compound, as an oil.

Analysis, calculated: C, 73.06; H, 6.45.
Observed: C, 73.31′ H, 6.49.

Step 5. Methyl D,L-erythro-epsilon-((3-((3-methoxy-1,3-dioxopropyl)amino)phenyl)thio)deltahydroxy-4-phenoxybenzenehexanoate A mixture of the epoxide from Step 4 (1.154 g) and the thiol from Example 12 (883 mg) in methanol (20 ml) and triethylamine (2.4 ml) was stirred under argon, at ambient temperature for 48 hours. The mixture was evaporated to dryness and the residue was chromatographed on silica gel to provide the title compound as an oil.

Analysis, calculated: C, 64.78; H, 5.81; N, 2.61; S, 5.96.
Observed: C, 64.55; H, 5.90; N, 2.53; S, 6.30.

Step 6. D,L-Erythro-epsilon-((3-((carboxyacetyl)-amino)-phenyl)thio)-delta-hydroxy-4-phenoxybenzenehexanoic acid A mixture of the dimethyl ester from Step 5 (886 mg), methanol (20 ml), 85% KOH (300 ml) and water (2 ml) was stirred 2 hours at ambient temperature. Ether (100 ml) was added, the mixture wa acidified with 0.5N HCl and the ethereal layer was separated, washed with water, brine, dried and evaporated to provide the title compound, as a foam. Analysis, calculated: C, 63.63; H, 5.34; N, 2.75; S, 6.29.
Observed: C, 63.84; H, 5.53; N, 2.82; S, 6.78.

What is claimed is:

1. Compound having the formula:

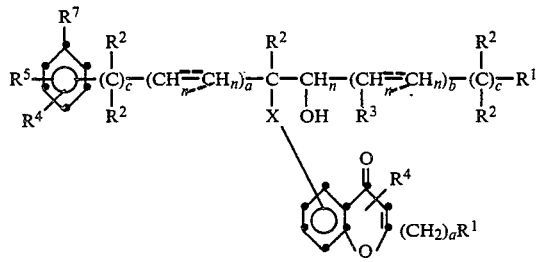

and pharmaceutically acceptable salts thereof wherein:
X is O, S, SO, or $SO_2$;
n is 0 to 2 as required to maintain four bonds to carbon;
the broken lines represent optional double and triple bonds;
a, b, and c are each independently 0 to 5;
$R^1$ is $COOR^2$;
$R^2$ and $R^3$ are each independently H or lower alkyl;
$R^4$ is H, alkyl, halogen, haloalkyl, benzyl, benzyl substituted with at least one $R^7$, aryl, aryl substituted with at least one $R^5$, $NO_2$, CN, $SCF_3$, $OR^3$, O-benzyl, O-benzyl substituted with at least one $R^5$, O-aryl; O-aryl substituted with at least one $R^5$, $SR^{18}$, $NR^2R^3$, $S(O)R^{18}$, or $S(O_2)R^{20}$;
$R^5$ is H, alkyl, halogen, haloalkyl, benzyl, benzyl substituted with at least one $R^3$, $NO_2$, CN, $SCF_3$, $OR^3$, O-benzyl, O-benzyl substituted with at least one $R^3$, O-aryl, $SR^3$, $NR^2R^3$, $S(O)R^{19}$, or $S(O_2)R^{19}$;

$R^7$ is H, alkylthioalkyl, alkylthiobenzyl or alkylthioaryl;
$R^{18}$ is alkyl, haloalkyl, benzyl, or benzyl substituted with at least one $R^3$;
$R^{19}$ is loweralkyl; and
$R^{20}$ is $R^{18}$ or $NR^2R^3$.

2. The compound of claim 1, wherein $R^7$ is H.

3. The compound of claim 1: D,L-erythro-7-((5-carboxy-2-hydroxy-1-(4-nonylphenyl)-pentyl)thio)-4-oxo-8-propyl-4H-1-benzopyran-2-carboxylic acid disodium salt dihydrate;

D,L-erythro-7-((5-carboxy-2-hydroxy-1-(4-nonylphenyl)-pentyl)thio-4-oxo-4H-1-benzopyran-2-carboxylic acid disodium salt trihydrate;

D,L-threo-7-((5-carboxy-2-hydroxy-1-(4-nonylphenyl)-pentyl)thio)-4-oxo-8-propyl-4H-1-benzopyran-2-carboxylic acid monoammonium salt monohydrate;

D,L-erythro-7-((5-carboxy-1-(3,4-dichlorophenyl)-2-hydroxypentyl)thio)-4-oxo-4H-1-benzo-pyran-2-carboxylic acid disodium salt sesquihydrate;

D,L-erythro-7-(5-carboxy-2-hydroxy-1-(3-nonylphenyl)pentylthio)-4-oxo-8-propyl-4H-1-benzopyran-2-carboxylic acid disodium salt dihydrate;

D,L-erythro-7-((1-(4-butylphenyl)-5-carboxy-2-hydroxypentyl)thio)-4-oxo-8-propyl-4H-1-benzopyran-2-carboxylic acid disodium salt sesquihydrate;

D,L-erythro-7-((5-carboxy-2-hydroxy-1-(2-nonylphenyl)-pentyl)thio)-4-oxo-8-propyl-4H-1-benzopyran-2-carboxylic acid disodium salt dihydrate;

D,L-erythro-7-((5-carboxy-1-(4-(1,1-dimethylethyl)-phenyl)-2-hydroxypentyl)thio)-4-oxo-8-propyl-4H-1-benzopyran-2-carboxylate disodium salt monohydrate;

D,L-erythro-7-((6-carboxy-2-hydroxy-1-(4-nonylphenyl)-hexyl)thio)-4-oxo-8-propyl-4H-1-benzopyran-2-carboxylic acid disodium salt;

7-((5-carboxy-2(S)-hydroxy-1(R)-(2(E)-(4-octylphenyl)ethenyl)pentyl)thio)-4-oxo-8-propyl-4H-1-benzopyran-2-carboxylic acid disodium salt;

D,L-(E)-erythro-7-((5-carboxy-2-hydroxy-1-(2-(4-octylphenyl)ethenyl)pentyl)thio)-4-oxo-8-propyl-4H-1-benzopyran-2-carboxylic acid disodium salt dihydrate; or D,L-(E)-erythro-7-((5-carboxy-2-hydroxy-1-(2-phenylethenyl)pentyl)thio)-4-oxo-8-propyl-4H-1-benzopyran-2-carboxylic acid disodium salt monohydrate.

4. The compound 7-((5-carboxy-2(S)-hydroxy-1(R)-(2(E)-(4-octylphenyl)ethenyl)pentyl)thio)-4-oxo-8-propyl-4H-1-benzopyran-2-carboxylic acid disodium salt.

5. The compound D,L-erythro-7-(5-carboxy-2-hydroxy-1-(3-nonylphenyl)pentylthio)-4-oxo-8-propyl-4H-1-benzopyran-2-carboxylic acid disodium salt dihydrate.

* * * * *